US009958451B2

(12) United States Patent
Strongin et al.

(10) Patent No.: US 9,958,451 B2
(45) Date of Patent: *May 1, 2018

(54) NEAR-INFRARED FLUORESCENT DYES WITH LARGE STOKES SHIFTS

(71) Applicant: Portland State University, Portland, OR (US)

(72) Inventors: Robert Michael Strongin, Portland, OR (US); Martha Sibrian-Vazquez, Portland, OR (US); Jorge Omar Escobedo-Cordova, Portland, OR (US); Mark Allen Lowry, Portland, OR (US)

(73) Assignee: Portland State University, Portland, OR (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/969,904

(22) Filed: Dec. 15, 2015

(65) Prior Publication Data
US 2016/0154001 A1    Jun. 2, 2016

Related U.S. Application Data

(63) Continuation of application No. 14/129,223, filed as application No. PCT/US2012/045116 on Jun. 29, 2012, now Pat. No. 9,250,246.

(60) Provisional application No. 61/505,038, filed on Jul. 6, 2011, provisional application No. 61/502,839, filed on Jun. 29, 2011.

(51) Int. Cl.
| | |
|---|---|
| G01N 33/58 | (2006.01) |
| G01N 21/64 | (2006.01) |
| G01N 33/493 | (2006.01) |
| G01N 33/49 | (2006.01) |
| C09B 57/00 | (2006.01) |
| C09B 11/22 | (2006.01) |
| C09B 11/24 | (2006.01) |
| C09B 11/12 | (2006.01) |
| C07D 311/82 | (2006.01) |
| C07D 493/10 | (2006.01) |

(52) U.S. Cl.
CPC ......... *G01N 33/582* (2013.01); *C07D 311/82* (2013.01); *C07D 493/10* (2013.01); *C09B 11/12* (2013.01); *C09B 11/22* (2013.01); *C09B 11/24* (2013.01); *C09B 57/00* (2013.01); *G01N 21/6486* (2013.01); *G01N 33/49* (2013.01); *G01N 33/493* (2013.01); *Y10T 436/141111* (2015.01)

(58) Field of Classification Search
CPC ............ G01N 33/582; G01N 21/6486; G01N 33/493; G01N 33/49; C09B 57/00; C09B 11/22; C09B 11/12; C09B 11/24; C07D 493/10; C07D 311/82; Y10T 436/141111
See application file for complete search history.

(56) References Cited

U.S. PATENT DOCUMENTS

| | | | |
|---|---|---|---|
| 4,945,171 A | 7/1990 | Haugland et al. | |
| 5,130,433 A | 7/1992 | Albarella et al. | |
| 5,227,487 A | 7/1993 | Haugland et al. | |
| 5,750,409 A | 5/1998 | Herrmann et al. | |
| 6,101,406 A | 8/2000 | Hacker et al. | |
| 6,534,316 B2 | 3/2003 | Strongin et al. | |
| 6,918,874 B1 | 7/2005 | Hatch et al. | |
| 9,250,246 B2 * | 2/2016 | Strongin ............. | C07D 311/82 |
| 2008/0261315 A1 | 10/2008 | Strongin et al. | |
| 2009/0018418 A1 | 1/2009 | Markle et al. | |
| 2009/0148956 A1 | 6/2009 | Singaram et al. | |

(Continued)

FOREIGN PATENT DOCUMENTS

| | | |
|---|---|---|
| WO | WO-2005/110109 | 11/2005 |
| WO | WO-2008/011508 | 1/2008 |

OTHER PUBLICATIONS

Strongin, R. M., "Developing fluorogenic reagents for detecting and enhancing bloody fingerprints." NCJRS, Report 277841 (2009): 1-67.*

(Continued)

*Primary Examiner* — John M Mauro
(74) *Attorney, Agent, or Firm* — Klarquist Sparkman, LLP

(57) ABSTRACT

Embodiments of near-infrared (NIR) dyes are disclosed, along with methods and kits for detecting analytes with the NIR dyes. The NIR dyes have a structure according to the general structure

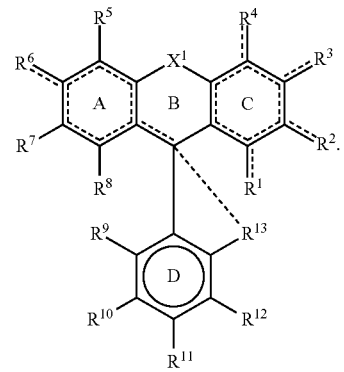

At least one of $R^1/R^2$, $R^2/R^3$, $R^3/R^4$, $R^5/R^6$, $R^6/R^7$, and/or $R^7/R^8$ together forms a substituted or unsubstituted cycloalkyl or aryl.

10 Claims, 30 Drawing Sheets

(56) References Cited

U.S. PATENT DOCUMENTS

| | | |
|---|---|---|
| 2010/0051826 A1 | 3/2010 | Strongin et al. |
| 2010/0278741 A1* | 11/2010 | Spiegel ............... A61K 31/135 424/9.2 |
| 2012/0276649 A1 | 11/2012 | Strongin et al. |

OTHER PUBLICATIONS

Szmacinski, H.,"Optical measurements of pH using fluorescence lifetimes and phase-modulation fluorometry." Analytical Chemistry 65.13 (1993): 1668-1674.*
Fabian, W.M.F., "Effects of annulation on absorption and fluorescence characteristics of fluorescein derivatives: a computational study." Journal of the Chemical Society, Perkin Transactions 2 5 (1996): 853-856.*
Martinez-Otero, A., "Multiplexed arrays of chemosensors by parallel dip-pen nanolithography." Chemical Communications 47.24 (2011): 6864-6866.*
Lee, L.G., "Vita blue: A new 633-nm excitable fluorescent dye for cell analysis." Cytometry Part A 10.2 (1989): 151-164.*
Furukawa, K., "Reduction-triggered red fluorescent probes for dual-color detection of oligonucleotide sequences." Organic & biomolecular chemistry 7.4 (2009): 671-677.*
Chen, X., "Fluorescent and colorimetric probes for detection of thiols." Chemical Society Reviews 39.6 (2010): 2120-2135.*
Borisov et al., "Red light-excitable dual lifetime referenced optical pH sensors with intrinsic temperature compensation," *Analyst*, vol. 135, pp. 1711-1717, 2010.
Chang et al., "A tautomeric zinc sensor for ratiometric fluorescence imaging: Application to nitric oxide-induced release of intracellular zinc," *PNAS*, vol. 101, No. 5, pp. 1129-1134, 2004.
Doddi et al., "Template Effects in the Self-Assembly of a [2]Rotaxane and a [2]Pseudorotaxane with the Same Binding Sites in the Linear Component," *Journal of Organic Chemistry*, vol. 66, No. 14, pp. 4950-4953, Jun. 2001.
Han, "Fluorescent indicators for intracellular pH," *Chemical reviews*, 110.5, pp. 2709-2728, 2009.
International Search Report and Written Opinion, dated Jan. 30, 2013, issued in corresponding International Application No. PCT/US2012/045116.
Kim, "Nonclassical SNAPFL analogue as a Cy5 resonance energy transfer partner," *Organic Letters* 10.21, pp. 4931-4934, 2008.
Nolan et al., "Turn-On and Ratiometric Mercury Sensing in Water with a Red-Emitting Probe," *J. Am. Chem. Soc.*, vol. 129, No. 18, pp. 5910-5918, Apr. 2007.
Sharret, et al., "Boronic Acid-Appended Bis-Viologens as a New Family of Viologen Quenchers for Glucose Sensing," *ScienceDirect*, pp. 300-304, 2008.
Whitaker et al., "Spectral and photophysical studies of benzo[c]xanthene dyes: Dual emission pH sensors," *Anal. Biochem.*, vol. 194, pp. 330-344, 1991.
Yang et al., "A Convenient Preparation of Xanthene Dyes," *Journal of Organic Chemistry*, vol. 70, No. 17, pp. 6907-6912, Jul. 2005.
Yang et al., "An Organic White Light-Emitting Fluorophore," *Journal of the American Chemical Society*, vol. 128, No. 43, pp. 14081-14092, Oct. 2006.
Yang et al., "An Organic White Light-Emitting Fluorophore," *Journal of the American Chemical Society*, vol. 129, p. 1008, Jan. 2007.
Yang et al., "Seminaphthofluorones are a family of water-soluble, low molecular weight, NIR-emitting fluorophores," *PNAS*, vol. 105, No. 26, pp. 8829-8834, Jul. 2008.

* cited by examiner

Scheme 5

Scheme 6

Compound 14a

Compound 8

NEAR-INFRARED FLUORESCENT DYES WITH LARGE STOKES SHIFTS

CROSS REFERENCE TO RELATED APPLICATIONS

This application is a continuation of U.S. application Ser. No. 14/129,223, filed Dec. 24, 2013, now issued as U.S. Pat. No. 9,250,246, which is the National Stage of International Application No. PCT/US2012/045116, filed Jun. 29, 2012, which was published in English under PCT Article 21(2), which in turn claims the benefit of U.S. Provisional Application No. 61/505,038, filed Jul. 6, 2011, and U.S. Provisional Application No. 61/502,839, filed Jun. 29, 2011, each of which is incorporated herein by reference in its entirety.

ACKNOWLEDGMENT OF GOVERNMENT SUPPORT

This invention was made with government support under R01 EB002044 awarded by the National Institutes of Health. The government has certain rights in the invention.

FIELD

Embodiments of near-infrared (NIR) dyes, methods, and kits for detecting analytes are disclosed.

BACKGROUND

A barrier to simplified diagnostic testing is that current clinical chemistry technologies require significant sample preparation and handling for the analysis of complex biological samples. Sample preparation is a major bottleneck in diagnostics. Indicator fluorophores for specific biomarkers capable of functioning directly in an analyte's medium (e.g., blood, urine) without sample handling or separation steps would require fewer manipulations, thereby producing quicker results and reducing potential health hazards due to sample handling. However, surprisingly little progress has been made in developing such fluorophores. This is due at least partially to the relative lack of long wavelength probes.

There are relatively few classes of near infrared (NIR) active dyes that are routinely used, and only one NIR dye is currently approved for clinical use. Advantages of NIR dyes include minimal interfering absorption and fluorescence from biological samples, inexpensive laser diode excitation, and reduced scattering and enhanced tissue penetration depth. However, there are only relatively few classes of such dyes readily available. These include the phthalocyanines, cyanine dyes and squaraine dyes. Each class of dye has inherent strengths and limitations. For example, almost all the established groups of long-wavelength fluorophores have very small Stokes shifts (i.e., emission-excitation wavelength differences), e.g., 10 nm (Miller, *Springer Ser. Fluoresc.*, 2008, 5, 147-162). If used in conjunction with a relatively broad band light source, such as an LED, there may be significant scattered light background signal, producing a poor signal:noise ratio.

Previous research has investigated red-shifting xanthene dyes for biodiagnostics and imaging applications. Long-wavelength, xanthene-based dyes have been used in cellular imaging applications. However, their spectral properties do not fall within the useful NIR "blood window" of 700-800 nm, which facilitates analyte detection in blood. Rhodamines are "red" or long-wavelength xanthene dyes. One notable long wavelength xanthene dye is rhodamine 800, which emits at the interface of the red and NIR, a few nanometers above or below 700 nm depending on the solvent. However, it suffers from limited water solubility and dimer formation and a small Stokes shift of 16 nm (Sauer et al., *J. Fluoresc.*, 1995, 5, 247-261), which complicates analysis in blood. Another innovation includes "JA" dyes, which shift the spectra toward longer wavelength through the addition of double bonds to the nitrogen-containing rings. (Sauer et al.; U.S. Pat. No. 5,750,409). Arden-Jacob and co-workers developed an improved series of fluorophores for biodiagnostics in the red region. However, these dyes exhibit rather small Stokes shifts and do not absorb or emit in the NIR (U.S. Pat. No. 5,750,409).

Annulation is another approach used to produce longer wavelength fluorophores. Type [c] annulated xanthenes include seminaphthofluorescein (SNAFL) and seminaphthorhodafluor (SNARF) compound developed by Haugland (Whitaker et al., *Anal. Biochem.*, 1991, 194, 330-344), which have been used as ratiometric pH sensors, metal ion sensors and imaging probes. (Chang et al., *PNAS*, 2004, 101, 1129-1134; Nolan et al. *J. Am. Chem. Soc.*, 2007, 129, 5910-5918.)

SUMMARY

Embodiments of compounds having emission spectrum maxima in the near-infrared region (near-infrared (NIR) dyes) are disclosed. Some embodiments of the disclosed compounds exhibit large bathochromic shifts and/or enhanced Stokes shifts compared to currently available NIR dyes. Embodiments of the disclosed compounds have a structure according to general formula I.

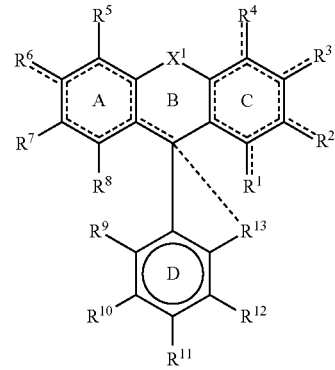

In general formula I, each bond depicted as " ----- " is a single or double bond as needed to satisfy valence requirements. $X^1$ is O, S, Se, $Si(CH_3)_2$, $Ge(CH_3)_2$, $Sn(CH_3)_2$, $CH_2$, $C(CH_3)_2$ or NH; $R^1$, $R^2$, and $R^4$ independently are hydrogen, hydroxyl, oxygen, thiol, lower alkyl, carboxyalkyl, amino, substituted amino, alkoxy, halogen, or —$NHR^c$ where $R^c$ is

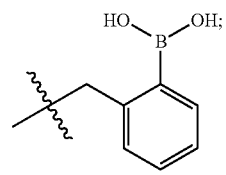 [SMILES: *Cc1ccccc1B(O)O]

$R^5$, $R^7$, and $R^8$ independently are hydrogen, hydroxyl, thiol, lower alkyl, carboxyalkyl, amino, substituted amino, alkoxy, or halogen; R³ and R⁶ independently are hydrogen, hydroxyl, halogen, oxygen, sulfur, thiol, amino, alkyl amino, imino, iminium, alkyl imino, alkyl iminium, cycloalkyl imino, or —NHR$^c$ where R$^c$ is as defined above; and at least one of R¹ and R², R² and R³, R³ and R⁴, R⁵ and R⁶, R⁶ and R⁷, and/or R⁷ and R⁸ together form a substituted or unsubstituted cycloalkyl or aryl. R⁹-R¹² independently are hydrogen, alkyl, acyl, carboxyl, nitro, amino, alkyl amino, or —SO₃H. R¹³ is hydrogen, hydroxyl, lower alkyl, lower alkoxy, —SO₃H or —COOR¹⁴ where R¹⁴ is hydrogen or lower alkyl and the bond depicted as "-----" in ring B is a double bond, or R¹³ is one or more atoms forming a ring system with rings B and D and the bond depicted as "-----" in ring B is a single bond.

In some embodiments, the compounds have a chemical structure according to general formulas (III), (IV), (V), (VI), (VII), (VIII), (IX), (X), or (XI)

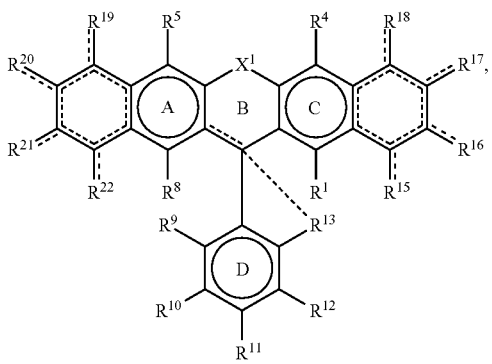

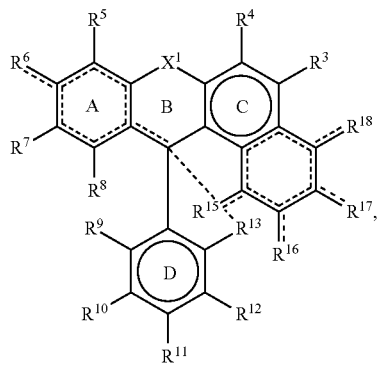

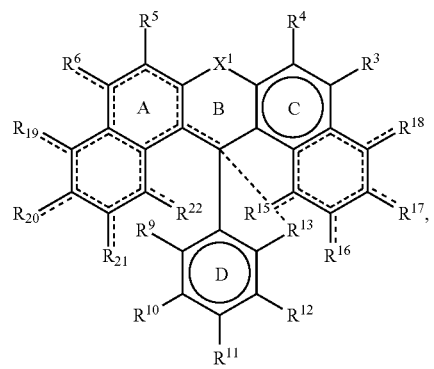

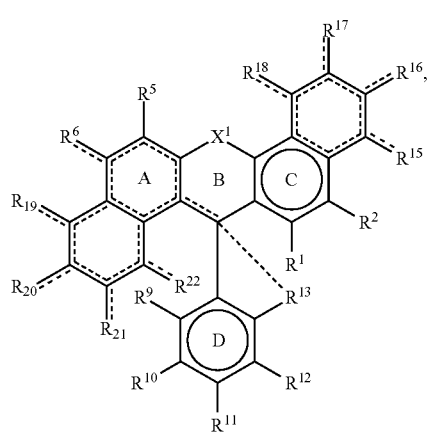

-continued

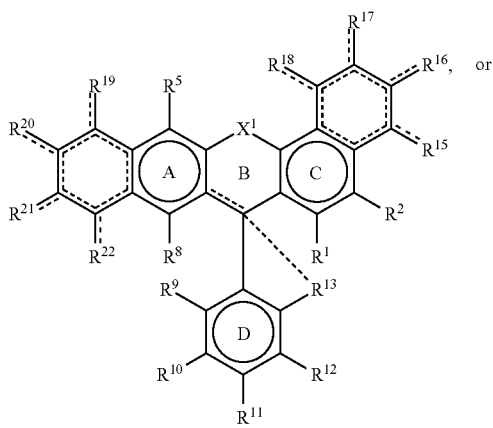

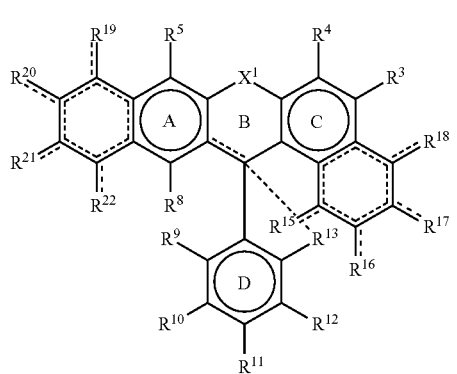

where each bond depicted as "-----" is a single or double bond as needed to satisfy valence requirements; $X^1$, $R^1$-$R^5$ and $R^7$-$R^{14}$ independently are as defined above; $R^6$ is hydrogen, hydroxyl, halogen, thiol, amino, alkyl amino, or —$NHR^c$ where $R^c$ is as defined above when the bond between $R^6$ and ring A is a single bond, or $R^6$ is oxygen, sulfur, imino, iminium, alkyl imino, alkyl iminium, or cycloalkyl imino when the bond between $R^6$ and ring A is a double bond; and $R^{15}$-$R^{22}$ independently are hydrogen, halogen, hydroxyl, oxygen, thiol, amino, alkyl amino, alkoxy, sulfur, imino, iminium, alkyl imino, alkyl iminium, or —$NHR^c$ where $R^c$ is as defined above; and However, if $X^1$ is oxygen in general formula (III), then $R^6$ is other than oxygen or alkyl amino, or $R^{13}$ is other than one or more atoms forming a ring system with rings B and D, or $R^{16}$ is other than hydroxyl or hydrogen, or $R^{18}$ is other than hydroxyl or hydrogen, or at least one of $R^1$, $R^2$, $R^5$, $R^7$, $R^8$, $R^9$, $R^{10}$, $R^{11}$, $R^{12}$, or $R^{13}$ is other than hydrogen; if $X^1$ is oxygen, sulfur, $CH_2$, or NH in general formula (IV), then at least one of $R^1$, $R^2$, $R^7$-$R^{13}$, or $R^{15}$-$R^{22}$ is other than hydrogen, hydroxyl, halogen, oxygen, lower alkyl, amino, or thiol, or $R^{13}$ is one or more atoms forming a ring system with rings B and D and the bond depicted as "-----" in ring B is a single bond; if $X^1$ is oxygen and $R^{15}$ or $R^{17}$ is hydroxyl in general formula (V), then $R^6$ is other than oxygen, amino, or alkyl amino, or at least one of $R^1$, $R^8$, or $R^{18}$ is other than hydrogen, or $R^{13}$ is one or more atoms forming a ring system with rings B and D and the bond depicted as "-----" in ring B is a single bond; or if $X^1$ is oxygen and either $R^{16}$ or $R^{18}$ is hydroxyl in general formula (VII), then $R^6$ is other than oxygen, amino, or alkyl amino, or at least one of $R^3$, $R^8$ or $R^{15}$ is other than hydrogen, or $R^{13}$ is one or more atoms forming a ring system with rings B and D and the bond depicted as "-----" in ring B is a single bond.

In some embodiments, $X^1$ is oxygen. In certain embodiments, $R^{13}$ is —COO— and forms a lactone ring. In some embodiments, the compound comprises at least one halogen atom positioned adjacent to an ionizable moiety.

In some embodiments, compounds according to general formulas (III)-(XI) have emission spectrum maxima at a wavelength greater than or equal to 700 nm, or greater than or equal to 750 nm. In certain embodiments, the compounds have a Stokes shift greater than or equal to 80 nm, such as greater than or equal to 100 nm.

In some embodiments, the compounds have a chemical structure according to general formula (III) where $R^1$, $R^2$, $R^5$, $R^7$, and $R^8$, are hydrogen or halogen; $R^6$ is oxygen, imino, iminium, lower alkyl iminium, or —$NHR^c$ where $R^c$ is as defined above, and $R^9$-$R^{12}$ independently are hydrogen, amino, lower alkyl, carboxyl, or —$SO_3H$. In certain embodiments, the compounds have a chemical structure according to general formula (III) where $R^1$, $R^2$, $R^5$, $R^7$-$R^{12}$, and $R^{15}$-$R^{17}$ are hydrogen, $R^6$ is iminium or —$NHR^c$ where $R^c$ is as defined above, $R^{13}$ is —$COOR^{14}$ where $R^{14}$ is hydrogen or lower alkyl, and $R^{16}$ and $R^{18}$ independently are amino or —$NHR^c$ where $R^c$ is as defined above.

In some embodiments, the compounds have a chemical structure according to general formula (IV), (IX), or (X) where $X^1$ is oxygen and $R^{16}$ and $R^{18}$ independently are halogen, hydrogen, hydroxyl, thiol, amino, alkyl amino, alkoxy, or —$NHR^c$ where $R^c$ is as defined above, and at least one of $R^{16}$ and $R^{18}$ is other than hydrogen. In certain embodiments, the compounds have a chemical structure according to general formula (IV) where $X^1$ is oxygen and $R^{19}$ and $R^{21}$ independently are hydroxyl, thiol, oxygen, imino, iminium, alkyl imino, alkyl iminium, amino, or alkyl amino, and at least one of $R^{19}$ and $R^{21}$ is other than hydrogen; in particular embodiments, $R^{18}$ is halogen, hydroxyl, thiol, amino, alkyl amino, alkoxy, or —$NHR^c$ where $R^c$ is as defined above. In some embodiments, the compounds have a chemical structure according to general formula (VI) where $R^{17}$ is halogen, hydroxyl, thiol, amino, alkyl amino, or —$NHR^c$ where $R^c$ is as defined above, and $R^{20}$ is oxygen, sulfur, imino, iminium, alkyl iminium, or —$NHR^c$ where $R^c$ is as defined above. In some embodiments, the compounds have a chemical structure according to general formula (III) where $X^1$ is oxygen and $R^6$ and $R^{16}$ are —$NHR^c$ or general formula (IV) where $X^1$ is oxygen and $R^{16}$ and $R^{21}$ are —$NHR^c$ where $R^c$ is as defined above.

In particular embodiments, the compound has a chemical structure selected from

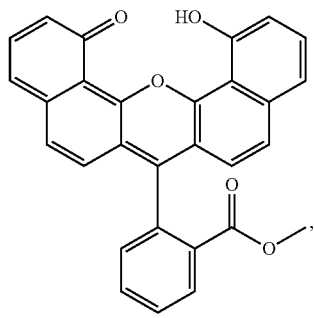

7
-continued
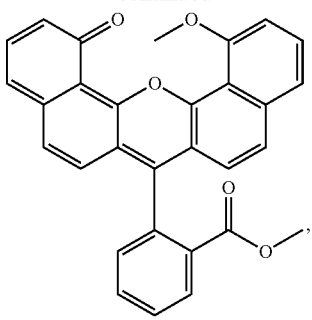
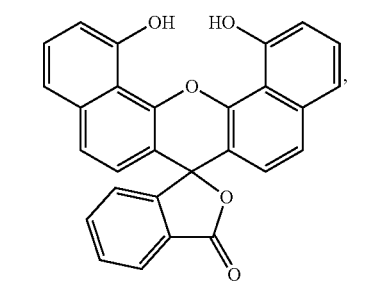
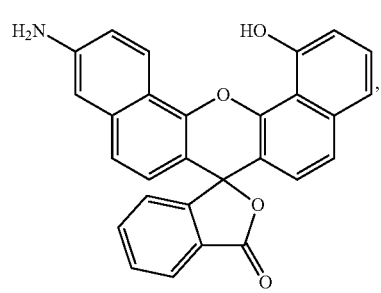
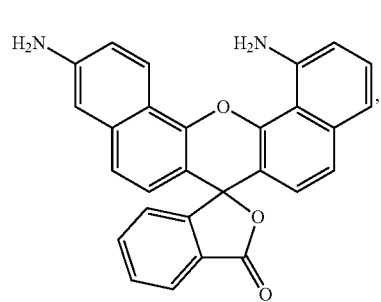
8
-continued
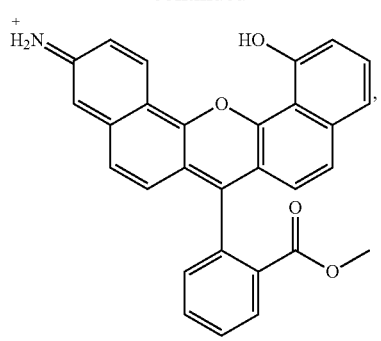
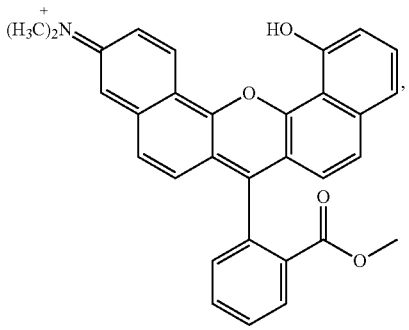
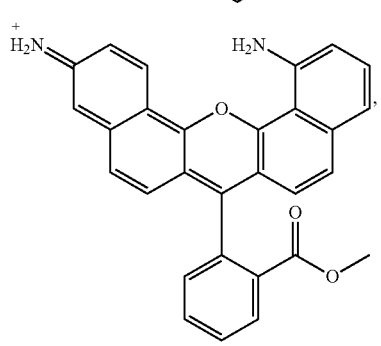
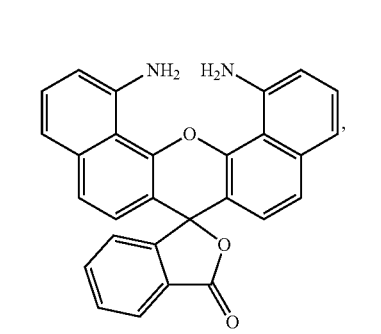
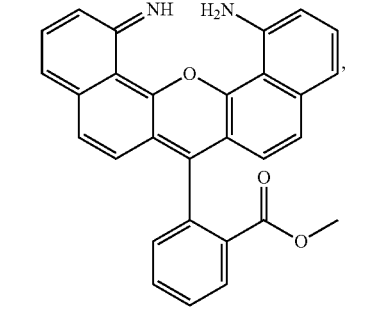

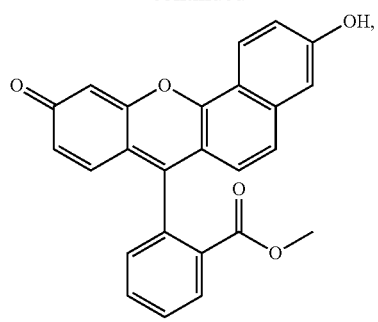
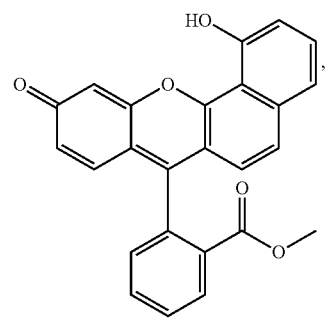
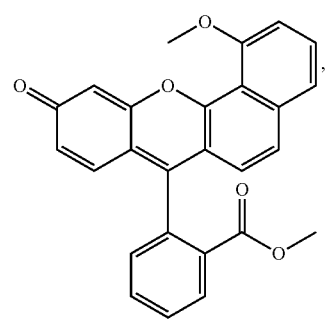
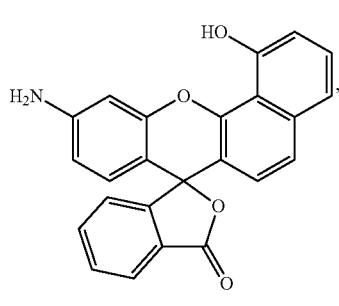
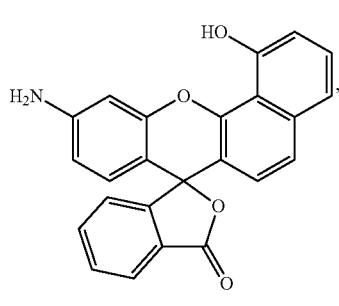
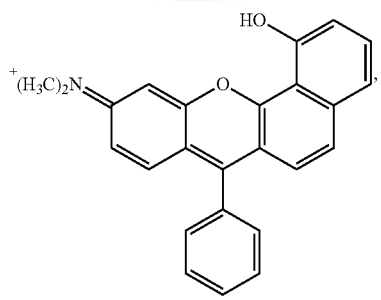
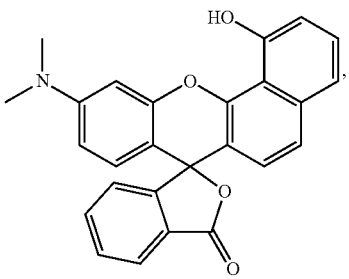
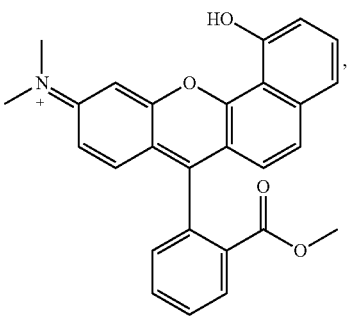
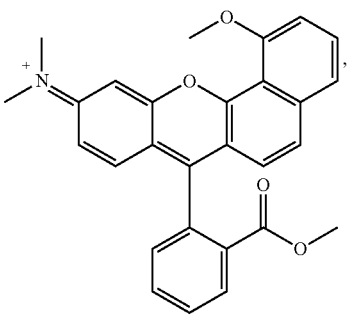
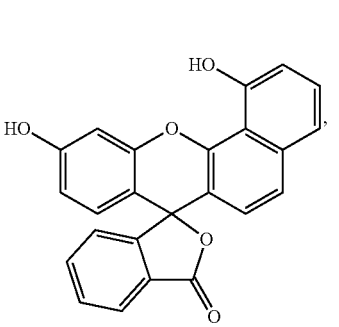

-continued

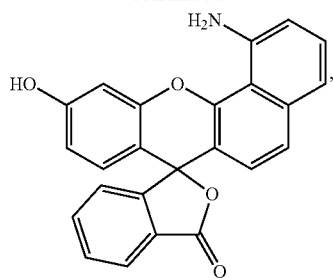

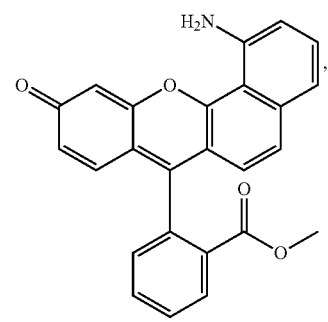

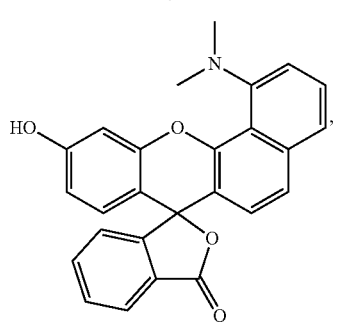

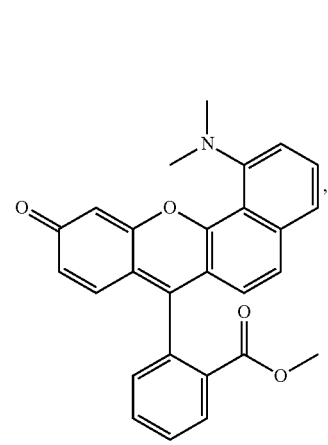

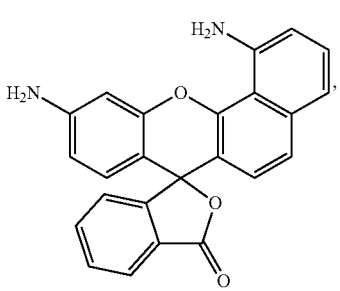

-continued

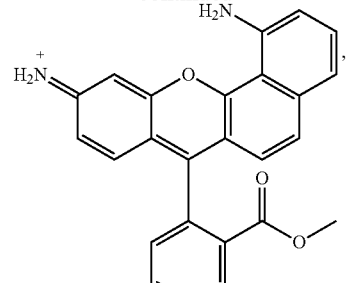

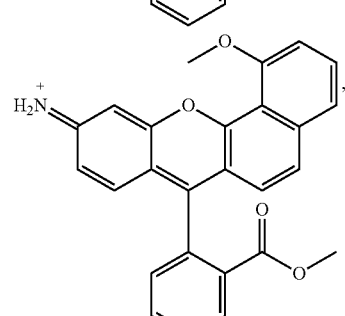

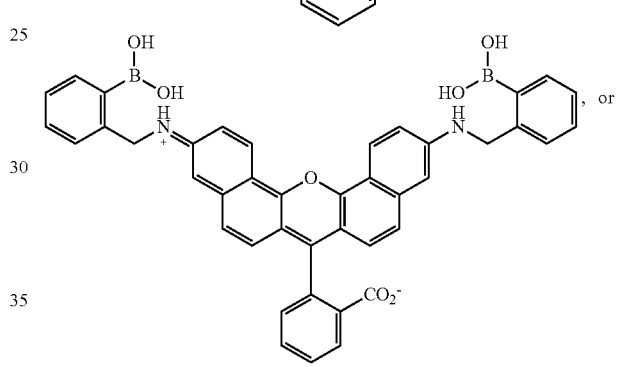

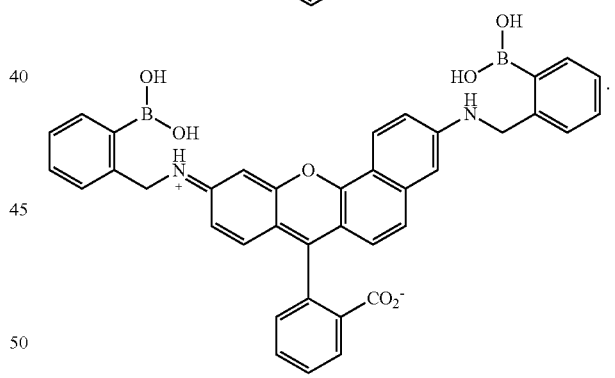

In some embodiments, a method for using the disclosed compounds to detect analytes in biological fluid includes combining a compound having a structure according to any one of general formulas (III)-(XI) with a biological fluid to form a solution, exposing the solution to a light source, and detecting the analyte by detecting fluorescence from the compound. In certain embodiments, the light source has a wavelength in the range of 190 nm to 850 nm. Detecting fluorescence from the compound may include detecting fluorescence at a wavelength corresponding to an emission spectrum maximum of the compound. In certain embodiments, the compound has an emission spectrum maximum at a wavelength greater than or equal to 700 nm, or greater than or equal to 750 nm. In particular embodiments, the analyte is quantitated by measuring an amount of fluorescence from the compound at a wavelength corresponding to an emission spectrum maximum of the compound.

In some embodiments, the analyte is detected in a biological fluid comprising blood or urine. In certain embodiments, the analyte is cysteine, homocysteine, glutathione, succinyl-5-amino-4-imidazolecarboxamide riboside, succinyladenosine, or a combination thereof. In some embodiments, when detecting glutathione, succinyl-5-amino-4-imidazolecarboxamide riboside, succinyladenosine, or a combination thereof, the compound may have a chemical structure according to general formula (VI) where $R^1$, $R^4$, $R^5$ and $R^8$ independently are hydrogen, hydroxyl, thiol, lower alkyl, carboxyalkyl, amino, substituted amino, alkoxy, or halogen; and $R^{19}$-$R^{22}$ independently are hydrogen, hydroxyl, thiol, halogen, oxygen, imino, iminium, alkyl imino, alkyl iminium, amino, alkyl amino, or —$NHR^c$ where $R^c$ is as defined above. For example, when the analyte is glutathione, $R^{17}$ may be hydroxyl, amino, or alkyl amino, and $R^{20}$ may be oxygen, hydroxyl, amino, alkyl amino, imino, or alkyl iminium. In certain embodiments, when the analyte is glutathione, the compound may be

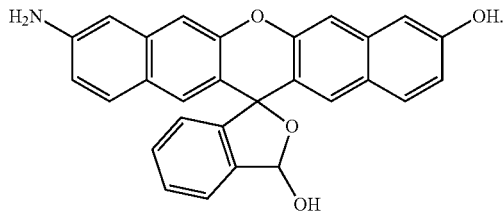 [SMILES: Nc1ccc2cc3c(cc2c1)Oc1cc2cc(O)ccc2cc1C31OC(O)c2ccccc21]

When the analyte is succinyl-5-amino-4-imidazolecarboxamide riboside, succinyladenosine, or a combination thereof, at least one of $R^{17}$ and $R^{20}$ may be —$NHR^c$. In such embodiments, $R^{13}$ typically is —$COOR^{14}$ where $R^{14}$ is hydrogen or lower alkyl, and the linker is at $R^9$, $R^{10}$, $R^{11}$, or $R^{12}$. In some embodiments, the analyte is succinyl-5-amino-4-imidazolecarboxamide riboside, succinyladenosine, or a combination thereof, and the compound comprises at least one fluorophore according to general formula (III) where $X^1$ is oxygen and $R^6$ and $R^{16}$ are —$NHR^c$ or general formula (IV) where $X^1$ is oxygen and $R^{16}$ and $R^{21}$ are —$NHR^c$.

Kits for detecting an analyte include at least one of the disclosed compounds, wherein the compound when combined with a sample (e.g., a biological fluid) including the analyte will undergo a change in color, absorbance spectrum, emission spectrum, or a combination thereof compared to the compound in a sample that does not include the analyte. In some embodiments, the kit further includes a buffer solution suitable for effecting a change in the compound's absorbance and/or emission spectrum when the compound and buffer are combined with a sample including the analyte. The kit also may include color comparison chart for evaluating a color change produced by a reaction between the compound and the analyte. In certain embodiments, the kit includes a plurality of disposable containers in which a reaction between the compound and the analyte can be performed. An amount of the compound effective to undergo a detectable change in the color, absorbance spectrum, the emission spectrum, or a combination thereof when reacted with the analyte may be premeasured into the plurality of disposable containers.

The foregoing and other objects, features, and advantages of the invention will become more apparent from the following detailed description, which proceeds with reference to the accompanying figures.

BRIEF DESCRIPTION OF THE DRAWINGS

FIG. 14 is an x-ray structure of one embodiment of the disclosed dyes, compound 14a.

FIG. 29A is absorption and emission spectra of the compound (3.75 µM) in response to 10 mM sugars in DMSO:buffer 1:9; FIG. 29B is fluorescence emission (ex. 580 nm/em. 660 nm) as a function of sugar concentration in DMSO:buffer 1:9; FIG. 29C is absorption and emission spectra of the compound (3.75 µM) in response to 10 mM sugars in DMSO:buffer 1:1; FIG. 29D is fluorescence emission (ex. 580 nm/em. 640 nm) as a function of sugar concentration in DMSO:buffer 1:1. The final pH 7.4 phosphate buffer concentration was 12.5 mM.

FIG. 30A is absorption (630 nm) spectra of the compound (7.5 µM) as a function of sugar concentration in DMSO:buffer 1:9; FIG. 30B is fluorescence (ex. 630/em. 690 nm) spectra of the compound (7.5 µM) as a function of sugar concentration in DMSO:buffer 1:9; FIG. 30C is absorption (640 nm) spectra of the compound (7.5 µM) as a function of sugar concentration in DMSO:buffer 1:1; FIG. 30D is fluorescence (ex. 640/em. 700 nm) spectra of the compound (7.5 µM) as a function of sugar concentration in DMSO:buffer 1:1; the final pH 7.4 phosphate buffer concentration was 12.5 mM.

DETAILED DESCRIPTION

Figure 1:
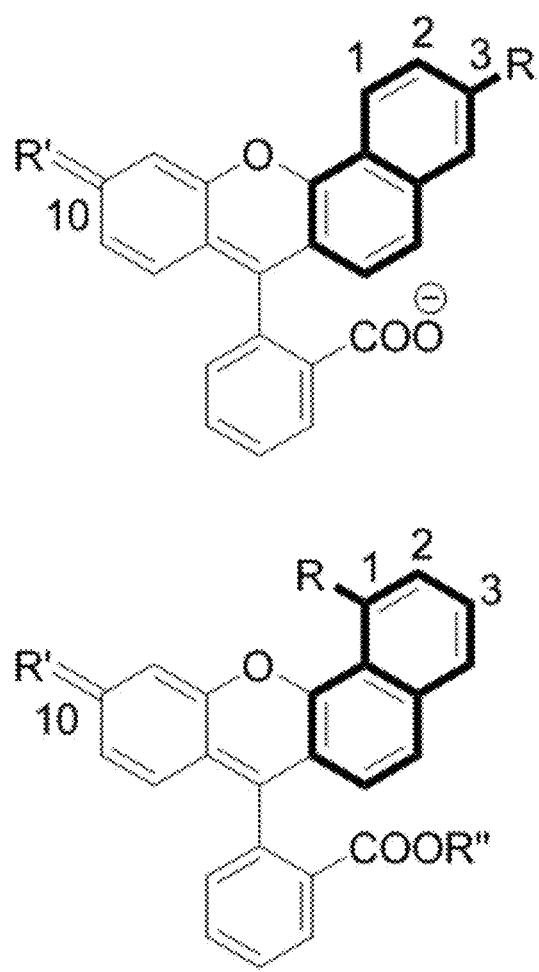
FIG. 1 includes general chemical structures of type [c] annulated xanthenes with substituents at carbon-1 or carbon-3 of the annulated ring, where R is —OH or —$N(CH_3)_2$, R' is oxygen or —$N(CH_3)_2^+$, and R" is hydrogen or lower alkyl.

Disclosed herein are embodiments of novel near-infrared (NIR) dyes based on xanthene architectures. Xanthene dyes such as fluorescein and rhodamine derivatives are commonly used fluorescent dyes due to their bright fluorescence and compatibility with common laser line excitations. Fluorescein emission generally falls in the green or yellow spectral region while some rhodamines exhibit red emission (>600 nm).

Embodiments of the disclosed NIR dyes form a unique series of xanthene-based regioisomeric naphthofluorone dyes exhibiting a combination of desirable characteristics, including (i) relatively low molecular weight, (ii) aqueous solubility, and/or (iii) dual excitation and emission from their fluorescent neutral and anionic forms. Systematic changes in the regiochemistry of benzannulation and the ionizable moieties afford (iv) tunable deep-red to NIR emission and (v) enhanced Stokes shifts.

I. Terms and Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of ingredients, properties such as molecular weight, percentages, and so forth, as used in the specification or claims are to be understood as being modified by the term "about." Unless otherwise indicated, non-numerical properties such as amorphous, crystalline, homogeneous, and so forth as used in the specification or claims are to be understood as being modified by the term "substantially," meaning to a great extent or degree. Accordingly, unless otherwise indicated, implicitly or explicitly, the numerical parameters and/or non-numerical properties set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). Definitions of common terms in molecular biology may be found in Benjamin Lewin, *Genes VII*, published by Oxford University Press, 2000 (ISBN 019879276X); Kendrew et al. (eds.), *The Encyclopedia of*

Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar references.

In order to facilitate review of the various embodiments of the disclosure, the following explanations of specific terms are provided:

Absorbance is the retention by a compound or substance of certain wavelengths of radiation incident upon it; a measure of the amount of light at a particular wavelength absorbed as the light passes through a compound or substance, or through a solution of a compound or substance.

Alkyl refers to a hydrocarbon group having a saturated carbon chain. The chain may be cyclic, branched or unbranched. The term lower alkyl means the chain includes 1-10 carbon atoms.

An analogue or derivative is a molecule that differs in chemical structure from a parent compound, for example a homologue (differing by an increment in the chemical structure, such as a difference in the length of an alkyl chain), a molecular fragment, a structure that differs by one or more functional groups, a change in ionization. Structural analogues are often found using quantitative structure activity relationships (QSAR), with techniques such as those disclosed in Remington (The Science and Practice of Pharmacology, 19th Edition (1995), chapter 28).

Annelation/annulation is a chemical reaction in which one cyclic or ring structure is added to another to form a polycyclic, or annulated, compound. Annulation can be categorized as type [a], type [b], or type [c], depending on the position of the newly added ring. Type [a] refers to "down annulation," type [b] refers to "across annulation," and type [c] refers to "up annulation," as shown below:

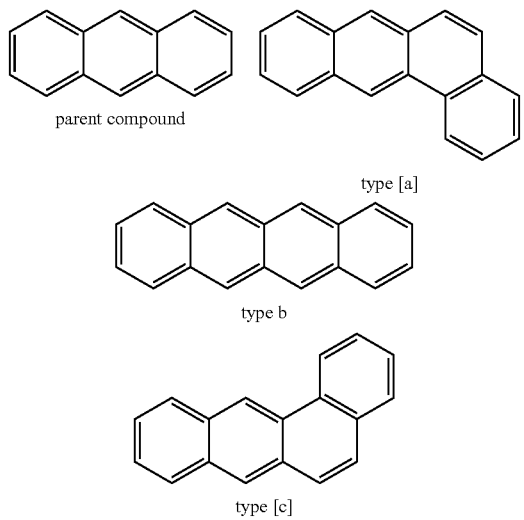

As used herein, the term "annulated" refers to having or consisting of rings or ringlike segments. The term "benzannulated" refers to derivatives of cyclic compounds (usually aromatic), which are fused to a benzene ring. Examples of benzannulated compounds include, inter alia, benzopyrenes, quinolines, naphthoquinones, naphthofluoresceins, rhodamines, and xanthenes.

Aromatic or aryl compounds typically are unsaturated, cyclic hydrocarbons having alternate single and double bonds. Benzene, a 6-carbon ring containing three double bonds, is a typical aromatic compound.

A bathochromic shift is a change of spectral band position in the absorption, reflectance, transmittance, or emission spectrum of a molecule to a longer wavelength, or lower frequency. A bathochromic shift commonly is referred to as a "red shift." Bathochromic shifts can occur in the spectra of a series of structurally related molecules with different substitutions and/or substitution patterns. A change in environment, e.g., solvent polarity, also can produce a bathochromic shift.

Coumarin: A benzopyrone having the following general structure:

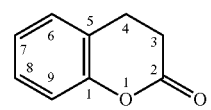

As used herein, "substituted coumarin" refers to a coumarin including one or more substituents. Suitable substituents may include substituted or unsubstituted lower alkyl, substituted or unsubstituted lower alkoxy, lower alkyl carbonyl, substituted or unsubstituted amino, halo, and hydroxyl groups. In some embodiments, the coumarin is substituted at the 3- and/or 7-position with, for example, a lower alkyl, lower alkyl carbonyl, lower alkoxy, amino or substituted amino group.

Emission or an emission signal refers to the light of a particular wavelength generated from a source. In particular examples, an emission signal is emitted from a fluorophore after the fluorophore absorbs light at its excitation wavelength(s).

Excitation or an excitation signal refers to the light of a particular wavelength necessary and/or sufficient to excite an electron transition to a higher energy level. In particular examples, an excitation signal is the light of a particular wavelength necessary and/or sufficient to excite a fluorophore to a state such that the fluorophore will emit a different (such as a longer) wavelength of light than the wavelength of light from the excitation signal.

Fluorescence is the emission of visible radiation by an atom or molecule passing from a higher to a lower electronic state, wherein the time interval between absorption and emission of energy is $10^{-8}$ to $10^{-3}$ second. As used herein, fluorescence occurs when the atom or molecule absorbs energy from an excitation source (e.g., a lamp producing light within a wavelength range of 190-850 nm) and then emits the energy as visible and/or near-infrared radiation.

A fluorogen is a compound capable of fluorescence.

A fluorophore is the functional group, or portion, of a molecule that causes the molecule to fluoresce when exposed to an excitation source. The term "fluorophore" also is used to refer to fluorescent compounds used as dyes to mark proteins with a fluorescent label.

A functional group is a specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), disulfide.

GSH: Glutathione.

Heteroaryl compounds are aromatic compounds having at least one heteroatom, i.e., one or more carbon atoms in the ring has been replaced with an atom having at least one lone pair of electrons, typically nitrogen, oxygen, or sulfur.

Imino refers to a functional group having the formula =NH.

Iminium refers to a protonated or substituted imine, e.g., $=NH_2^+$ or $(=NR_AR_B)^+$ where $R_A$ and $R_B$ represent alkyl or substituted alkyl groups. As used herein, $(=NR_AR_B)^+$ is referred to as an alkyl iminium group.

MIP: Molecule-imprinted polymer.

Near infrared (NIR) is a region of the electromagnetic spectrum between the visible region and the infrared region. There is no set definition for the boundaries of the near-infrared region, but definitions include the wavelength ranges from 650-2500 nm, 750-2500 nm, 780-2500 nm, 800-2500 nm, 700-1400 nm, or 780-3000 nm. As used herein, NIR typically refers to the wavelength region of 700-1400 nm.

A rhodol is a structural hybrid of fluorescein and a rhodamine. Rhodamines are a family of related fluorone dyes. The structures of fluorescein, a rhodamine, and two rhodol analogues are shown below.

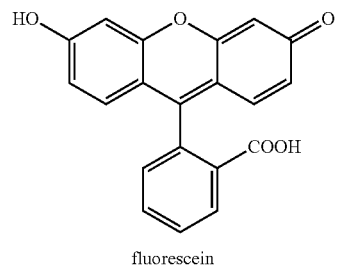

fluorescein

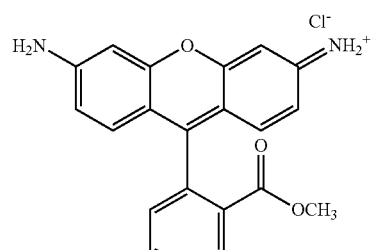

Rhodamine 123

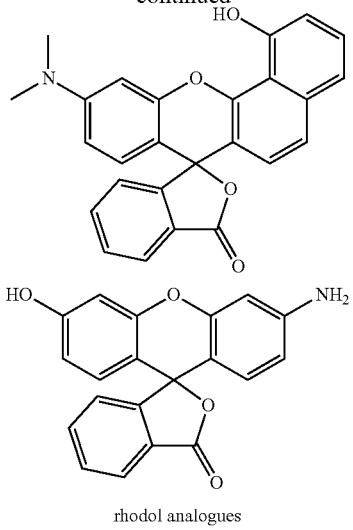

rhodol analogues

SNAFL: Seminaphthofluorescein
SNAFR: Seminaphthofluorone
SNARF: Seminaphthorhodafluor Stokes shift refers to the difference (in wavelength or frequency units) between absorbance spectrum maximum and the emission spectrum maximum of the same electronic transition. Typically, the wavelength of maximum fluorescence emission is longer than that of the exciting radiation, i.e., the wavelength of maximum absorbance.

Xanthene is an organic heterocyclic compound with the formula $C_{13}H_{10}O$.

xanthene

Xanthene derivatives are referred to as xanthenes, and include fluorescein, rhodamine, and derivatives thereof.

II. Overview Of Representative Embodiments

Embodiments of compounds having emission spectrum maxima in the near-infrared region (near-infrared (NIR) dyes) and that selectively detect analytes in buffered solutions and/or biological media are disclosed. Some embodiments of the disclosed compounds exhibit large bathochromic shifts and/or enhanced Stokes shifts compared to currently available NIR dyes.

Some embodiments of the disclosed compounds have a structure according to general formulas (III)-(XI) as described herein. In some embodiments, $X^1$ is oxygen. In any or all of the above embodiments, $R^{13}$ may be —COO— and form a lactone ring. In any or all of the above embodiments, the compound may comprise at least one halogen atom positioned adjacent to an ionizable moiety.

In any or all of the above embodiments, the compound may have an emission spectrum maximum at a wavelength greater than or equal to 700 nm, such as greater than or equal to 750 nm. In any or all of the above embodiments, the compound may have a Stokes shift greater than or equal to 80 nm, such as greater than or equal to 100 nm.

In some embodiments, the compound has a chemical structure according to structure (III) where $R^6$ is amino or alkyl amino, and at least one of $R^{16}$ or $R^{18}$ is hydroxyl, amino, or alkyl amino. In other embodiments, the compound has a chemical structure according to structure (III), where $R^1$, $R^2$, $R^5$, $R^7$, and $R^8$ are hydrogen or halogen; $R^6$ is oxygen, imino, iminium, lower alkyl iminium, or —$NHR^c$, and $R^9$-$R^{12}$ independently are hydrogen, amino, lower alkyl, carboxyl, or —$SO_3H$. In still other embodiments, the compound has a chemical structure according to structure (III) where $R^1$, $R^2$, $R^5$, $R^7$-$R^{12}$, and $R^{15}$-$R^{17}$ are hydrogen, $R^6$ is iminium, $R^{13}$ is —$COOR^{14}$ where $R^{14}$ is hydrogen or lower alkyl, and $R^{18}$ is amino.

In some embodiments, the compound has a chemical structure according to structure (IV), (IX), or (X) where $X^1$ is oxygen and $R^{18}$ is halogen, hydroxyl, thiol, amino, alkyl amino, or alkoxy. In some embodiments, the compound has a chemical structure according to structure (IV) where $X^1$ is oxygen and $R^{19}$ is hydroxyl, thiol, oxygen, imino, iminium, alkyl imino, alkyl iminium, amino, or alkyl amino; in certain embodiments, $R^{18}$ is halogen, hydroxyl, thiol, amino, alkyl amino, or alkoxy.

In some embodiments, the compound has a chemical structure according to structure (VI) where $R^{17}$ is halogen, hydroxyl, thiol, amino, alkyl amino, or —$NHR^c$, and $R^{20}$ is oxygen, sulfur, imino, iminium, alkyl iminium, or —$NHR^c$.

Embodiments of a method for selectively detecting an analyte in a biological fluid include combining a compound according to any or all of the above embodiments with a biological fluid to form a solution, exposing the solution to a light source, and detecting the analyte by detecting fluorescence from the compound. In some embodiments, the light source has a wavelength in the range of 190 nm to 850 nm. In any or all of the above embodiments, the biological fluid may comprise blood or urine.

In any or all of the above embodiments, detecting fluorescence from the compound may include detecting fluorescence at a wavelength corresponding to an emission spectrum maximum of the compound. In some embodiments, the compound has an emission spectrum maximum at a wavelength greater than or equal to 700 nm, such as greater than or equal to 750 nm. In some embodiments, the analyte is quantitated by measuring an amount of fluorescence from the compound at a wavelength corresponding to an emission spectrum maximum of the compound.

In any or all of the above embodiments, the analyte may be cysteine, homocysteine, glutathione, succinyl-5-amino-4-imidazolecarboxamide riboside, succinyladenosine, or a combination thereof. In some embodiments, the compound has a chemical structure according to general structure (VI) where $R^1$, $R^4$, $R^5$ and $R^8$ independently are hydrogen, hydroxyl, thiol, lower alkyl, carboxyalkyl, amino, substituted amino, alkoxy, or halogen; and $R^{19}$-$R^{22}$ independently are hydrogen, hydroxyl, thiol, halogen, oxygen, imino, iminium, alkyl imino, alkyl iminium, amino, alkyl amino, or —$NHR^c$.

In some embodiments, the analyte is glutathione, and the compound has a structure according to general structure (VI) as described above where $R^{17}$ is hydroxyl, amino, or alkyl amino, and $R^{20}$ is oxygen, hydroxyl, amino, alkyl amino, imino, or alkyl iminium. In one embodiment, the compound is

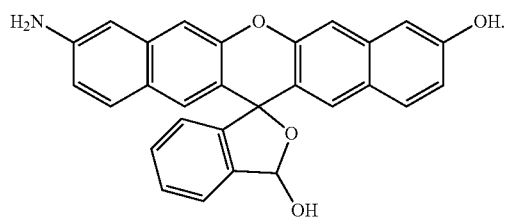 [SMILES: Nc1ccc2cc3c(cc2c1)Oc1cc2cc(O)ccc2cc1C31OC(O)c2ccccc21]

In some embodiments, the analyte is succinyl-5-amino-4-imidazole-carboxamide riboside, succinyladenosine, or a combination thereof, and the compound has a structure according to general structure (VI) as described above where at least one of $R^{17}$ and $R^{20}$ is —$NHR^c$, and $R^{13}$ is —$COOR^{14}$ where $R^{14}$ is hydrogen or lower alkyl. In some embodiments, the analyte is succinyl-5-amino-4-imidazolecarboxamide riboside, succinyladenosine, or a combination thereof, and the compound comprises at least one fluorophore according to general formula (III) where $X^1$ is oxygen and $R^6$ and $R^{16}$ are —$NHR^c$ or general formula (IV) where $X^1$ is oxygen and $R^{16}$ and $R^{21}$ are —$NHR^c$.

Embodiments of a kit for detecting an analyte include at least one compound according to any or all of the above embodiments, wherein the compound when combined with a sample comprising the analyte will undergo a change in its absorbance spectrum and/or emission spectrum compared to the compound in a sample that does not comprise the analyte. In some embodiments, the sample is a biological fluid. In any or all of the above embodiments, the kit may include at least one buffer solution in which the compound when combined with a sample comprising the analyte will undergo a change in its absorbance spectrum and/or emission spectrum compared to the compound combined with the buffer solution and a sample that does not comprise the analyte. In any or all of the above embodiments, the analyte may be glutathione, cysteine, homocysteine, succinyl-5-amino-4-imidazolecarboxamide riboside, succinyladenosine, or a combination of succinyl-5-amino-4-imidazolecarboxamide riboside and succinyladenosine. In some embodiments, the compound in the kit has a chemical structure according to general structure (VI) as described above. In some embodiments, the compound in the kit has a chemical structure according to general structure (III) as described above where $X^1$ is oxygen and $R^6$ and $R^{16}$ are —$NHR^c$ or general structure (IV) where $X^1$ is oxygen and $R^{16}$ and $R^{21}$ are —$NHR^c$.

In any or all of the above embodiments, the kit may include a color comparison chart for evaluating a color change produced by a reaction between the compound and the analyte. In any or all of the above embodiments, the kit may include a plurality of disposable containers in which a reaction between the compound and the analyte can be performed. In some embodiments, an amount of the compound effective to undergo a detectable change in the absorbance spectrum, the emission spectrum, or both when reacted with the analyte is premeasured into the plurality of disposable containers.

III. Near-Infrared Dyes

Embodiments of the disclosed near-infrared (NIR) dyes are based on an annulated xanthene architecture. Some embodiments of the disclosed NIR dyes exhibit significant bathochromic shifts and enhanced Stokes shifts compared to structurally related analogues. In some embodiments, the NIR dyes are benzannulated xanthenes with single or double annulation. The annulation may be type [a]—down, type

[b]—across, or type [c]—up. At least some embodiments of the singly and doubly annulated NIR dyes have substantially red-shifted absorbance and emission spectra compared to commercially available NIR dyes. In some embodiments, the spectra are red shifted by at least 100 nm. In particular, some embodiments of the disclosed NIR dyes have an emission maximum greater than 700 nm. In certain embodiments, emission maxima are well into the near-infrared region, e.g., greater than 700 nm, greater than 750 nm, and even greater than 780 nm. In comparison, some known annulated xanthenes have emission maxima near 560 nm (fully benzannulated dibenzofluorescein), 630 nm (SNA-FLs), 650 nm (SNARFs), 670 nm (naphthofluorescein), or 650-675 nm (dibenzorhodamines). In some embodiments, the absorption maxima are greater than 600 nm, greater than 650 nm, greater than 675 nm, and even greater than 800 nm.

Some embodiments of the NIR dyes also exhibit an enhanced Stokes shift compared to known long-wavelength xanthenes. In certain embodiments, the Stokes shift (difference between absorbance spectrum maximum and the emission spectrum maximum of the same electronic transition) is greater than 50 nm, greater than 80 nm, greater than 100 nm, or greater than 150 nm, such as 50-200 nm, 50-150 nm, 80-150 nm, 90-170 nm, 100-150 nm, or 100-200 nm. A large Stokes shift is advantageous since it facilitates use of relatively broad-band light sources, such as light-emitting diodes, with minimal scattered light interference from the light source at the emission wavelength(s) measured.

A. Structures

In some embodiments, the NIR dyes have a structure according to general formula I.

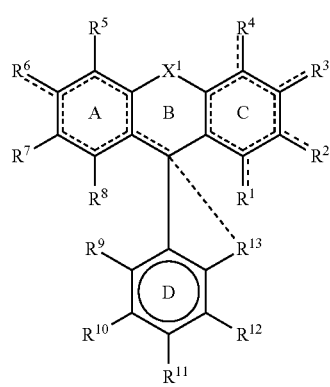

(I)

In general formula I, each bond depicted as "-----" is a single or double bond as needed to satisfy valence requirements; $X^1$ is O, S, Se, $Si(CH_3)_2$, $Ge(CH_3)_2$, $Sn(CH_3)_2$, $CH_2$, $C(CH_3)_2$ or NH. $R^1$, $R^2$, and $R^4$ independently are hydrogen, hydroxyl, oxygen, thiol, lower alkyl, carboxyalkyl, amino, substituted amino, alkoxy, halogen, or —$NHR^c$ where $R^c$ is

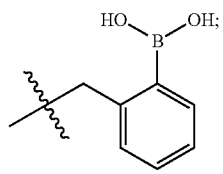 [SMILES: *Cc1ccccc1B(O)O]

$R^5$, $R^7$, and $R^8$ independently are hydrogen, hydroxyl, thiol, lower alkyl, carboxyalkyl, amino, substituted amino, alkoxy, or halogen; $R^3$ and $R^6$ independently are hydrogen, hydroxyl, halogen, oxygen, sulfur, thiol, amino, alkyl amino, imino, iminium, alkyl imino, alkyl iminium, cycloalkyl imino, or —$NHR^c$ where $R^c$ is as defined above; and at least one of $R^1$ and $R^2$, $R^2$ and $R^3$, $R^3$ and $R^4$, $R^5$ and $R^6$, $R^6$ and $R^7$, and/or $R^7$ and $R^8$ together form a substituted or unsubstituted cycloalkyl or aryl. $R^9$-$R^{12}$ independently are hydrogen, alkyl, acyl, carboxyl, nitro, amino, alkyl amino, or —$SO_3H$. $R^{13}$ is hydrogen, hydroxyl, lower alkyl, lower alkoxy, —$SO_3H$ or —$COOR^{14}$ where $R^{14}$ is hydrogen or lower alkyl and the bond depicted as "-----" in ring B is a double bond, or $R^{13}$ is one or more atoms forming a ring system with rings B and D and the bond depicted as "-----" in ring B is a single bond. In some embodiments, $R^{13}$ is —COO— and forms a lactone ring as shown in general formula II.

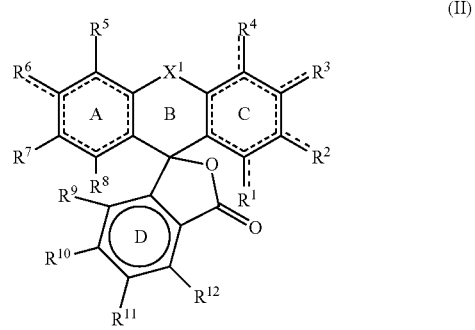

(II)

In some embodiments, $R^3$ and $R^4$ and/or $R^5$ and $R^6$ together form an aryl or substituted aryl ring as shown in general formulas III and IV

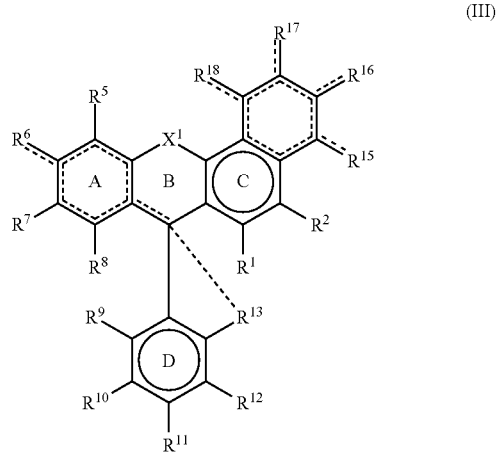

(III)

-continued

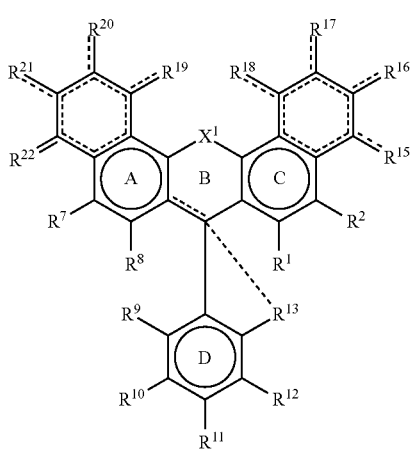

(IV)

where each bond depicted as "-----" is a single or double bond as needed to satisfy valence requirements. $R^1$-$R^{14}$ and $X^1$ are as defined for general formulas (I) and (II). $R^{15}$-$R^{22}$ independently are hydrogen, halogen, hydroxyl, oxygen, thiol, amino, alkyl amino, alkoxy, such as lower alkoxy, sulfur, imino, iminium, alkyl imino, alkyl iminium, or —$NHR^c$ where $R^c$ is as defined above. $R^{19}$, $R^{20}$, $R^{21}$, and $R^{22}$ independently are hydrogen, hydroxyl, thiol, halogen, oxygen, amino, alkyl amino, or —$NHR^c$ where $R^c$ is as defined above. In certain embodiments, $X^1$ is oxygen, $R^1$, $R^2$, $R^5$, $R^7$ and $R^8$ independently are hydrogen or halogen; $R^6$ is oxygen, imino, iminium, lower alkyl iminium, or —$NHR^c$ where $R^c$ is as defined above; $R^9$-$R^{12}$ independently are hydrogen, amino, lower alkyl, carboxyl, or —$SO_3H$; $R^{15}$, $R^{17}$, $R^{20}$, and $R^{22}$ are hydrogen; $R^{13}$ is hydrogen, lower alkyl, lower alkoxy, —$SO_3H$, —$COOR^{14}$ where $R^{14}$ is hydrogen or lower alkyl and the bond depicted as "-----" in ring B is a double bond, or $R^{13}$ is one or more atoms forming a ring system with rings B and D and the bond depicted as "-----" in ring B is a single bond; $R^{16}$ and $R^{18}$ independently are hydrogen, hydroxyl, oxygen, lower alkoxy, amino, alkyl amino, or —$NHR^c$ where $R^c$ is as defined above, and at least one of $R^{16}$ and $R^{18}$ is other than hydrogen; $R^{19}$ and $R^{21}$ independently are oxygen, imino, iminium, lower alkyl iminium, or —$NHR^c$ where $R^c$ is as defined above, and at least one of $R^{19}$ and $R^{21}$ is other than hydrogen. In particular embodiments, $X^1$ is oxygen, $R^1$, $R^2$, $R^5$, $R^8$, $R^9$, $R^{12}$, $R^{15}$, $R^{17}$, $R^{20}$, and $R^{22}$ are hydrogen; $R^6$ is oxygen, imino, iminium, lower alkyl iminium, or —$NHR^c$ where $R^c$ is as defined above; $R^7$ is hydrogen or halogen; $R^{10}$ and $R^{11}$ independently are hydrogen, amino, lower alkyl, carboxyl, or —$SO_3H$; $R^{13}$ is hydrogen, lower alkyl, lower alkoxy, —$SO_3H$, or —$COOR^{14}$ where $R^{14}$ is hydrogen or lower alkyl and the bond depicted as "-----" in ring B is a double bond, or $R^{13}$ is one or more atoms forming a ring system with rings B and D and the bond depicted as "-----" in ring B is a single bond; $R^{16}$ and $R^{18}$ independently are hydrogen, hydroxyl, oxygen, lower alkoxy, amino, alkyl amino, or —$NHR^c$ where $R^c$ is as defined above, and at least one of $R^{16}$ and $R^{18}$ is other than hydrogen; $R^{19}$ is hydrogen, hydroxyl, oxygen, imino, iminium, or lower alkyl iminium; $R^{21}$ is hydrogen, oxygen, or —$NHR^c$ where $R^c$ is as defined above, and at least one of $R^{19}$ and $R^{21}$ is other than hydrogen. In certain embodiments, if $X^1$ is oxygen in structure III, then $R^6$ is other than oxygen or alkyl amino, or $R^{13}$ is other than one or more atoms forming a ring system with rings B and D, or $R^{16}$ is other than hydroxyl or hydrogen, or $R^{18}$ is other than hydroxyl or hydrogen, or at least one of $R^1$, $R^2$, $R^5$, $R^7$, $R^8$, $R^9$, $R^{10}$, $R^{11}$, $R^{12}$, or $R^{13}$ is other than hydrogen. In certain embodiments, if $X^1$ is oxygen, sulfur, $CH_2$, or NH in structure IV, then at least one of $R^1$, $R^2$, $R^7$-$R^{13}$, or $R^{15}$-$R^{22}$ is other than hydrogen, hydroxyl, halogen, lower alkyl, amino, or thiol, or $R^{13}$ is one or more atoms forming a ring system with rings B and D and the bond depicted as "-----" in ring B is a single bond. Representative compounds according to general formulas III and IV are shown in Table 1.

TABLE 1

| Cpd | $R^{6*}$ | $R^7$ | $R^{10}$ | $R^{11}$ | $R^{13}$ | $R^{16}$ | $R^{18}$ | $R^{19}$ | $R^{21}$ |
|---|---|---|---|---|---|---|---|---|---|
| 3a | O | H | H | H | —$OCH_3$ | H | —OH | — | — |
| 3b | O | H | —$CH_3$ | H | —$CH_3$ | H | —OH | — | — |
| 3c | O | H | H | —COOH | H | H | —OH | — | — |
| 3d | O | H | H | —$NH_2$ | H | H | —OH | — | — |
| 3e | O | H | H | H | —$SO_3H$ | H | —OH | — | — |
| 3f | O | H | —$SO_3H$ | H | —$SO_3H$ | H | —OH | — | — |
| 3g | O | F | H | H | H | H | —OH | — | — |
| 3h | =NH | H | —$SO_3H$ | H | —$SO_3H$ | H | —$NH_2$ | — | — |
| 3i | =$N(CH_3)_2^+$ | H | H | H | H | H | —OH | — | — |
| 3j | =$N(CH_3)_2^+$ | H | H | H | H | H | —$N(CH_3)_2$ | — | — |
| 3k | =$N(CH_3)_2^+$ | H | —$SO_3H$ | H | —$SO_3H$ | H | —$N(CH_3)_2$ | — | — |
| 4a | — | H | —$CH_3$ | H | —$CH_3$ | H | —OH | =O | H |
| 4b | — | H | —$SO_3H$ | H | —$SO_3H$ | H | —OH | =O | H |
| 4c | — | H | —$CH_3$ | H | —$CH_3$ | H | —$NH_2$ | =NH | H |
| 4d | — | H | —$CH_3$ | H | —$CH_3$ | H | —$N(CH_3)_2$ | =$N(CH_3)_2^+$ | H |
| 4e | — | H | H | —COOH | H | H | —OH | O | H |
| 4f | — | H | H | —COOH | H | H | —$N(CH_3)_2$ | =$N(CH_3)_2^+$ | H |
| 7 | — | H | H | H | —$COO^†$ | H | —OH | —OH | H |
| 7a | — | H | H | H | —$COO^-$ | H | —OH | —OH | H |
| 7b | — | H | H | H | —$COO^-$ | H | —O- | —OH | H |
| 8 | — | H | H | H | —$COOCH_3$ | H | —OH | =O | H |
| 8a | — | H | H | H | —$COOCH_3$ | H | —O- | =O | H |
| 9 | — | H | H | H | —$COOCH_3$ | H | —$OCH_3$ | =O | H |
| 10 | — | H | —$CH_3$ | H | —$CH_3$ | H | —OH | =O | H |
| 11 | — | H | H | —$SO_3H$ | —$SO_3H$ | H | —OH | =O | H |
| 14a | —OH | H | H | H | —COO-† | H | —OH | — | — |
| 14b | —$NH_2$ | H | H | H | —COO-† | H | —OH | — | — |
| 14c | —$NH_2$ | H | H | H | —COO-† | H | —$OCH_3$ | — | — |
| 14d | —$N(CH_3)_2$ | H | H | H | —COO-† | H | —OH | — | — |
| 14e | —$OCH_3$ | H | H | H | —COO-† | H | —OH | — | — |
| 14f | —OH | H | H | H | —COO-† | H | —$NH_2$ | — | — |
| 14g | —OH | H | H | H | —COO-† | H | —$N(CH_3)_2$ | — | — |

TABLE 1-continued

| Cpd | R6* | R7 | R10 | R11 | R13 | R16 | R18 | R19 | R21 |
|---|---|---|---|---|---|---|---|---|---|
| 14h | —NH$_2$ | H | H | H | —COO-† | H | —NH$_2$ | — | — |
| 15a | =O | H | H | H | —COOCH$_3$ | H | —OH | — | — |
| 15b | =NH$_2^+$ | H | H | H | —COOCH$_3$ | H | —OH | — | — |
| 15c | =NH$_2^+$ | H | H | H | —COOCH$_3$ | H | —OCH$_3$ | — | — |
| 15d | =N(CH$_3$)$_2^+$ | H | H | H | —COOCH$_3$ | H | —OH | — | — |
| 15e | =O | H | H | H | —COOCH$_3$ | H | —NH$_2$ | — | — |
| 15f | =O | H | H | H | —COOCH$_3$ | H | —N(CH$_3$)$_2$ | — | — |
| 15g | =NH$_2^+$ | H | H | H | —COOCH$_3$ | H | —NH$_2$ | — | — |
| 15h | =O | H | H | H | —COOCH$_3$ | H | —O$^-$ | — | — |
| 16a | =O | H | H | H | —COOCH$_3$ | H | —OCH$_3$ | — | — |
| 16b | =N(CH$_3$)$_2^+$ | H | H | H | —COOCH$_3$ | H | —OCH$_3$ | — | — |
| 19a | —OH | H | H | H | —COO-† | —OH | H | — | — |
| 20a | =O | H | H | H | —COOCH$_3$ | —OH | H | — | — |
| 20b | =$^+$NH$_2$ | H | H | H | —COOCH$_3$ | —NH$_2$ | H | — | — |
| 20c | =O | H | H | H | —COOCH$_3$ | —O$^-$ | H | — | — |
| 20d | =O | H | H | H | —COOH | —OH | H | — | — |
| 21a | =O | H | H | H | —COOH | —OH | H | — | — |
| 21b | =O | H | H | H | —COO- | —O- | H | — | — |
| 22 | — | H | H | H | —COOCH$_3$ | —OH | H | H | =O |
| 22a | — | H | H | H | —COOH | —OH | H | H | =O |
| 40 | — | H | H | H | —COOCH$_3$ | H | —OH | =O | H |
| 41 | —N(CH$_3$)$_2$ | H | H | H | —COO-† | H | —N(CH$_3$)$_2$ | — | — |
| 42 | =N(CH$_3$)$_2^+$ | H | H | H | —COOCH$_3$ | H | —N(CH$_3$)$_2$ | — | — |
| 50 | =NH$_2^+$ | H | H | H | —COO$^-$ | =NH$_2^+$ | H | — | — |
| 51 | —NHR$^{c+}$ | H | H | H | —COO$^-$ | —NHR$^{c+}$ | H | — | — |
| 52 | — | H | H | H | —COO$^-$ | =NH$_2^+$ | H | H | =NH$_2^+$ |
| 53 | — | H | H | H | —COO$^-$ | —NHR$^{c+}$ | H | H | —NHR$^{c+}$ |

*All R substituents not included in Table 1 are hydrogen and $X^1$ is oxygen.
†$R^{11}$ forms a lactone ring.

In some embodiments, $R^2$ and $R^3$ and/or $R^6$ and $R^7$ together form an aryl or substituted aryl ring as shown in general formulas V and VI

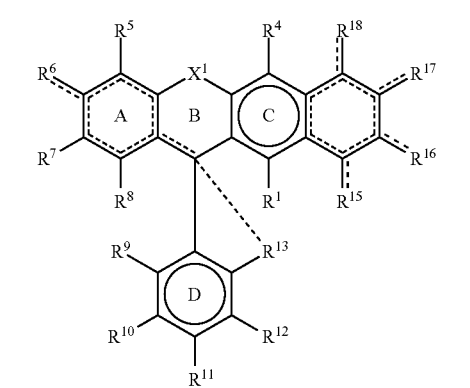

(V)

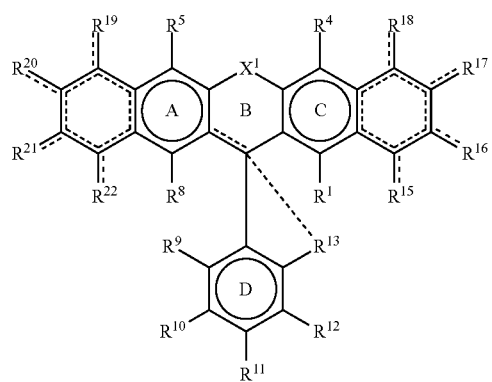

(VI)

where each bond depicted as "-----" is a single or double bond as needed to satisfy valence requirements, and $R^1$-$R^{22}$ and $X^1$ are defined as above. In certain embodiments, $X^1$ is oxygen, $R^1$, $R^4$, $R^5$, $R^7$ and $R^8$ independently are hydrogen or halogen; $R^6$ is oxygen, imino, iminium, lower alkyl iminium, or —NHR$^c$ where $R^c$ is as defined above; $R^9$-$R^{12}$ independently are hydrogen, amino, lower alkyl, carboxyl, or —SO$_3$H; $R^{15}$, $R^{17}$, $R^{19}$, and $R^{22}$ are hydrogen; $R^{13}$ is hydrogen, lower alkyl, lower alkoxy, —SO$_3$H, —COOR$^{14}$ where $R^{14}$ is hydrogen or lower alkyl and the bond depicted as "-----" in ring B is a double bond, or $R^{13}$ is one or more atoms forming a ring system with rings B and D and the bond depicted as "-----" in ring B is a single bond; at least one of $R^{16}$, $R^{17}$ and $R^{18}$ is hydroxyl, oxygen, amino, alkyl amino, or —NHR$^c$ where $R^c$ is as defined above; and at least one of $R^{19}$, $R^{20}$ and $R^{21}$ is oxygen, imino, iminium, lower alkyl iminium, or —NHR$^c$ where $R^c$ is as defined above. In particular embodiments, $X^1$ is oxygen, $R^1$, $R^4$, $R^5$, $R^8$, $R^9$, $R^{12}$, $R^{15}$, $R^{16}$, $R^{18}$, $R^{19}$, $R^{21}$, and $R^{22}$ are hydrogen; $R^6$ is oxygen, imino, iminium, lower alkyl iminium, or —NHR$^c$ where $R^c$ is as defined above; $R^7$ is hydrogen or halogen; $R^{10}$ and $R^{11}$ independently are hydrogen, amino, lower alkyl, carboxyl, or —SO$_3$H; $R^{13}$ is hydrogen, lower alkoxy, —SO$_3$H, or —COOR$^{14}$ where $R^{14}$ is hydrogen or lower alkyl; $R^{17}$ is hydroxyl, oxygen, amino, alkyl amino, or —NHR$^c$ where $R^c$ is as defined above; and $R^{20}$ is oxygen, imino, iminium, lower alkyl iminium, or —NHR$^c$ where $R^c$ is as defined above. In certain embodiments, if $X^1$ is oxygen and $R^{15}$ or $R^{17}$ is hydroxyl in structure V, then $R^6$ is other than oxygen, amino, or alkyl amino, or at least one of $R^1$, $R^8$, or $R^{18}$ is other than hydrogen, or $R^{13}$ is one or more atoms forming a ring system with rings B and D and the bond depicted as "-----" in ring B is a single bond. Representative compounds according to general formulas V and VI are shown in Table 2.

TABLE 2

| Cpd | R6* | R7 | R10 | R11 | R13 | R17 | R20 |
|---|---|---|---|---|---|---|---|
| 2a | O | H | H | H | —OCH$_3$ | —OH | — |
| 2b | O | H | —CH$_3$ | H | —CH$_3$ | —OH | — |
| 2c | O | H | H | —COOH | H | —OH | — |
| 2d | O | H | H | —NH$_2$ | H | —OH | — |
| 2e | O | H | H | H | —SO$_3$H | —OH | — |
| 2f | O | H | —SO$_3$H | H | —SO$_3$H | —OH | — |
| 2g | O | F | H | H | H | —OH | — |
| 2h | =NH | H | —SO$_3$H | H | —SO$_3$H | —NH$_2$ | — |
| 2i | =N(CH$_3$)$_2$$^+$ | H | H | H | H | —OH | — |
| 2j | =N(CH$_3$)$_2$$^+$ | H | H | H | H | —N(CH$_3$)$_2$ | — |
| 2k | =N(CH$_3$)$_2$$^+$ | H | —SO$_3$H | H | —SO$_3$H | —N(CH$_3$)$_2$ | — |
| 5a | — | H | —CH$_3$ | H | —CH$_3$ | —OH | =O |
| 5b | — | H | —SO$_3$H | H | —SO$_3$H | —OH | =O |
| 5c | — | H | —CH$_3$ | H | —CH$_3$ | —NH$_2$ | =NH |
| 5d | — | H | —CH$_3$ | H | —CH$_3$ | —N(CH$_3$)$_2$ | =N(CH$_3$)$_2$$^+$ |
| 5e | — | H | H | —COOH | H | —OH | =O |
| 5f | — | H | H | —COOH | H | —N(CH$_3$)$_2$ | =N(CH$_3$)$_2$$^+$ |
| 24 | — | H | H | H | —CH(OH)O-† | —OH | —NH$_2$ |
| 34a | — | H | H | —COOH | —CH$_3$ | —OH | =O |
| 34b | — | H | H | H | —COOH | —OH | =O |
| 34c | — | H | H | —COOH | —CH$_3$ | —OH | =N(CH$_3$)$_2$$^+$ |
| 34d | — | H | H | H | —COOH | —OH | =N(CH$_3$)$_2$$^+$ |
| 43 | — | H | H | H | —COO-† | —OH | =NH |
| 44 | — | H | H | H | —COO-† | —NH$_2$ | =NH |
| 45 | — | H | H | H | —COOH | —OH | =NH |
| 46 | — | H | H | H | —COOH | —NH$_2$ | =NH |

*All R substituents not included in Table 2 are hydrogen and X$^1$ is oxygen.
†R$^{11}$ forms a ring.

In some embodiments, R$^1$ and R$^2$ and/or R$^7$ and R$^8$ together form an aryl or substituted aryl ring as shown in general formulas VII and VIII

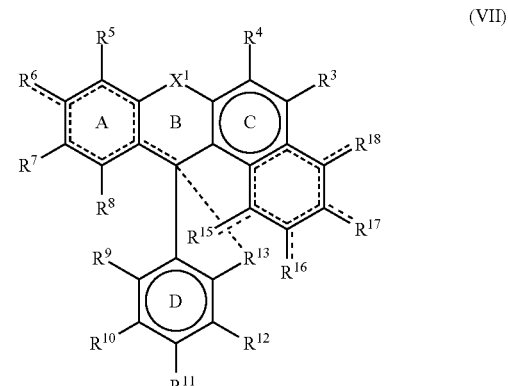

(VII)

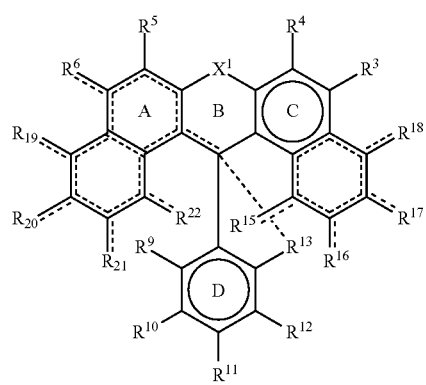

(VIII)

where each bond depicted as " ----- " is a single or double bond as needed to satisfy valence requirements. R$^3$-R$^{18}$ and X$^1$ in general formula VII are defined as above. R$^3$-R$^5$, R$^9$-R$^{22}$, and X$^1$ in general formula VIII are defined as above, and R$^6$ is hydrogen, hydroxyl, oxygen, halogen, thiol, amino, alkyl amino, or —NHR$^c$ where R$^c$ is as defined above. In certain embodiments, X$^1$ is oxygen, R$^3$, R$^4$, R$^5$ independently are hydrogen or halogen; R$^7$ and R$^8$, if present, independently are hydrogen or halogen; R$^9$-R$^{12}$ independently are hydrogen, amino, lower alkyl, carboxyl, or —SO$_3$H; R$^{15}$, R$^{17}$, R$^{19}$, and R$^{22}$ are hydrogen; R$^{13}$ is hydrogen, lower alkyl, lower alkoxy, —SO$_3$H, —COOR$^{14}$ where R$^{14}$ is hydrogen or lower alkyl and the bond depicted as " ----- " in ring B is a double bond, or R$^{13}$ is one or more atoms forming a ring system with rings B and D and the bond depicted as " ----- " in ring B is a single bond; at least one of R$^{16}$, R$^{17}$, and R$^{18}$ is hydroxyl, oxygen, amino, alkyl amino, or —NHR$^c$ where R$^c$ is as defined above; at least one of R$^{19}$, R$^{20}$ and R$^{21}$ is oxygen, imino, iminium, lower alkyl iminium, or —NHR$^c$ where R$^c$ is as defined above; in general formula VII, R$^6$ is oxygen, imino, iminium, lower alkyl iminium, or —NHR$^c$ where R$^c$ is as defined above, and in general formula VIII, R$^6$ is hydrogen or —NHR$^c$ where R$^c$ is as defined above. In particular embodiments, X$^1$ is oxygen, R$^3$, R$^4$, R$^5$, R$^8$ (if present), R$^9$, R$^{12}$, R$^{15}$, R$^{17}$, R$^{18}$, R$^{19}$, R$^{20}$, and R$^{22}$ are hydrogen; R$^7$ (if present) is hydrogen or halogen; R$^{10}$ and R$^{11}$ independently are hydrogen, amino, lower alkyl, carboxyl, or —SO$_3$H; R$^{13}$ is hydrogen, lower alkyl, lower alkoxy, —SO$_3$H, or —COOR$^{14}$ where R$^{14}$ is hydrogen or lower alkyl; R$^{16}$ is hydroxyl, amino, lower alkyl iminium, or —NHR$^c$ where R$^c$ is as defined above; R$^{21}$ is oxygen, imino, iminium, or lower alkyl iminium; R$^6$ is oxygen, imino, iminium, lower alkyl iminium, or —NHR$^c$ where R$^c$ is as defined above in general formula VII, or R$^6$ is hydrogen or —NHR$^c$ where R$^c$ is as defined above in general formula VIII. In certain embodiments, if X$^1$ is oxygen and either R$^{16}$ or R$^{18}$ is hydroxyl in structure VII, then R$^6$ is other than oxygen, amino, or alkyl amino, or at least one of R$^3$, R$^8$ or R$^{15}$ is other than hydrogen, or R$^{13}$ is one or more atoms forming a ring system with rings B and D and the bond depicted as " ----- " in ring B is a single bond. Representative compounds according to general formulas VII and VIII are shown in Table 3.

TABLE 3

| Cpd | R⁶* | R⁷ | R¹⁰ | R¹¹ | R¹³ | R¹⁶ | R¹⁸ | R¹⁹ | R²¹ |
|---|---|---|---|---|---|---|---|---|---|
| 1a | O | H | H | H | —OCH₃ | —OH | H | — | — |
| 1b | O | H | —CH₃ | H | —CH₃ | —OH | H | — | — |
| 1c | O | H | H | —COOH | H | —OH | H | — | — |
| 1d | O | H | H | —NH₂ | H | —OH | H | — | — |
| 1e | O | H | H | H | —SO₃H | —OH | H | — | — |
| 1f | O | H | —SO₃H | H | —SO₃H | —OH | H | — | — |
| 1g | O | F | H | H | H | —OH | H | — | — |
| 1h | =NH | H | —SO₃H | H | —SO₃H | —NH₂ | H | — | — |
| 1i | =N(CH₃)₂⁺ | H | H | H | H | —OH | H | — | — |
| 1j | =N(CH₃)₂⁺ | H | H | H | H | —N(CH₃)₂ | H | — | — |
| 1k | =N(CH₃)₂⁺ | H | —SO₃H | H | —SO₃H | —N(CH₃)₂ | H | — | — |
| 6a | H | — | —CH₃ | H | —CH₃ | —OH | H | H | =O |
| 6b | H | — | —SO₃H | H | —SO₃H | —OH | H | H | =O |
| 6c | H | — | —CH₃ | H | —CH₃ | —NH₂ | H | H | =NH |
| 6d | H | — | —CH₃ | H | —CH₃ | —N(CH₃)₂ | H | H | =N(CH₃)₂⁺ |
| 6e | H | — | H | —COOH | H | —OH | H | H | =O |
| 6f | H | — | H | —COOH | H | —N(CH₃)₂ | H | H | =N(CH₃)₂⁺ |
| 36a | H | — | H | —COOH | —CH₃ | H | —OH | =O | H |
| 36b | H | — | H | H | —COOH | H | —OH | =O | H |
| 36c | H | — | H | —COOH | —CH₃ | H | —OH | =N(CH₃)₂⁺ | H |
| 36d | H | — | H | H | —COOH | H | —OH | =N(CH₃)₂⁺ | H |

*All R substituents not included in Table 3 are hydrogen and X¹ is oxygen.

In some embodiments, the NIR dyes have mixed annulation, e.g., type [a] and type [c], type [a] and type [b], or type [b] and type [c]. For example, in some embodiments, $R^3$ and $R^4$ together form an aryl or substituted aryl ring and $R^7$ and $R^8$ together form an aryl or substituted aryl ring as shown in general formula IX. In other embodiments, $R^3$ and $R^4$ together form an aryl or substituted aryl ring and $R^6$ and $R^7$ together form an aryl or substituted aryl ring as shown in general formula X. In still other embodiments, $R^1$ and $R^2$ together form an aryl or substituted aryl ring and $R^6$ and $R^7$ together form an aryl or substituted aryl ring as shown in general formula XI.

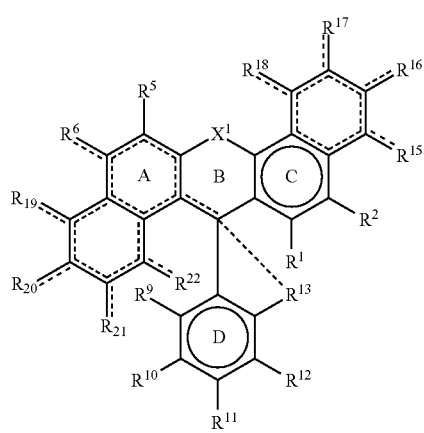

(IX)

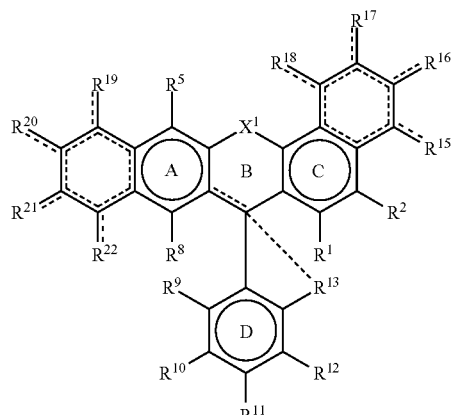

(X)

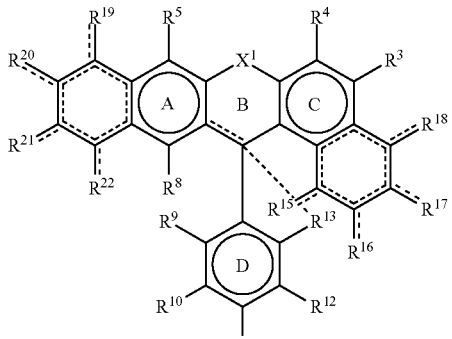

(XI)

In general formulas IX-XI, each bond depicted as "-----" is a single or double bond as needed to satisfy valence requirements. $R^1$-$R^5$, $R^7$-$R^{22}$ and $X^1$ are defined as above, and $R^6$ is hydrogen, hydroxyl, oxygen, halogen, thiol, amino, alkyl amino, or —NHR$^c$ where R$^c$ is as defined above. In certain embodiments, $X^1$ is oxygen; $R^1$-$R^6$ (if present), $R^8$ (if present), $R^9$, $R^{10}$, $R^{12}$, $R^{15}$, $R^{17}$, and $R^{22}$ are hydrogen; $R^{11}$ is hydrogen, amino, lower alkyl, carboxyl, or —SO₃H; $R^{13}$ is hydrogen, lower alkyl, lower alkoxy, —SO₃H, —COOR¹⁴ where $R^{14}$ is hydrogen or lower alkyl and the bond depicted as "━━━" in ring B is a double bond, or $R^{13}$ is one or more atoms forming a ring system with rings B and D and the bond depicted as "━━━" in ring B is a single bond; $R^{16}$, $R^{17}$, and $R^{18}$ independently are hydrogen, hydroxyl, oxygen, lower alkoxy, amino, alkyl amino, or —$NHR^c$ where $R^c$ is as defined above, and at least one of $R^{16}$ and $R^{18}$ is other than hydrogen; $R^{19}$-$R^{21}$ independently are hydrogen, hydroxyl, thiol, oxygen, imino, iminium, alkyl imino, alkyl iminium, amino, alkyl amino, or —$NHR^c$ where $R^c$ is as defined above, and at least one of $R^{19}$-$R^{21}$ is other than hydrogen. In particular embodiments, $X^1$ is oxygen; $R^1$-$R^6$ (if present), $R^8$ (if present) $R^9$, $R^{10}$, $R^{12}$, $R^{15}$, $R^{17}$, and $R^{22}$ are hydrogen; $R^{11}$ is hydrogen or carboxyl; $R^{13}$ is lower alkyl or carboxyl; $R^{16}$ and $R^{18}$ independently are hydrogen, hydroxyl, or oxygen, or —$NHR^c$ where $R^c$ is as defined above, and at least one of $R^{16}$ and $R^{18}$ is other than hydrogen; $R^{19}$-$R^{21}$ independently are hydrogen, oxygen alkyl iminium, or —$NHR^c$ where $R^c$ is as defined above, and at least one of $R^{19}$-$R^{21}$ is other than hydrogen. Representative compounds according to general formulas IX-VI are shown in Table 4.

TABLE 4

| Cpd | $R^{11}$* | $R^{13}$ | $R^{16}$ | $R^{18}$ | $R^{19}$ | $R^{20}$ | $R^{21}$ |
|---|---|---|---|---|---|---|---|
| 33a | —COOH | —CH₃ | H | —OH | H | H | =O |
| 33b | H | —COOH | H | —OH | H | H | =O |
| 33c | —COOH | —CH₃ | H | —OH | H | H | =N(CH₃)₂⁺ |
| 33d | H | —COOH | H | —OH | H | H | =N(CH₃)₂⁺ |
| 35a | —COOH | —CH₃ | H | —OH | =O | H | H |
| 35b | H | —COOH | H | —OH | =O | H | H |
| 35c | —COOH | —CH₃ | H | —OH | =N(CH₃)₂⁺ | H | H |
| 35d | H | —COOH | H | —OH | =N(CH₃)₂⁺ | H | H |
| 37a | —COOH | —CH₃ | H | —OH | H | =O | H |
| 37b | H | —COOH | H | —OH | H | =O | H |
| 37c | —COOH | —CH₃ | H | —OH | H | =N(CH₃)₂⁺ | H |
| 37d | H | —COOH | H | —OH | H | =N(CH₃)₂⁺ | H |
| 38a | —COOH | —CH₃ | —OH | H | H | =O | H |
| 38b | H | —COOH | —OH | H | H | =O | H |
| 38c | —COOH | —CH₃ | —OH | H | H | =N(CH₃)₂⁺ | H |
| 38d | H | —COOH | —OH | H | H | =N(CH₃)₂⁺ | H |
| 39a | —COOH | —CH₃ | —OH | H | =O | H | H |
| 39b | H | —COOH | —OH | H | =O | H | H |
| 39c | —COOH | —CH₃ | —OH | H | =N(CH₃)₂⁺ | H | H |
| 39d | H | —COOH | —OH | H | =N(CH₃)₂⁺ | H | H |

*All R substituents not included in Table 4 are hydrogen and $X^1$ is oxygen.

B. Structural Effects on Spectra and Stokes Shifts

Systematic structure-based evaluation surprisingly demonstrated that shifting the position of a substituent on the annulated ring of a singly annulated xanthene substantially red-shifted the emission and absorption maxima. For example, in some embodiments as shown in FIG. 1, type [c] annulated xanthenes according to general formula III may include substituents at the 3-position of the annulated ring ($R^{16}$) or at the 1-position ($R^{18}$). In working embodiments, positioning the substituent at the 1-position ($R^{18}$) instead of the 3-position ($R^{16}$) in general formula III and IV was found to red-shift the absorbance spectrum by more than 10 nm, typically by more than 30 nm or more than 50 nm, such as by 10-200 nm, 10-60 nm, 30-75 nm, 50-75 nm, 30-100 nm, or 75-200 nm. In some embodiments, the 3-1 transposition red-shifted the emission spectrum by at least 100 nm, such as by 100-200 nm, 120-160 nm, or 130-150 nm. In certain embodiments, when the substituent was at the 1-position ($R^{18}$ in general formulas III and IV), the emission maximum occurred at greater than 725 nm, greater than 750 nm, or greater than 770 nm. In some instances, the emission maxima were not measurable, but are believed to occur at greater than 850 nm (beyond the range of the instrument). Simultaneous enhancement of the Stokes shift also was noted. In some embodiments, the 3-1 transposition increased the magnitude of the Stokes shift by greater than 50 nm, such as by 50-100 nm, 70-90 nm, or 70-100 nm.

Thus, the 3-1 transposition provides several advantages. Both absorbance and emission maxima are red-shifted. Because the emission spectra typically have a greater red shift than the absorbance spectra, the Stokes shift is enhanced. This behavior occurs across symmetric (e.g., general formula IV) and asymmetric structures (e.g., general formula III), and was observed across various ionizable groups (e.g., hydroxyl and amine functionalities). In some embodiments, combining the 3-1 transposition with transposition of ionizable functionalities also provides an unexpected pH response. Some rhodols absorb and emit long wavelengths at high pH. However, with some embodiments of the disclosed fluorophores that combine a 3-1 transposition with ionizable moiety transposition, long wavelength behavior was observed at acidic pH values.

Figure 24:
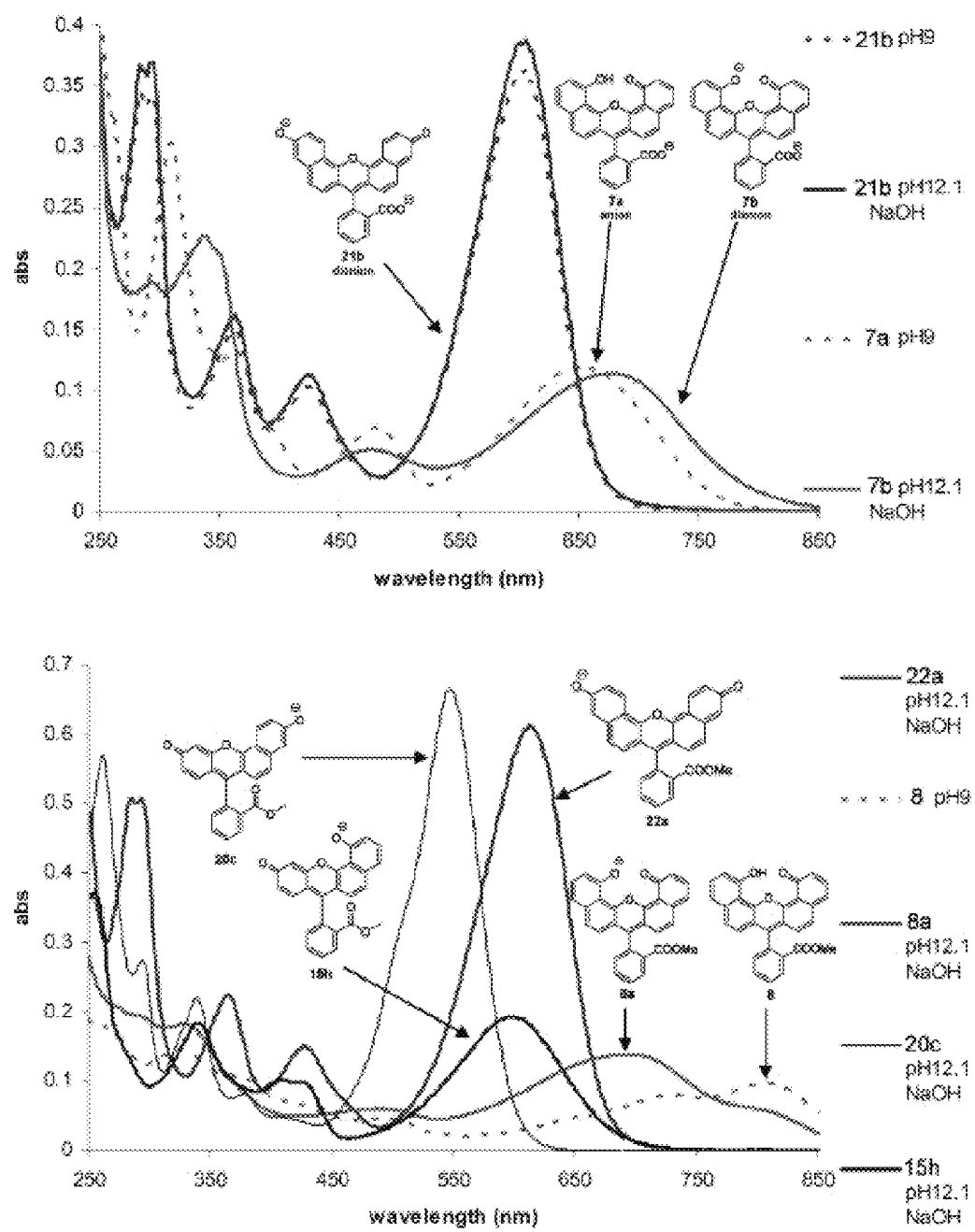
FIG. 24 is a series of absorption spectra showing the effect of ionization on the absorption maxima of several embodiments of the disclosed dyes.

In some embodiments, anionic forms of the fluorophores having a 3-1 transposition produce a greater red shift than the corresponding neutral forms of the fluorophores. For example, the absorbance maximum of compound 15a is red-shifted 15 nm compared to compound 20a. However, the absorbance maximum of compound 15h, the anionic form of compound 15a, has a red-shift of 50 nm compared to compound 20c, the anionic form of compound 20a. FIG. 24 is a series of UV-visible spectra illustrating the effect of ionization on the absorption spectra of some embodiments of the disclosed fluorophores. The bathochromic shift in emission wavelengths for compound 15h compared to compound 20c was 130 nm. The differences between these shifts results in NIR emission at 760 nm with a significantly enhanced Stokes shift of 160 nm.

Figure 25:
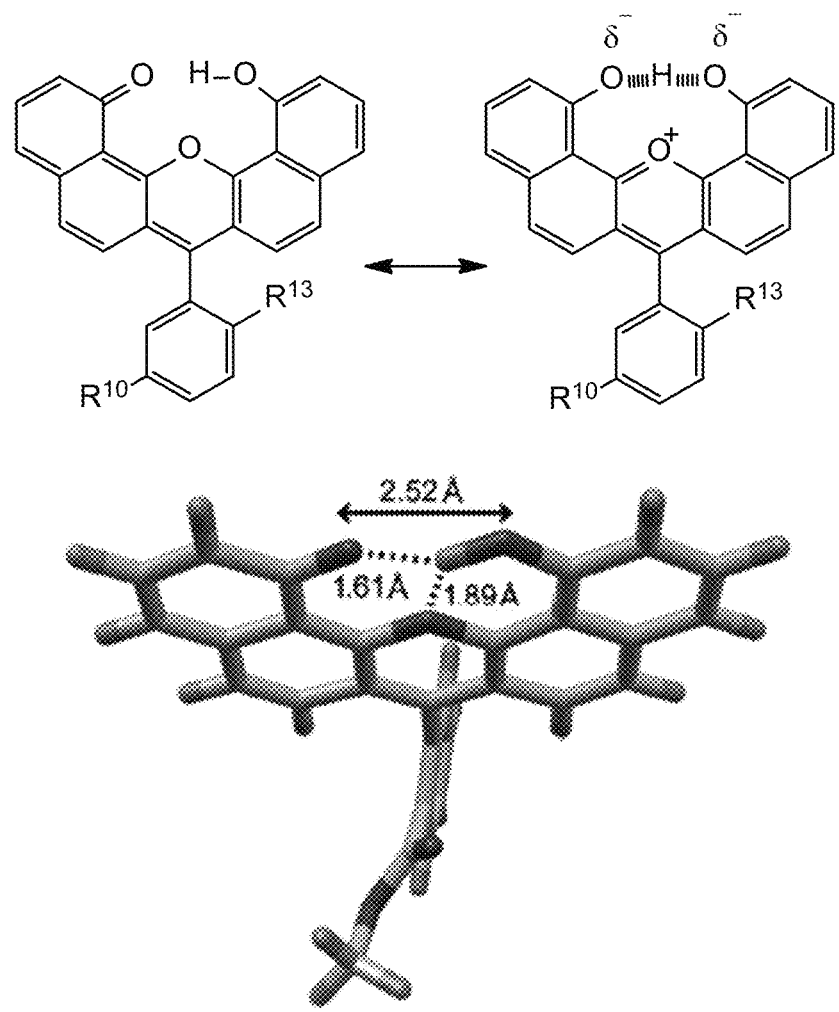
FIG. 25 shows the intramolecular hydrogen-bond network of one embodiment of the disclosed dyes, compound 8.
Figure 26:
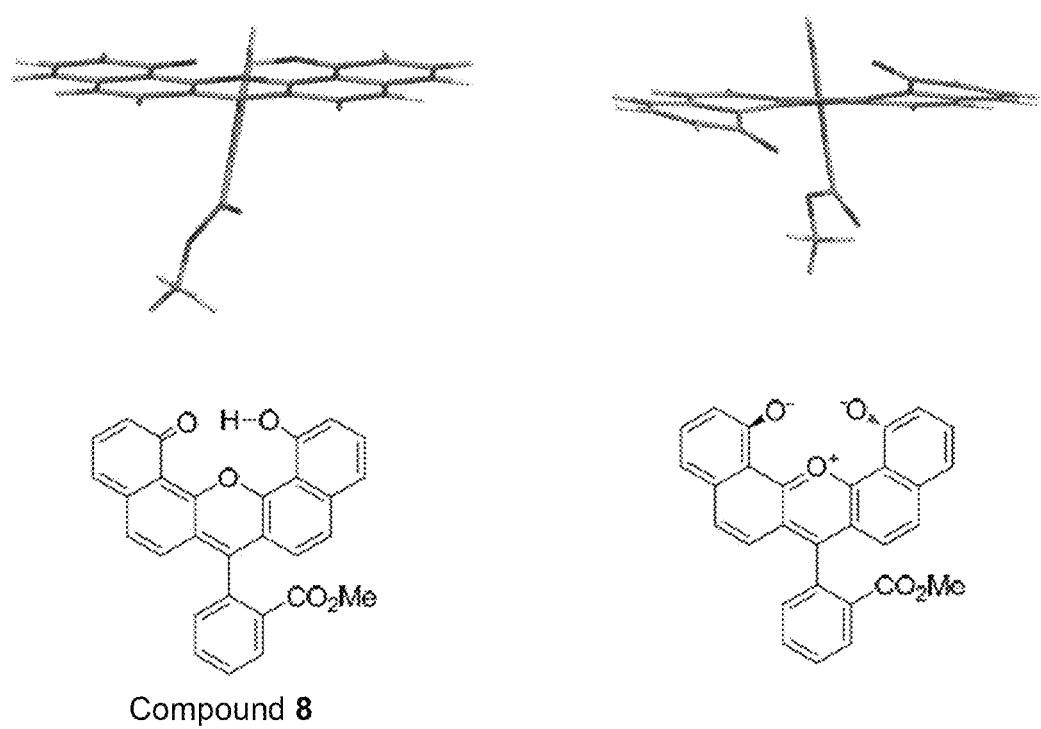
FIG. 26 is a molecular simulation showing that hydrogen bonding enhances coplanarity of the fused ring system for one embodiment of the disclosed dyes, compound 8, which is diminished upon deprotonation.

There are through-space polar interactions between $R^{18}$ and the internal bridge oxygen in compounds according to general formulas III, IX, and X. The field effect is further enhanced in the case of symmetric compounds, such as those according to general formula IV when $R^{19}$ is oxygen. A unique intramolecular hydrogen-bonding network also is present in such compounds, e.g., compound 8 (FIG. 25). This network produces enhanced negative charge density on the ionizable oxygen atoms, thereby promoting a relatively large bathochromic shift. Molecular simulations demonstrate that the hydrogen bonding network also enhances coplanarity of the fused ring system, which is diminished when the hydroxyl group is deprotonated (FIG. 26). The hydrogen bonding can be seen in compounds such as compound 8 by $^1$H NMR spectroscopy. A redistribution of the electronic density around the hydrogen atom occurs upon hydrogen bond formation between the hydroxyl proton, the carbonyl, and the central oxygen of compound 8. In compound 8, simulations show that the total hydrogen bond distance O—H—O between the carbonyl at $R^{19}$ and the hydroxyl at $R^{18}$ is 2.52 Å, which is lower than the typical hydrogen bonding distance (≥2.8 Å) and close to the distance observed for low-barrier hydrogen bonds (2.55 Å). Evidence of hydrogen bonding was also seen in compound 15a, but to a lesser degree. In compound 15a, the total hydrogen bond distance O—H—O between the hydroxyl at the $R^{18}$ position and the xanthene central oxygen is 2.95 Å, which falls in range of common hydrogen bonds. Removal of the shared proton in compound 8 to produce compound 8a does not result in a large bathochromic shift in the absorption maximum as is observed when compound 22 is deprotonated to compound 22a, thus providing further evidence of the effect of the hydrogen-bonding network on the characteristics of compounds such as 8. Surprisingly, when compound 10 was deprotonated, the shift was hypsochromic.

In some embodiments, e.g., compound 8, NIR fluorescence was observed in compounds exhibiting hydrogen bonding up to pH 9, while removal of the shared proton was observed to quench the fluorescence. Notably, compound 7 exists as its corresponding colorless lactone in 1:9 DMSO: buffer below physiological pH of 7.4, and thus embodies a unique pH probe.

Some embodiments of fluorophores having a chemical structure according to general formula III or IV have longer absorption and emission wavelengths than rhodamine. Analogues having an —NHR$^c$ (boronic acid) substituent at $R^{16}$ and $R^6$ (formula III) or $R^{21}$ (formula IV) are further red-shifted that the corresponding fluorophores having an —NH$_2$ at $R^{16}$ and $R^6/R^{21}$. In the absence of sugars, the boronic acids may be quenched through a PET (photoinduced electron transfer) mechanism. In certain embodiments, bathochromic shifts and increased quantum yields were observed for both asymmetric (formula III) and symmetric (formula IV) bis-boronic acid analogues upon sugar binding.

IV. SYNTHESIS

Figure 2:
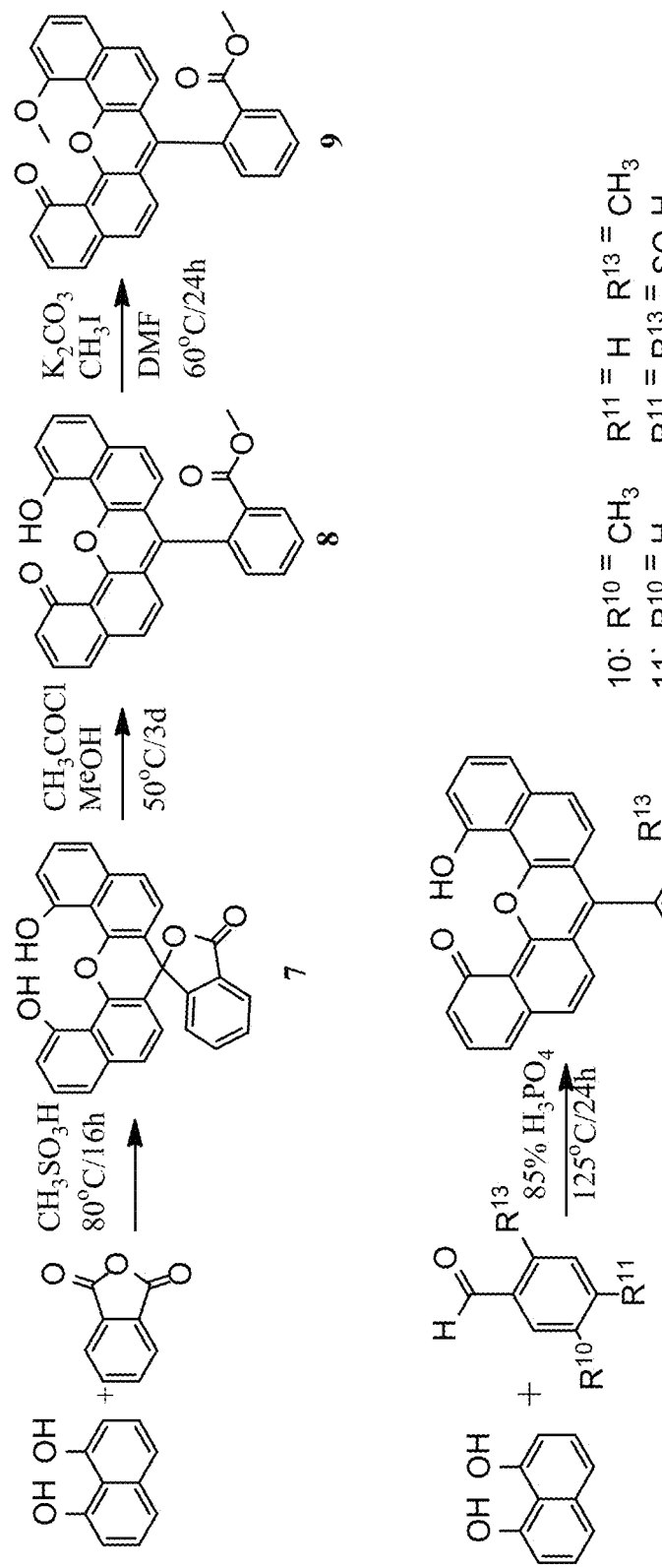
FIG. 2 is a reaction scheme illustrating the synthesis of some embodiments of the disclosed dyes having a chemical structure according to general formula IV.

Some embodiments of naphthofluorescein analogues having a chemical structure according to general formula IV are synthesized as shown in Scheme 1 (FIG. 2). In some embodiments, analogues are synthesized by acid condensation of 1,8-dihydroxynaphthalene and phthalic acid in methanesulfonic acid to produce a lactone-containing compound (compound 7). Reacting compound 7 with acetyl chloride in methanol opens the lactone ring, thereby esterifying the compound and producing the methyl carboxylate 8; one of the hydroxyl groups is converted to an oxygen through electronic density redistribution in the conjugated system. Further reaction of compound 8 with potassium carbonate and methyl iodide in dimethyl formamide converts the remaining hydroxyl group to a methoxy group (compound 9). In other embodiments, analogues according to general formula IV are synthesized by acid condensation of 1,8-dihydroxynaphthalene with a desired aldehyde in phosphoric acid to produce analogues having structures according to representative compounds 10 and 11. In some embodiments, compounds 10 and 11 further are reacted with potassium carbonate and methyl iodide to produce methyl analogues.

Figure 3:
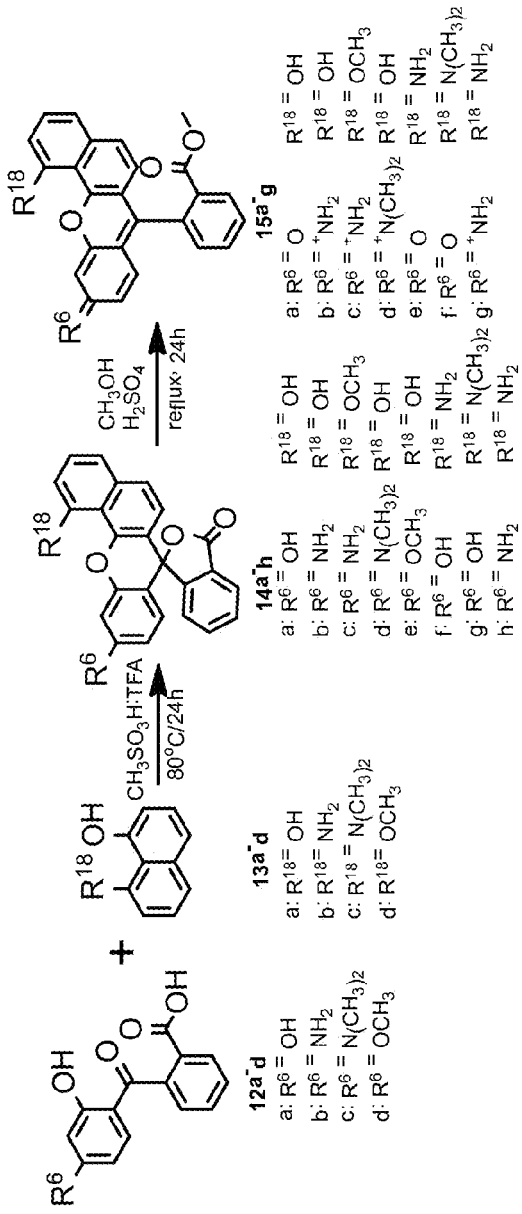
FIG. 3 is a reaction scheme illustrating the synthesis of some embodiments of the disclosed dyes having a semi-naphthofluorescein chemical structure according to general formula III.

Analogues having a chemical structure according to general formula III are synthesized by acid condensation as shown in Scheme 2 (FIG. 3). A hydroxybenzophenone derivative (compound 12) and a 1,8-naphthalene derivative (compound 13) are condensed by reaction in a 1:1 mixture of methanesulfonic acid and trifluoroacetic acid to produce a lactone-containing compound (compound 14). Further reaction of compound 14 with methanol in sulfuric acid opens the lactone ring, thereby esterifying the compound and producing the methyl ester (compound 15); compound 14 is converted to compound 15 via electronic redistribution in the conjugated system. Alternatively, reacting compound 14 with potassium carbonate and methyl iodide opens the ring and produces compound 16.

Figure 4:
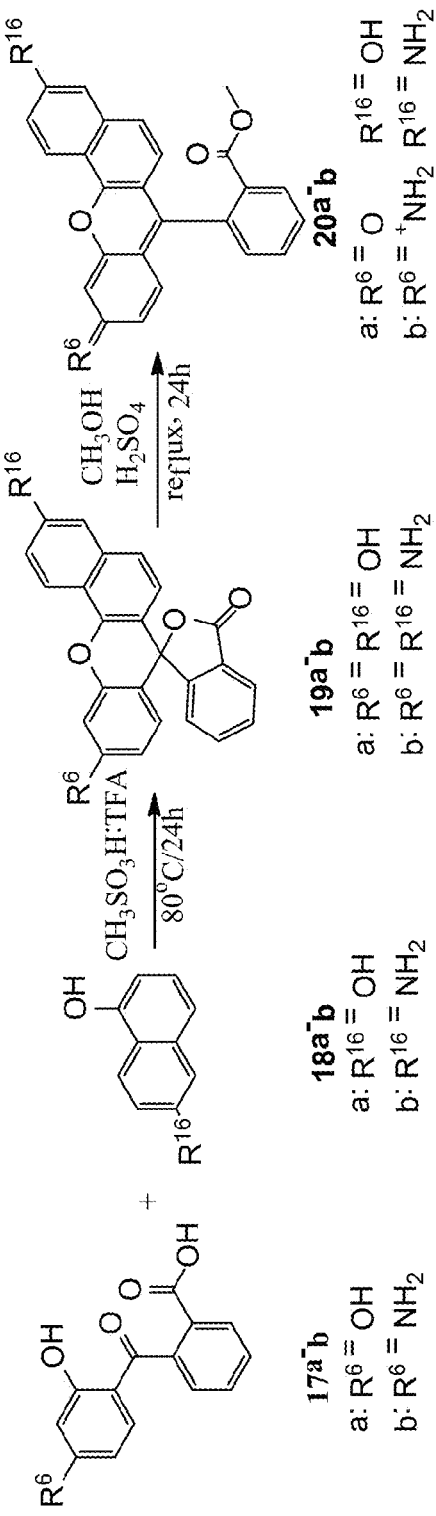
FIG. 4 is a reaction scheme illustrating the synthesis of some embodiments of the disclosed dyes having a rhodol or rhodamine chemical structure according to general formula III.

Certain asymmetric seminaphthofluorescein and rhodamine analogues having a chemical structure according to general formula III are synthesized as shown in Scheme 3 (FIG. 4). A hydroxybenzophenone derivative (compound 17) and a naphthol derivative (compound 18) are reacted via acid condensation in methanesulfonic acid/trifluoroacetic acid to produce a lactone-containing compound, compound 19. Further reaction of compound 19 with methanol in sulfuric acid produces compound 20a.

Figure 5:
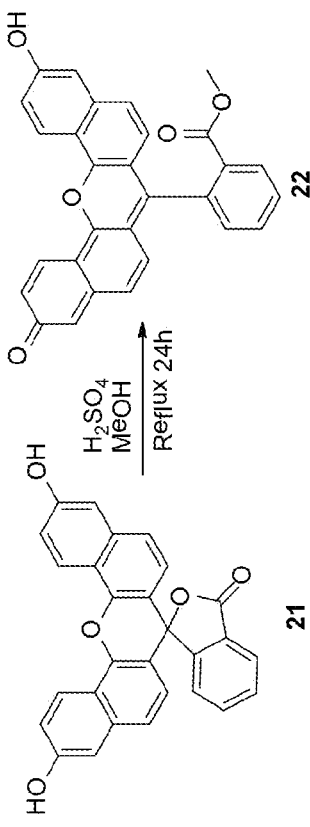
FIG. 5 is a reaction scheme illustrating the synthesis of one embodiment of the disclosed dyes having a chemical structure according to general formula IV.

A commercially available, lactone-containing naphthofluorescein analogue was converted to its methyl ester via Fischer esterification as shown in Scheme 4 (FIG. 5). The naphthofluorescein analogue (compound 21) is dissolved in methanol. Sulfuric acid is added, and the mixture is refluxed for 24 hours to produce compound 22.

Figure 6:
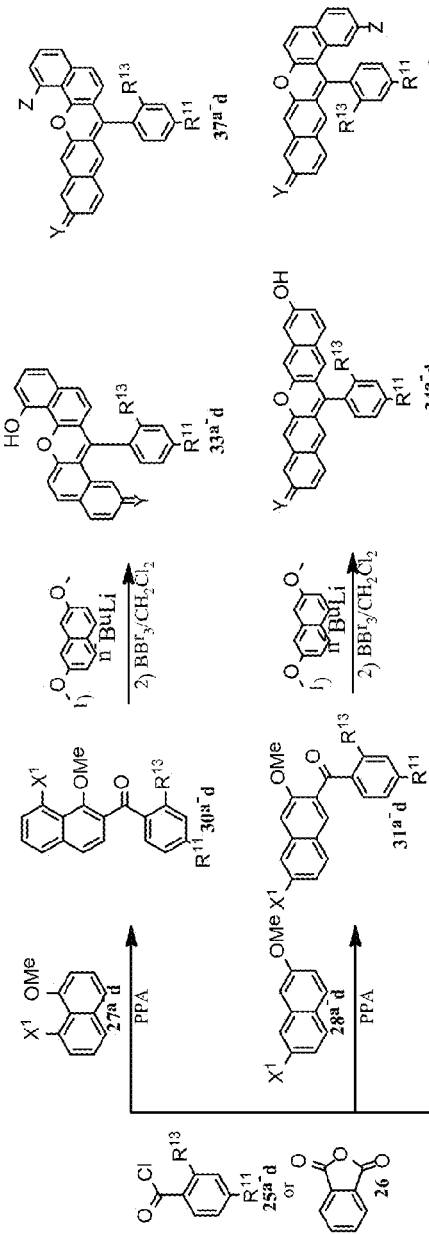
FIG. 6 is a reaction scheme illustrating the synthesis of some embodiments of the disclosed dyes having chemical structures according to general formulas VI and VIII-XI.
Figure 6:
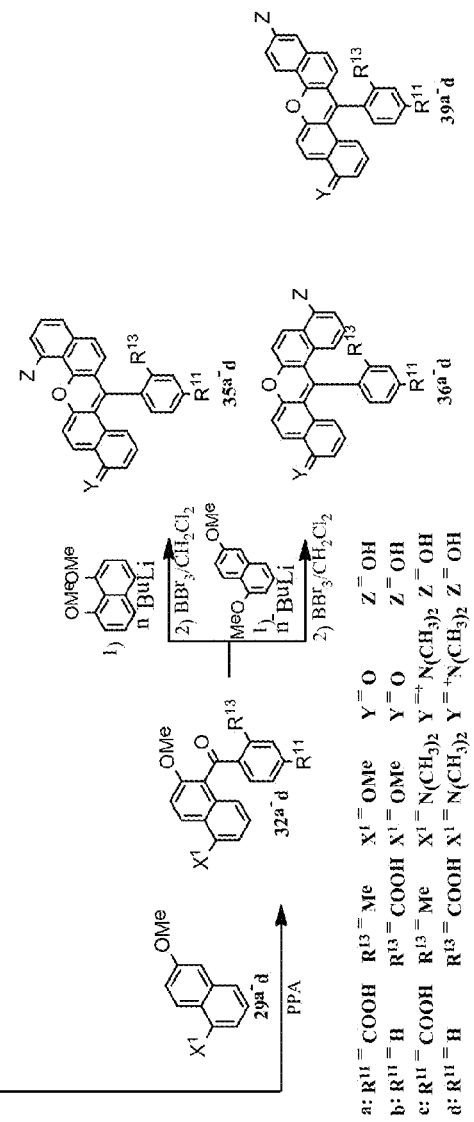

Some analogues having chemical structures according to general formula VI and some asymmetric, extended-conjugation analogues having chemical structures according to general formulas VIII-XI are synthesized as shown in Scheme 5 (FIG. 6). The method shown in Scheme 5 involves the formation of tertiary carbinol leuco bases via a Grignard reaction, followed by deprotection and condensation with BBr$_3$ to produce the corresponding xanthene dyes. Ketone precursors can be synthesized by reaction of the corresponding methoxy-naphthalenes with benzoyl chlorides or phthalic anhydride in the presence of polyphosphoric acid (Gorelick et al., *Zhurnal Org. Kihimii,* 1983, 19, 199-206).

Figure 7:
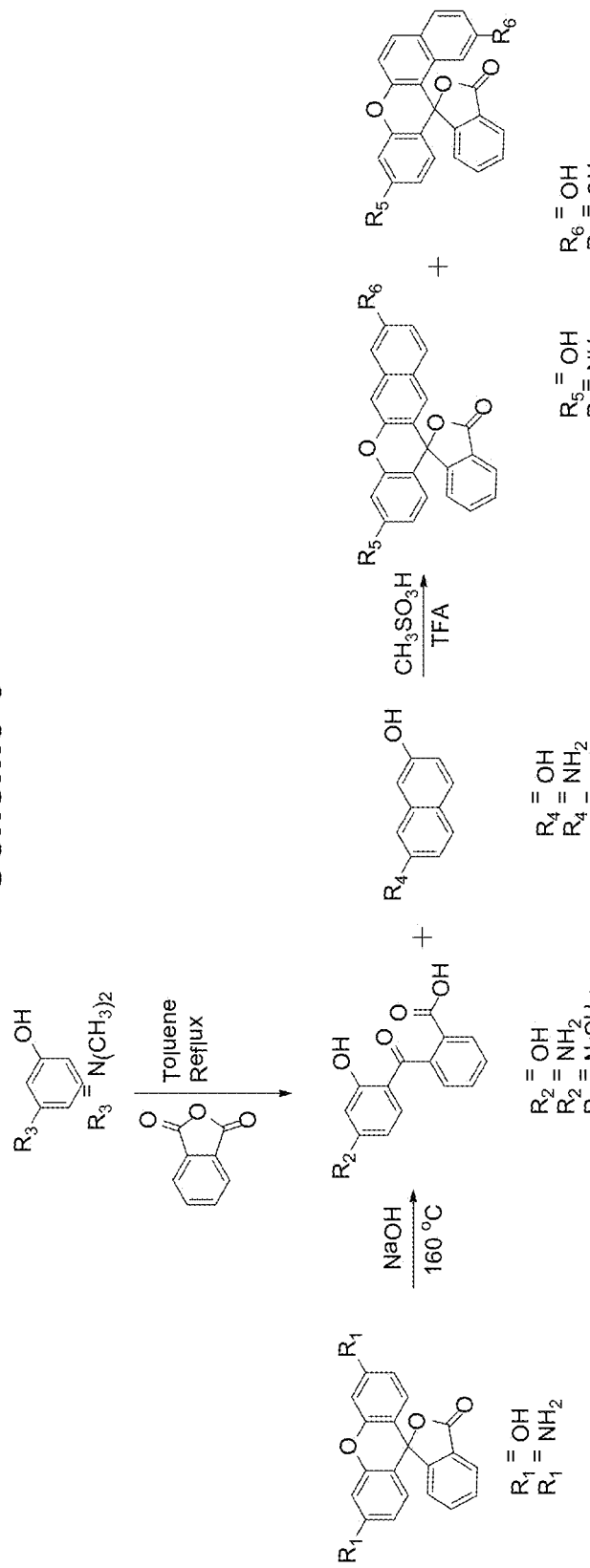
FIG. 7 is a reaction scheme illustrating the synthesis of some embodiments of the disclosed dyes having chemical structures according to general formulas V and VII.

Some analogues having chemical structures according to general formula V and VII are synthesized as shown in Scheme 6 (FIG. 7). A hydroxybenzophenone derivative is synthesized and condensed with a 1,8-naphthalene derivative in in a 1:1 mixture of methanesulfonic acid and trifluoroacetic acid to produce a mixture of lactone-containing compounds. The lactone rings can be opened, if desired, by reacting the compounds with methanol in sulfuric acid, or by reacting the compounds with potassium carbonate and methyl iodide to produce methyl ester derivatives.

Figure 8:
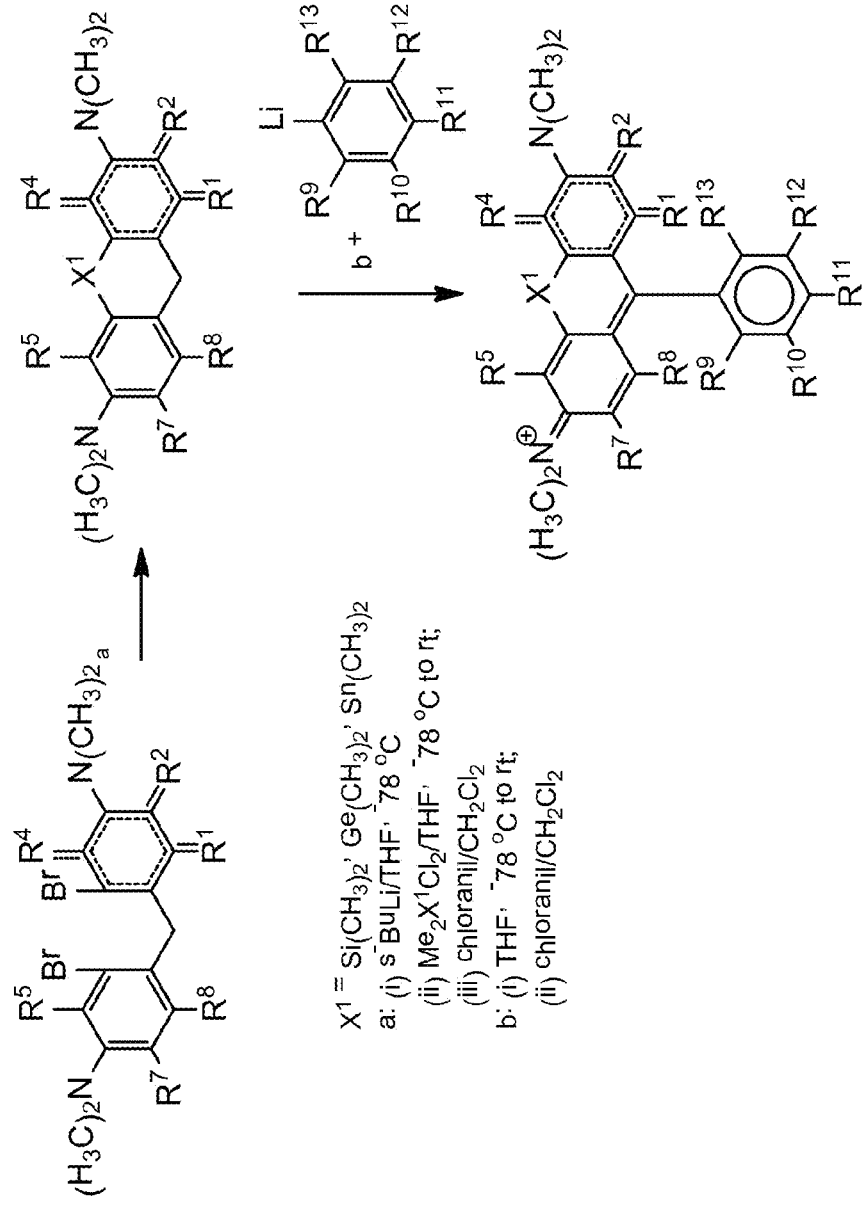
FIG. 8 is a reaction scheme illustrating the synthesis of some embodiments of the disclosed dyes having chemical structures according to general formula I where $X^1$ is $Si(CH_3)_2$, $Ge(CH_3)_2$, or $Sn(CH_3)_2$.

Some analogues having chemical structures according to general formula I where $X^1$ is Si(CH$_3$)$_2$, Ge(CH$_3$)$_2$, or Sn(CH$_3$)$_2$ may be synthesized according to Scheme 7 (FIG. 8). With respect to Scheme 7, $R^1$, $R^2$, $R^4$, $R^5$, $R^7$, and $R^8$ are as previously defined, with the proviso that none of $R^1$, $R^2$, $R^4$, $R^5$, $R^7$, or $R^8$ is —NH$_2$. In step (a), a dilithium intermediate may be generated from a bis(2-bromophenyl)methane derivative by halogen-metal exchange reaction, quenched with the appropriate dialkyl dichloride of silicon, germanium, or tin, and oxidized to form a xanthene. In step (b), a phenyl lithium derivative may be inserted to produce a rhodol or rhodamine-type structure. See, e.g., Koide et al., *ACS Chem. Biol.* 2011, 6(6), 600-608.

Figure 9:
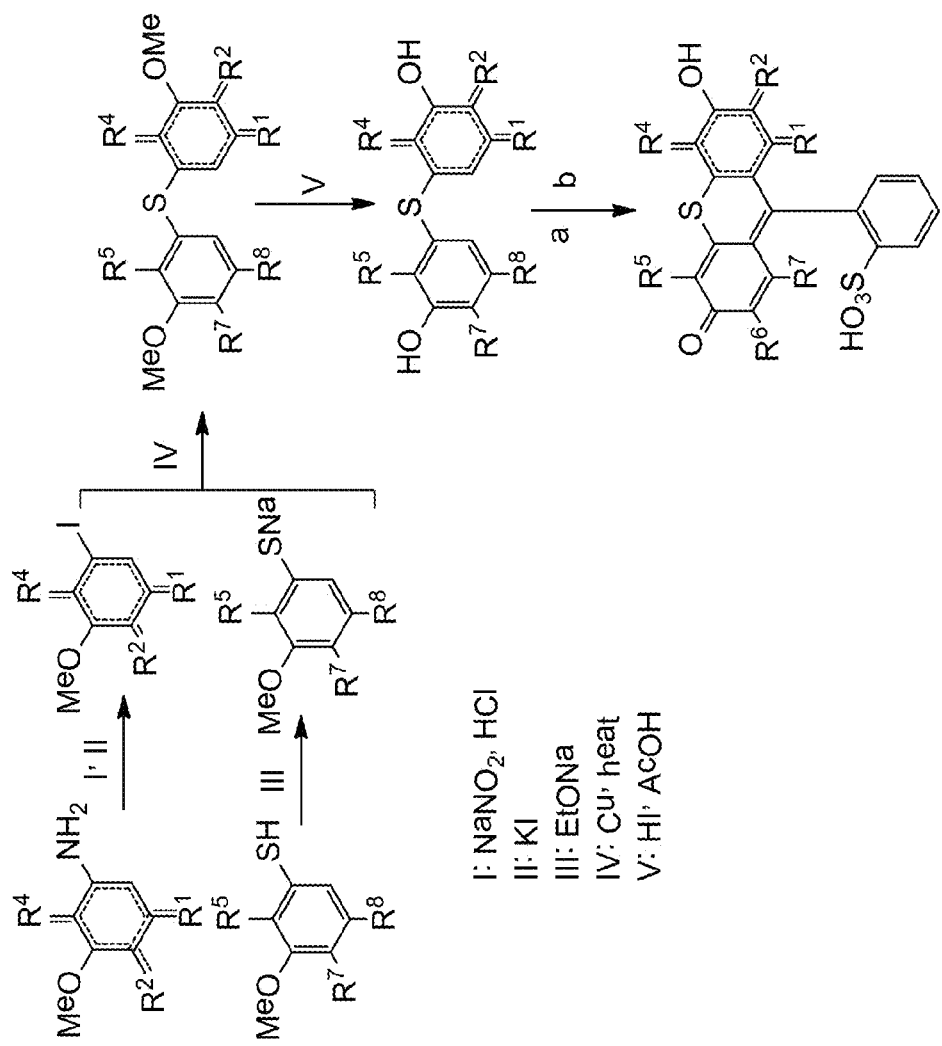
FIG. 9 is a reaction scheme illustrating the synthesis of some embodiments of the disclosed dyes having chemical structures according to general formula I where $X^1$ is S or Se.

Some analogues having chemical structures according to general formula I where $X^1$ is S or Se may be synthesized according to Scheme 8 (FIG. 9). With respect to Scheme 8, $R^1$, $R^2$, $R^4$, $R^5$, $R^7$, and $R^8$ are as previously defined, with the proviso that none of $R^1$, $R^2$, $R^4$, $R^5$, $R^7$, or $R^8$ is —NH$_2$ or halo. A sulfur analogue may be synthesized by preparing 3-iodoanisole from m-anisidine via its diazonium chloride, and separately preparing 3-methoxythiophenol sodium salt by reaction of sodium ethoxide with a corresponding thiophenol. Heating 3-iodoanisole and 3-methoxythiophenol sodium salt with powdery copper produces 1,1'-thiobis(3-methoxybenzene, which is converted to m,m'-thiodiphenol by ether cleavage with hydrogen iodide in acetic acid. A rhodol analogue may then be prepared by melting m,m'-thiodiphenol with phthalic anhydride in the presence of zinc chloride (path a), or by melting with 2-sulfobenzoic acid cyclic anhydride and toluene-4-sulfonic acid (path b) to produce the sulfobenzoic acid analogue shown in FIG. 9. See, e.g., Pfoertner, *J. Chem. Soc.*, Perkin Trans. 2, 1991, 523-526.

Figure 10:
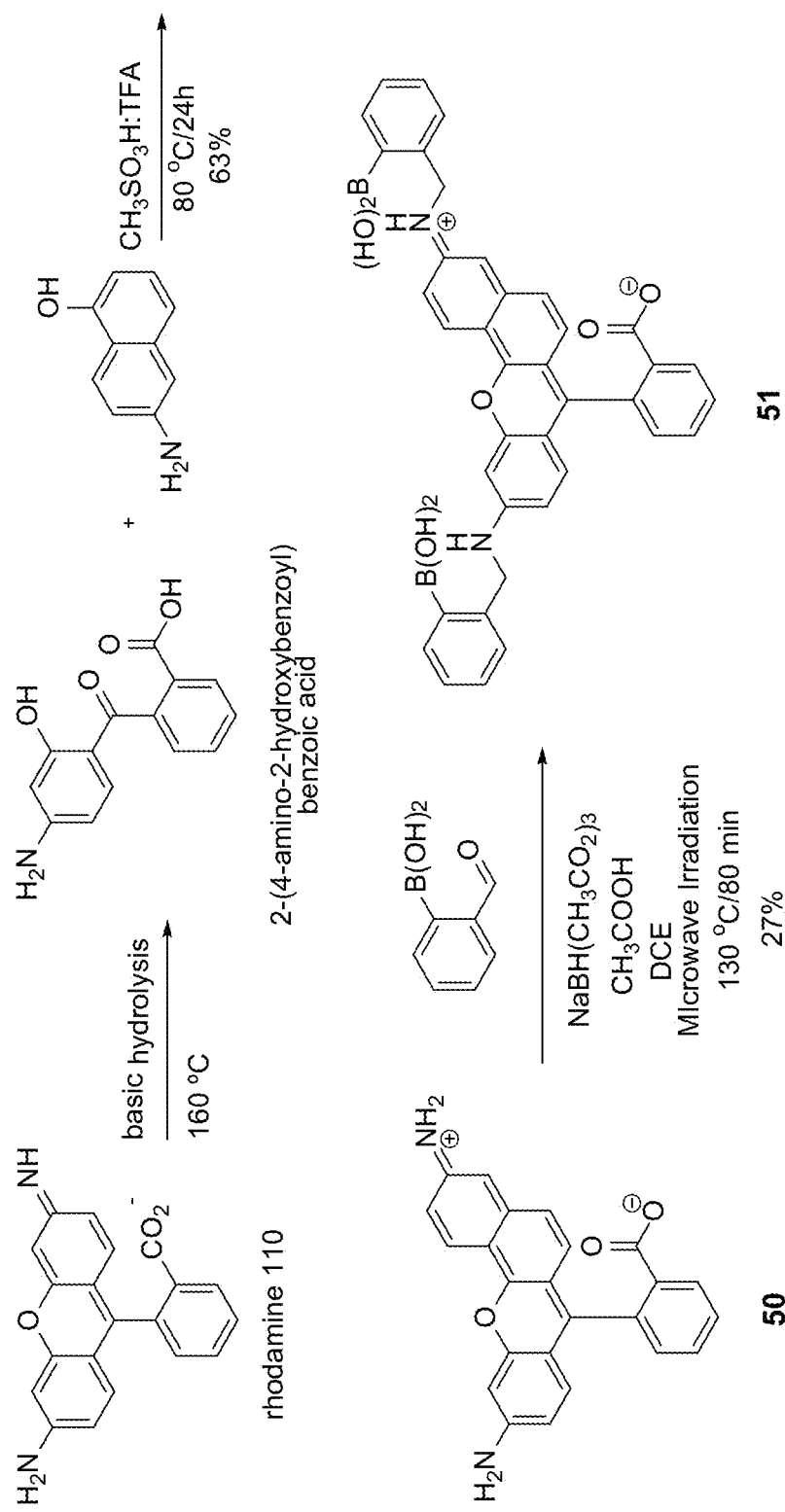
FIG. 10 is a reaction scheme illustrating the synthesis of some embodiments of the disclosed dyes having bis-boronic acid chemical structures according to general formula III.

Some analogues having chemical structures according to general formula (III) where $R^6$ and $R^{16}$ are amino or boronic acid are synthesized according to Scheme 9 (FIG. 10). A rhodamine is hydrolyzed under basic conditions, followed by acid condensation with an aminohydroxynaphthalene to produce a seminaphthorhodamine. Reductive amination produces the corresponding bis-boronic acid.

Figure 11:
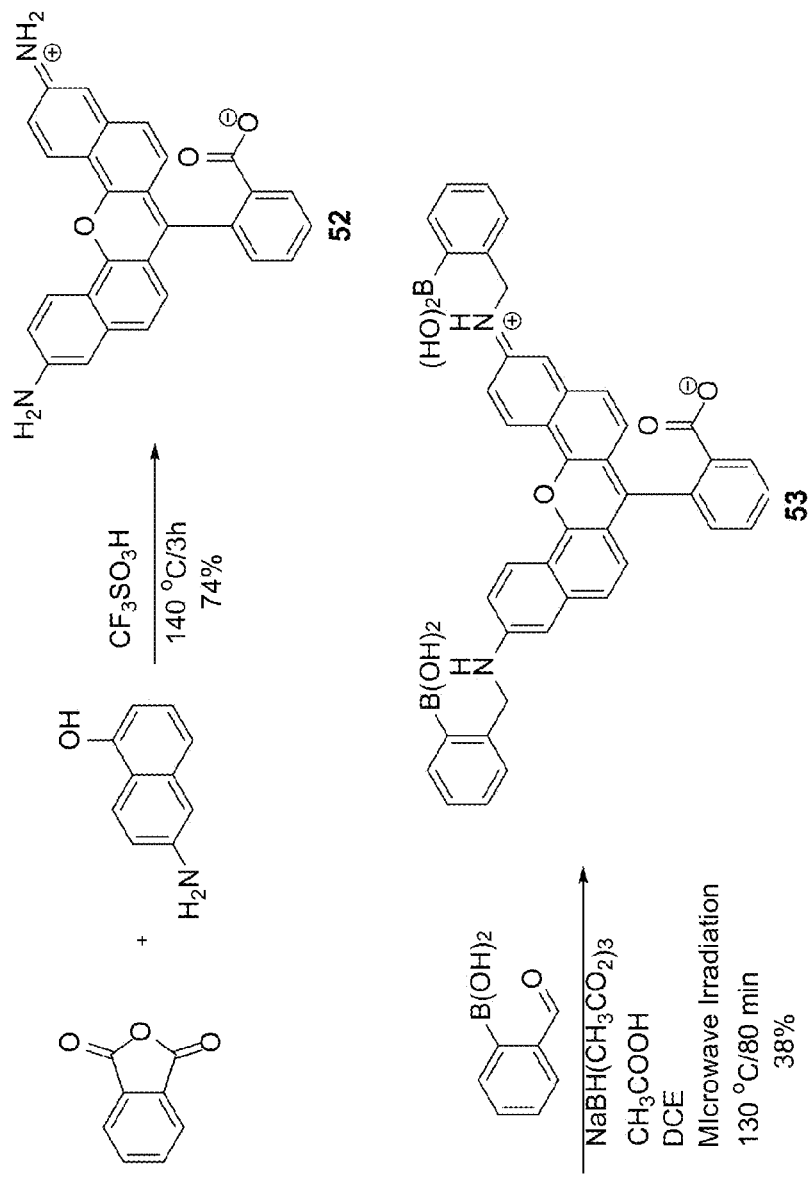
FIG. 11 is a reaction scheme illustrating the synthesis of some embodiments of the disclosed dyes having bis-boronic acid chemical structures according to general formula IV.

Some analogues having chemical structures according to general formula (iv) where $R^{16}$ and $R^{21}$ are amino or boronic acid are synthesized according to Scheme 10 (FIG. 11). A naphthorhodamine is prepared by acid-promoted condensation of phthalic anhydride and an aminohydroxynaphthalene. Reductive amination produces the corresponding bis-boronic acid.

In some embodiments, it may be advantageous to reduce the dye pKa and/or to increase aqueous solubility of the dyes. In certain embodiments, pKa may be reduced by halogenating the dye, such as by position one or more fluorine atoms ortho to one or more ionizable moieties such that a majority of the dye molecules are in an ionic form in a neutral aqueous solution. The inventors have discovered that ionized species of the disclosed dyes generally have a larger Stokes shift than neutral dye molecules. Embodiments of the dyes may be fluorinated by using a fluorinated naphthol during the synthesis, i.e., during the condensation reaction. Fluorinated naphthols may be synthesized by reacting hydroxynaphthalenes with a fluorine donor (e.g., Selectfluor® (1-chloromethyl-4-fluoro-1,4-diazoniabicyclo[2.2.2]octane bis(tetrafluoroborate)) in methyl cyanide at reflux as described in the literature (Yang et al., *Heteroatom Chem.*, 1998, 9, 229-239; Bluck et al., *J. Fluor. Chem.*, 2004, 125, 1873-1877).

In some embodiments, it also may be advantageous to reduce non-specific binding in biological media. To reduce non-specific binding, oligopegylated derivatives of the disclosed dyes can be prepared by conjugating the dye to an oligoethylene glycol. If bi-functional pegylating reagents are used, the dye may further be conjugated to other biological molecules of interest. Suitable bi-functional pegylating reagents comprising 6-8 ethylene glycol units are commercially available or can be prepared using literature protocols (Svedhem et al., *J. Org. Chem.*, 2001, 66, 4494-4503; Wosnick et al., *J. Am. Chem. Soc.*, 2005, 127, 3400-3405). Pegylated reagents can be conjugated via amide bond formation to embodiments of the disclosed dyes that comprise a carboxylic group. Pegylation also may increase solubility of dyes having hydrophobic properties.

V. APPLICATIONS

Some embodiments of disclosed NIR dyes are suitable for use in challenging biological media such as blood, plasma, and urine. Blood has strong background absorption, significant autofluorescence, and scatter in the visible region. Certain embodiments of the disclosed NIR dyes have emission spectra maxima at wavelengths that are long enough to overcome interference from blood hemoglobin, e.g., an emission spectrum maximum at greater than 640 nm, or greater than 680 nm. In particular embodiments, the disclosed NIR dyes also have an absorbance spectrum maximum that is greater than 640 nm, such as greater than 680 nm. In such embodiments, a light source having a wavelength greater than 640 nm can be utilized, thereby minimizing light absorption by blood. Dyes that function beyond the optical range of blood will simplify testing for analytes and biomarkers by limiting dilution and sample preparation/handling, thereby reducing sources of error, reducing time to obtain results, and/or reducing health hazards due to sample handling and manipulation. Current methods and detection agents utilize chromatography, fragile materials (e.g., those that are unstable in aqueous solution, require storage below −20° C. and/or require storage in the dark), and/or a high degree of sample processing. For example, in current methods, samples may be diluted more than 1000-fold to overcome optical interference from blood, or testing may be performed in plasma instead of whole blood. In contrast, some embodiments of the disclosed NIR dyes are stable for weeks at ambient temperature, even in solution. Certain embodiments of the disclosed NIR dyes also are more photostable in cell culture media than fluorescein.

Figure 12:
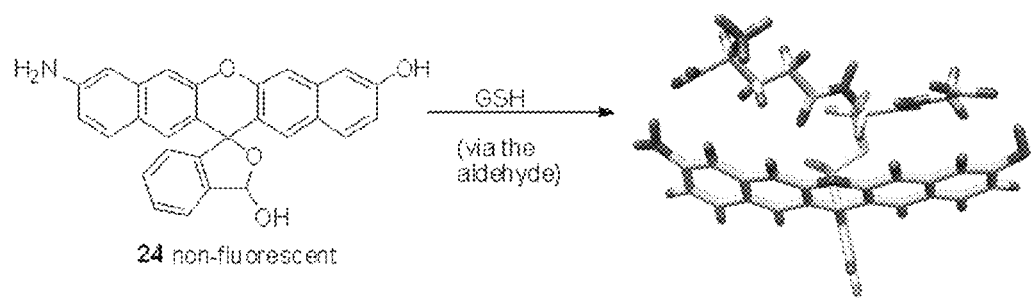
FIG. 12 illustrates the molecular interactions of one embodiment of the disclosed dyes, compound 24, with glutathione.

In particular, some embodiments of the disclosed NIR dyes include functional groups that may facilitate detection of specific molecular biomarkers. Embodiments of the NIR dyes may be functionalized to (a) produce a desired geometry having a combination of covalent and/or supramolecular interactions between the dye and a desired biomarker and/or (b) to alter oxidation-reduction and/or energy transfer properties in the presence of a desired biomarker. For instance, molecular modeling also indicates that some embodiments having a chemical structure according to general formula VI and polar end groups such as amino, oxygen, and/or hydroxyl groups at positions $R^{17}$ and $R^{20}$ may exhibit favorable electrostatic interactions with the polar ends of glutathione (FIG. 12).

Molecular modeling also indicates that some embodiments of the NIR fluorophores having a chemical structure according to general formula VI wherein at least one of $R^{17}$ and $R^{20}$ is —NHR$^c$ where R$^c$ is

Figure 13:
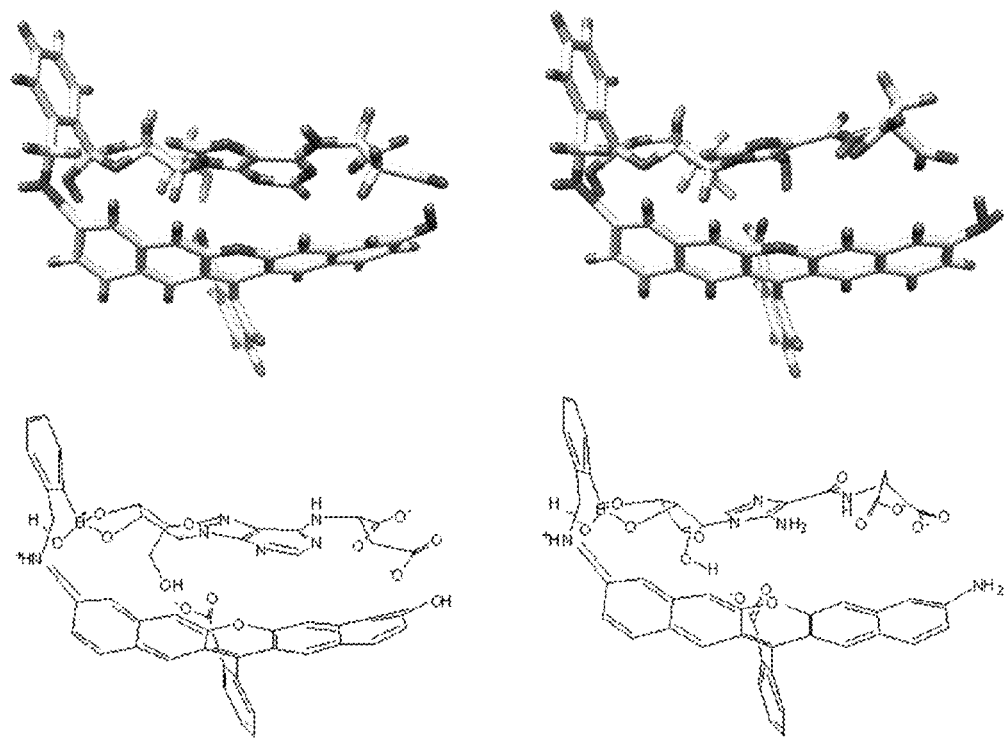
FIG. 13 illustrates the molecular interactions of two embodiments of the disclosed dyes, compounds 43 and 44, with S-Ado (left) and SAICAr (right).

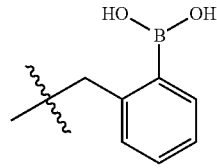 [SMILES: *Cc1ccccc1B(O)O]

may preferentially interact with specific nucleosides (FIG. 13). In certain embodiments, specificity may be enhanced when $R^{13}$ comprises a carboxylate moiety.

Biomarkers of interest include glutathione (GSH), which is diminished in whole blood, leukocytes and plasma in mitochondrial disorders (e.g., diabetes, atherosclerosis, neurodegenerative diseases, hypoxic-ischemic encephalopathy, autism, retinopathy of prematurity, chronic progressive external ophthalmoplegia, and cancer (Akturi et al., *PNAS U.S.A.*, 2009, 106, 3941-3945)) and organic acidemias (e.g., methylmalonic acidemia). Some commercially available methods for detecting GSH utilize detection agents that are not selective for GSH over other thiols (e.g., cysteine, dithiothreitol) and/or require testing in plasma. However, GSH levels in whole blood are in the millimolar range, or 100-1000 fold higher than in plasma.

Embodiments of the disclosed NIR dyes may be suitable for selective detection of GSH in blood. For example, molecular modeling shows that compound 5a (Table 2) has very favorable structural interactions with GSH. Additionally, compound 5a was found to be detectable in a 5% blood solution (see Example 2). Embodiments of NIR dyes functionalized to promote multipoint, glutathione-selective covalent, supramolecular and/or redox interactions may serve as indicators for oxidative stress and mitochondrial disorders.

Rhodamine B lactol has GSH selectivity, which is thought to arise from reaction with the aldehyde tautomer, thereby affording the observed emission and absorbance increases.

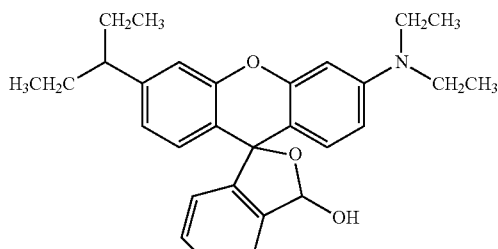

Rhodamine B lactol

It is believed that the equilibrium favors the thiohemiacetal in the case of GSH due, at least in part, to favorable electrostatic interactions between the polar groups of the dye (which actually modulate the ionization state and optical properties) and those of the GSH tripeptide. In order to understand potential salt bridge formation and ion pairing, the covalent complexes formed in the reaction of dyes such as compound 24 were simulated, demonstrating that the relatively extended GSH moiety can interact with the polar ends of the dyes simultaneously (FIG. 12).

Other biomarkers of interest include succinyl-5-amino-4-imidazole-carboxamide riboside (SAICA-riboside) and succinyladenosine (S-Ado), which are indicators of adenylosuccinate lyase (ADSL) deficiency.

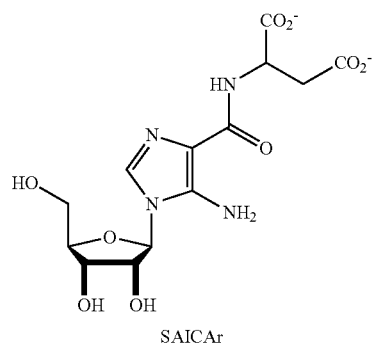

SAICAr

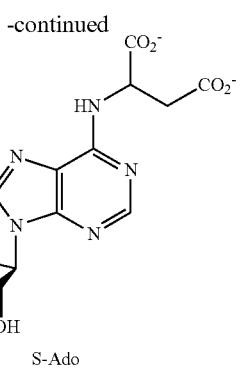

S-Ado

ADSL deficiency is a rare (approximately 1 in 200,000) inborn error of purine metabolism, which can result in mental retardation and seizure (Jaeken, *Lancet*, 1984, 2, 1058-1061). Undiagnosed genetic defects in purine and pyrimidine (PP) metabolism may result in early death and/or institutionalization. ADSL deficiency is characterized by massive urinary excretion (millimolar levels) of SAICA-riboside and S-Ado, the nucleosides corresponding to SAICA-ribotide (SAICAr) and adenylosuccinate.

Embodiments of the disclosed dyes functionalized with covalent and supramolecular binding sites targeted for specific nucleosides may serve as indicators for ADLS deficiency. In some embodiments, the NIR dye includes at least one boronic acid functional group, i.e., at least one R group is —NHR$^c$ where R$^c$ is

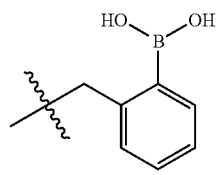 [SMILES: *Cc1ccccc1B(O)O]

A rhodamine modified with a phenyl boronic acid can exhibit unprecedented affinity for ribose and congeners as compared to fructose (Jiang et al., *J. Am. Chem. Soc.*, 2006, 128, 12221-12228).

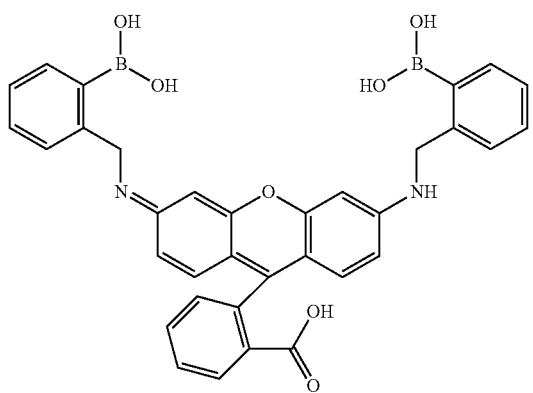

Rhodamine bis-boronic acid ("RhoBo")

Computer-assisted molecular simulations indicate that, apart from the preference of the boronic acid to react with the 2,3-cis diol of the furanose form of ribose and the strong electrostatic interaction B—O—H—N$^+$, non-covalent secondary interactions play an important role modifying the ionization state of the chromophore. FIG. 13 illustrates the charged H-bonding that can occur between the nucleosides and the carboxylate moiety of two embodiments (compounds 43 and 44, Table 2) of dyes having chemical structures according to general formula VI. Energy-minimized models in FIG. 13 were prepared using simulated annealing (sequential cycles of heating/cooling) using Sybyl™ X 1.1 (Tripos, St. Louis, Mo.) and geometry optimization with MOPAC2009 (Stewart Computational Chemistry, Colorado Springs, Colo.). Interaction with the carboxylate moiety appears to play a significant role in the interactions with S-Ado and SAICAr since esterification of the carboxylate moiety in the rhodamine bis-boronic acid causes its selectivity to revert to fructose.

In some instances, if evaluation in biological media is unsatisfactory, a molecule-imprinted polymer (MIP) specific to a particular analyte may be synthesized and utilized in a solid-phase extraction step prior to evaluation with embodiments of the disclosed NIR dyes. The MIP will allow capture and concentration of the analyte. Excellent synergism may be achieved as any deficiency in selectivity by the fluorophore-viologen conjugates and/or the MIP may compensate for the other component.

Some embodiments of the disclosed NIR dyes may be useful for cell imaging, intracellular pH sensing (e.g., by evaluating the absorbance and/or emission spectra and identifying dye ionization states within the cell), and/or detection of intracellular analytes such as thiols, hydrogen peroxide, hydrogen sulfide, and/or cyanide.

VI. KITS

Kits are also a feature of this disclosure. Embodiments of the kits include at least one compound according to any one of general formulas I-XI and suitable for selectively detecting an analyte in a sample (e.g., a biological fluid such as blood or urine). In some embodiments, the kits also include at least one buffer solution in which the compound, when combined with a sample including, or suspected of including, an analyte, will undergo a change in its absorbance spectrum and/or emission spectrum compared to the compound in the buffer solution combined with a sample that does not include the analyte. The kits may include a color comparison chart for evaluating a color change produced by a reaction between the compound and the analyte. The kits also may include one or more containers, such as a disposable test tube or cuvette, in which the detection can be performed. The kits may further include instructions for performing the detection. In some embodiments, the kits include control samples of analytes, e.g., glutathione, cysteine, homocysteine, succinyl-5-amino-4-imidazolecarboxamide riboside, and/or succinyladenosine. Typically the control samples are provided in solid form.

In some embodiments of the kits, the compound is provided as a solid, and the buffer is provided in liquid form. The buffer may be provided at a concentration suitable for detecting Cys, Hcy, GSH, succinyl-5-amino-4-imidazolecarboxamide riboside, succinyladenosine or a mixture thereof. Alternatively, the buffer may be provided as a concentrated solution, which is subsequently diluted prior to use. In certain embodiments, the compound may be pre-measured into one or more containers (e.g., test tubes or cuvettes), and the detection is subsequently performed by adding the buffer and test sample to the container.

VII. EXAMPLES

Reagents and General Procedures:
Chemistry. Unless otherwise indicated, all commercially available starting materials were used directly without further purification. Naphthofluorescein was obtained from Sigma-Aldrich. Silica gel (Sorbent Technologies) 32-63 μm was used for flash column chromatography. $^1$H-NMR was obtained on an ARX-400 Advance Bruker spectrometer. Chemical shifts (δ) are given in ppm relative to $d_6$-DMSO (2.50 ppm, $^1$H, 39.52 $^{13}$C) unless otherwise indicated. MS (HRMS, ESI) spectra were obtained at the Portland State University Bioanalytical Mass Spectrometry Facility on a ThermoElectron LTQ-Orbitrap high resolution mass spectrometer with a dedicated Accela HPLC system.

General acid condensation using methanesulfonic acid. Dihydroxynaphtahlene (3.12 mmol) and phthalic anhydride (1.56 mmol) are dissolved in 3 mL of methanesulfonic acid. The mixture is stirred at 90° C. for 24 hours. The mixture is allowed to cool down to room temperature, then poured into distilled water (50 mL). The precipitate is filtered and washed with water (3×50 mL). If no precipitate is formed, the mixture is neutralized to pH 5-7 by portion-wise addition of solid NaHCO$_3$. The precipitate is dried under vacuum. The target compound is isolated by flash column chromatography on silica gel.

General condensation method using CH$_3$SO$_3$H:TFA 1:1 mixture. Hydroxybenzophenone (918 μmol) and 1,8-naphthalene derivative (1380 μmol) are dissolved in 1.5 mL of methanesulfonic acid, then 1.5 mL of trifluoroacetic acid (TFA) are added. The mixture is heated and stirred at 80° C. for 16-24 hours. The reaction mixture is allowed to warm to room temperature, and then poured into 50 mL of deionized (DI) water. The mixture is neutralized to pH 6-7 by portion-wise addition of solid NaHCO$_3$. The resulting precipitate is filtered, washed with DI water and air dried. The target compound is isolated by flash column chromatography on silica gel.

General esterification method A. Carboxylate (0.243 μmol) is dissolved in 2 mL of methanol (MeOH). To this solution is added concentrated H$_2$SO$_4$ (100 μL) dropwise, then the mixture is refluxed 24 hours. The mixture is allowed to cool down to room temperature, then poured into 50 mL of ice water and 200 mg of NaHCO$_3$ is added in one portion. If a precipitate forms, the solid is filtered and washed with 2% NaHCO$_3$ (2×10 mL), then with water (2×10 mL). If no precipitate is obtained, the neutralized aqueous phase is extracted with CHCl$_3$ (3×50 mL). The organic phase is dried over Na$_2$SO$_4$ and the solvent evaporated under vacuum. The target compound is then isolated by flash column chromatography.

General esterification method B. Under an argon atmosphere, the compound (0.131 mmol) is dissolved in 25 mL of anhydrous methanol. The solution is cooled to 0° C. in an ice bath. Acetyl chloride (750 μL) is added dropwise. The mixture is stirred and kept at 50° C. for 48 hours. Acetyl chloride (300 μL) is added dropwise, and the mixture kept at 50° C. for additional 24 hours. The mixture is allowed to cool down to room temperature, and the solvent is evaporated under vacuum.

Example 1

Syntheses and Characterization

Figure 14:
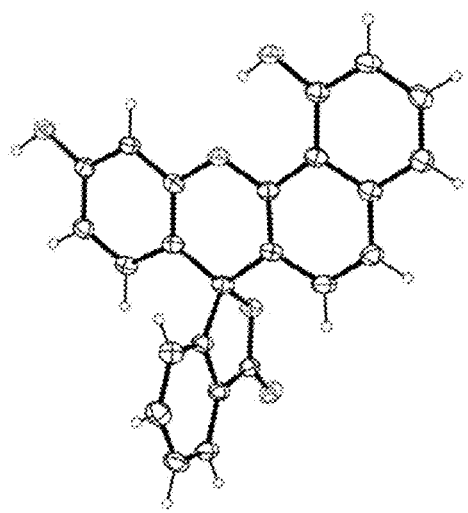

As shown in Scheme 1, analogues having a structure according to general formula IV were synthesized either via acid condensation of 1,8-dihydroxy-naphthalene and phthalic anhydride in methanesulfonic acid or by condensation of 1,8-dihydroxynaphthalene with the corresponding aldehydes in 85% H$_3$PO$_4$ at 125° C. /24 hours. The naphthofluorescein methyl ester 22 was obtained via a typical Fischer esterification protocol from 21 (Scheme 4). Asymmetric seminaphthofluorescein, rhodol and rhodamine analogues according to general formula III (Schemes 2 and 3) were synthesized by acid condensation of hydroxybenzophenones with the corresponding naphthols in a mixture of $CH_3SO_3H$:TFA 1:1 at 80° C. for 16-24 hours. The hydroxybenzophenones and 1,8-naphthalene derivatives required were synthesized according to described or modified literature protocols. The methyl ester derivatives were obtained by esterification in MeOH catalyzed by either $H_2SO_4$ or HCl; further methyl alkylation was furnished by treatment of either the carboxylate or methyl ester intermediate with methyl iodide in the presence of $K_2CO_3$ in dimethylformamide. In general, overall good yields were obtained for most of the compounds included in this series with the exception of the condensation products between dihydroxybenzophenone and 8-amino naphthol derivatives, where the major isolated product corresponds to fluorescein. All compounds were isolated by flash column chromatography (normal or reversed phase) and characterized by NMR and MS. The structure of compound 14a (FIG. 14) was confirmed by X-ray single crystal structure.

Compounds 21 and 7 (type [c] fully annulated naphthofluorescein with known regiochemistry versus fully annulated type [c] naphthofluorescein with 3-1 transposition)

Figure 15:
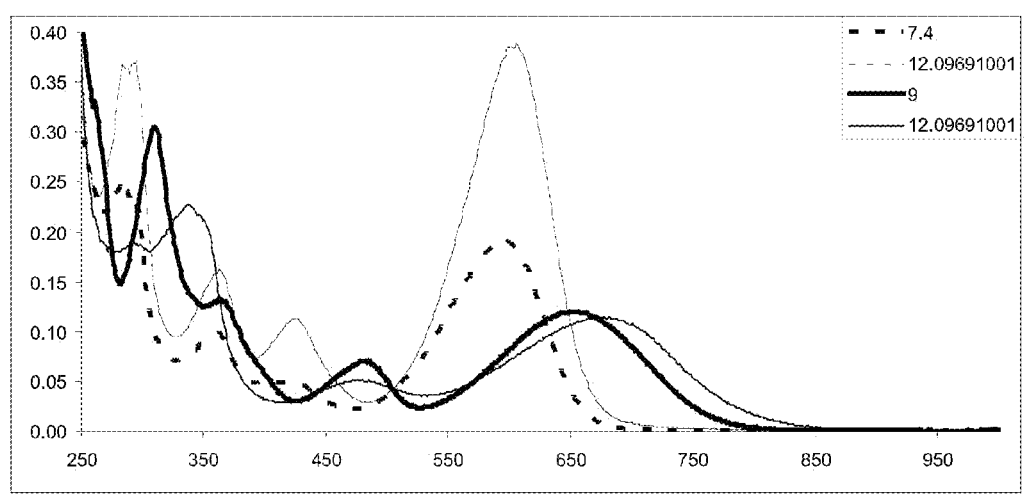
FIG. 15 is a series of absorbance spectra of two embodiments of the disclosed dyes, compounds 7 and 21, in their dianion and monanion states.

Compounds 21 and 7 were characterized by UV-visible spectroscopy (FIG. 15). Absorbance was measured using 15 µM solutions of each compound in a solution that was 90% aqueous, 10% DMSO. The peaks at 600 nm (light dashed line) and 675 nm (light solid line) represent the dianions of compounds 21 and 7, respectively, in NaOH (pH 12). The peaks at 590 nm (heavy dashed line) and 650 nm (heavy solid line) represent a mix of mono- and dianions of compound 21 at pH 7.4 and predominantly monoanions of compound 7 at pH 9, respectively. Thus, the 3-1 transposition resulted in red-shifted absorption spectra of about 60-75 nm, depending on the ionization state.

Compounds 21 and 7 also were characterized by their fluorescence emission spectra. Fluorescence was measured using 15 µM solutions of each compound in a solution that was 90% aqueous, 10% DMSO. For compound 21, the longest wavelength emission observed from the dianions occurred near 680 nm at pH 9. For compound 7 (transposed), the longest wavelength emission observed from the monoanion occurred near 800 nm at pH 9. Emission from the transposed dianion in sodium hydroxide was either too weak to be detected or, more likely, beyond the working range of the instrument (>850 nm). The 3-1 transposition resulted in red-shifted emission of about 120 nm, and possibly more depending on the ionization state.

The Stokes shift of each compound was measured and determined to be about 80 nm for the compound 21 dianion, and about 150 nm for the compound 7 (transposed) monoanion. Thus, the 3-1 transposition also enhanced the Stokes shift.

Compounds 22 and 8 (type [c] fully annulated naphthofluorescein methyl ester with known regiochemistry versus fully annulated type [c] naphthofluorescein methyl ester with 3-1 transposition)

Compound 22 was synthesized according to Scheme 4. Naphthofluorescein (compound 21, 0.05 g, 0.115 mmol) was dissolved in 2 mL methanol. The solution was cooled to 0° C. in an ice bath. Concentrated sulfuric acid (100 µL) was added to the solution, and the mixture was refluxed for 24 hours. The mixture was allowed to cool to room temperature, and then poured into 250 mL of ice water; 200 mg $NaHCO_3$ was added. The precipitate was filtered and washed twice with 2% $NaHCO_3$ and then twice with water. Compound 22 was isolated by flash column chromatography on silica gel using $CH_2Cl_2$:MeOH 9:1 for elution. The yield was 26 mg, 50%. $^1$H NMR (400 MHz, DMSO) δ 10.05 (s, 1H), 8.96 (d, J=9.2 Hz, 2H), 8.60 (d, J=9.0 Hz, 1H), 8.33 (d, J=7.9 Hz, 1H), 7.98 (t, J=6.9 Hz, 1H), 7.89 (t, J=7.7 Hz, 1H), 7.63 (d, J=9.2 Hz, 2H), 7.56 (d, J=6.8 Hz, 1H), 7.32-7.21 (m, 1H), 7.18-7.03 (m, 2H), 6.91 (d, J=9.1 Hz, 2H), 3.56 (s, 3H). HR ESI [M+H$^+$] m/z 447.1231 calc for $C_{29}H_{19}O_5$; 447.1237.

Compound 8 was synthesized by dissolving 1,8-dihydroxy-naphthalene (0.5 g, 3.12 mmol) and phthalic anhydride (0.231 g, 1.56 mmol) in 2 mL of methanesulfonic acid, and then adding 2 mL trifluoroacetic acid. The mixture was heated and stirred at 80° C. for 24 h. The mixture was allowed to cool to room temperature, and then poured into 100 mL of deionized water. The precipitate (compound 7) was filtered and washed with deionized water, and then isolated by flash column chromatography on silica gel using $CH_2Cl_2$:MeOH 9:1 for elution. Yield 0.122 g, 18%. Esterification then was carried out as described for compound 22. The target compound was isolated by flash column chromatography on silica gel using $CH_2Cl_2$:MeOH 9:1 for elution. Yield 0.023 g, 86%. $^1$H NMR (400 MHz, DMSO) δ 14.45 (s, 1H), 8.32 (dd, J=7.9, 1.0 Hz, 1H), 7.97 (td, J=7.5, 1.3 Hz, 1H), 7.87 (td, J=7.7, 1.3 Hz, 1H), 7.62-7.66 (m, 4H), 7.56 (dd, J=7.6, 0.9 Hz, 1H), 7.13, (d, J=7.2 Hz, 2H), 6.91 (dd, J=8.4, 0.8 Hz, 2H), 6.77 (d, J=9.1 Hz, 2H), 3.55 (s, 3H). $^{13}$C NMR (101 MHz, DMSO) δ 167.48, 165.22, 154.58, 137.69, 135.10, 134.52, 133.66, 130.95, 130.56, 130.40, 130.05, 129.20, 120.79, 119.99, 119.87, 116.26, 112.80, 52.42. HR ESI [M+H$^+$] m/z 447.1236, calc for $C_{29}H_{19}O_5$; 447.1237.

Figure 16:
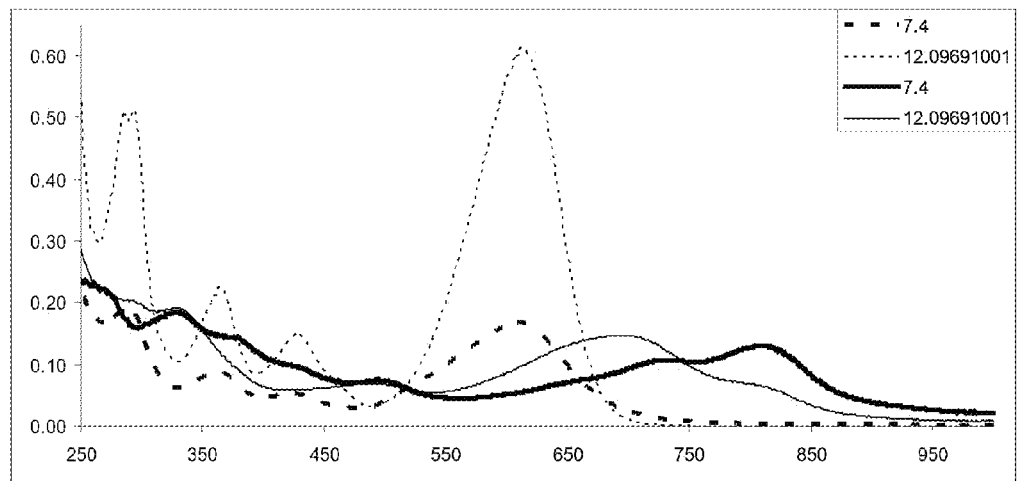
FIG. 16 is a series of absorbance spectra of two embodiments of the disclosed dyes, compounds 8 and 22, in their neutral and anionic forms.

Compounds 22 and 8 were characterized by UV-visible spectroscopy (FIG. 16). Absorbance was measured using 15 µM solutions of each compound in a solution that was 90% aqueous, 10% DMSO. The peaks at 610 nm (light dashed line) and 685 nm (light solid line) represent the anions of compounds 22 and 8, respectively, in NaOH (pH 12). The peaks at 605 nm (heavy dashed line) and 805 nm (heavy solid line) represent the neutral forms of compounds 22 and 8 at pH 7.4, respectively. Thus, the 3-1 transposition resulted in red-shifted absorption spectra of about 75-200 nm, depending on the ionization state.

It is interesting to note that for the transposed compound, ionization of the hydroxyl leads to shorter wavelength absorption. This is counter to what is observed for the known regiochemistry. It is also apparent from these first two examples that the 3-1 transposition's effect on spectral properties (red shifted spectra) is more pronounced when the carboxylate is replaced by a methyl ester.

The unique location of hydroxyl groups provided by the 3-1 transposition leads to increased interaction with the xanthene oxygen. This is one possible explanation for the observed red shift and unexpected behavior. Molecular modeling has demonstrated that in the neutral form, the hydroxyl proton of the transposed structure is held tightly with two hydrogen bonds and that in the anionic form, the xanthene oxygen is more electropositive for the transposed vs. the known regiochemistry (Mulliken charge of −0.289 vs. −0.386). Work is currently ongoing to further characterize this interaction and employ this strategy to further tune the spectral properties of xanthene-based structures without the need for complicated synthetic strategies which can include replacing the xanthene oxygen with more electropositive elements (i.e. S, Se, C, Si, etc.). In recent work Nagano and co-workers have used a similar strategy to extend the absorption and emission wavelength of rhodamines and pyronines by approximately 80 nm each (DOI: 10.1021/cb1002416). It should be noted that this approach retains the relatively small Stokes shifts (15-20 nm) present in the parent structure. However, the transposition approach disclosed herein increased the Stokes shift. Additionally, the emission of compounds reported by Nagano and co-workers are ca. 100 nm or more to the blue of those resulting from the 3-1 transposition approach described herein.

Compounds 22 and 8 also were characterized by their fluorescence emission spectra. Fluorescence was measured using 15 µM solutions of each compound in a solution that was 90% aqueous, 10% DMSO For compound 22, the longest wavelength emission observed from the anion occurred near 690 nm at pH 9. For compound 8 (transposed), emission was not observed. Given the greater than 800 nm absorbance peak and the typically large Stokes shifts observed in this class of compounds, it is likely that the emission was beyond the working range of the instrument (>850 nm). Assuming that emission of the transposed compound is beyond 850 nm, the 3-1 transposition resulted in red-shifted emission of more than 160 nm.

The Stokes shift of each compound was measured and determined to be about 80 nm for the compound 22 anion, and unmeasurable for the compound 8 (transposed) neutral form. It is likely that the 3-1 transposition also enhanced the Stokes shift.

Absorbance and fluorescence of compounds 22 and 8 also were measured in methanol. Compound 22 exhibited an absorption maximum at 598 nm. Compound 8 exhibited an absorption maximum at 701 nm. Compound 22 exhibited an emission maximum at 688 nm. Compound 8 exhibited an emission maximum at 816 nm. Thus, placement of the hydroxyl group proximal to the xanthene internal oxygen in compound 8 produced a bathochromic shift of 103 nm in the absorption spectrum. The transposition also imparted a corresponding shift in the excitation spectrum, and a large bathochromic shift of 128 nm in the fluorescence emission. Importantly, compound 8 absorbs and emits in the near-infrared with absorption and emission maxima of 701 nm and 816 nm, respectively. Analogous trends were observed in other solvent systems, e.g., DMSO, DMSO:aqueous 1:1 (pH 9), DMSO: aqueous 1:9 (pH9), DMSO: aqueous 1:1 (pH 12.1, NaOH), and DMSO: aqueous 1:9 (pH 12.1, NaOH).

Compounds 20a and 15a (type [c] annulated seminaphthofluorescein methyl ester with known regiochemistry versus annulated type [c] seminaphthofluorescein methyl ester with 3-1 transposition)

Some type [c] Seminaphthofluoresceins with the regiochemistry of the ionizable group on the carbon 3 have been commercially available. However, given the large effect observed when the carboxylate was replaced with a methyl ester on compounds with the transposed geometry above, the previously unreported seminaphthofluorescein methyl ester analogue was prepared for direct comparison with new transposed compounds.

Compound 20a was synthesized (Scheme 3) by condensing compound 17a (0.25 g, 0.968 mmol) and compound 18a (0.232 g, 1.45 mmol) under acidic conditions. Compound 19a was isolated by flash column chromatography on silica gel using EtOAc:MeOH 9:1 for elution. Yield 303 mg, 82%. Compound 19a (50 mg, 131 µmol) was esterified as described previously for compound 22. Compound 20a was isolated by flash column chromatography on silica gel using EtOAc:MeOH 9:1 for elution. Yield 27 mg, 52%. $^1$H NMR (600 MHz, DMSO) δ 10.57 (s, 1H), 8.53 (d, J=9.1 Hz, 1H), 8.25 (dd, J=8.0, 1.0 Hz, 1H), 7.90 (td, J=7.5, 1.3 Hz, 1H), 7.81 (td, J=7.8, 1.3 Hz, 1H), 7.53 (dd, J=14.7, 7.7 Hz, 2H), 7.34 (dd, J=9.1, 2.4 Hz, 1H), 7.23 (d, J=2.3 Hz, 1H), 6.86 (d, J=9.6 Hz, 1H), 6.78 (d, J=89 Hz, 1H), 6.50 (D, J=2.0 Hz, 1H), 6.47 (dd, J=9.6, 2.0 Hz, 1H), 3.56 (s, 3H). $^{13}$C NMR (151 MHz, DMSO) δ 183.52, 165.24, 159.27, 158.26, 150.81, 149.36, 137.52, 134.26, 133.27, 130.72, 130.69, 130.04, 192.92, 129.85, 129.48, 124.47, 123.27, 122.90, 119.85, 117.45, 116.08, 113.91, 110.07, 104.55, 52.10. HR ESI [M+H$^+$] m/z 397.1068; calc for $C_{25}H_{17}O_5$; 397.1081.

Compound 15a was synthesized (Scheme 2) by condensing compound 12a (0.250 mg, 0918 mmol) and compound 13a (0.232 g, 1.45 mmol) under acidic conditions. Compound 14a was isolated by flash column chromatography on silica gel using $CH_2Cl_2$:MeOH 9:1 for elution. Yield 300 mg, 81%. Compound 14a was esterified as described previously for compound 22. Compound 15a was isolated by flash column chromatography on silica gel using $CH_2Cl_2$:MeOH 9:1 for elution. Yield 40 mg, 77%. $^1$H NMR (600 MHz, DMSO) δ 10.78 (s, 1H), 8.25 (d, J=7.9 Hz, 1H), 7.91 (td, J=7.6, 1.3 Hz, 1H), 7.86-7.77 (m, 1H), 7.63-7.51 (m, 3H), 7.40 (s, 1H), 7.13 (s, 1H), 6.86 (d, J=9.7 Hz, 1H), 6.81 (d, J=8.7 Hz, 1H), 6.50 (dd, J=9.7, 1.9 Hz, 1H), 6.34 (d, J=2.0 Hz, 1H), 3.55 (s, 3H). HR ESI [M+H$^+$]m/z 397.1079; calc for $C_{25}H_{17}O_5$; 397.1081.

Figure 17:
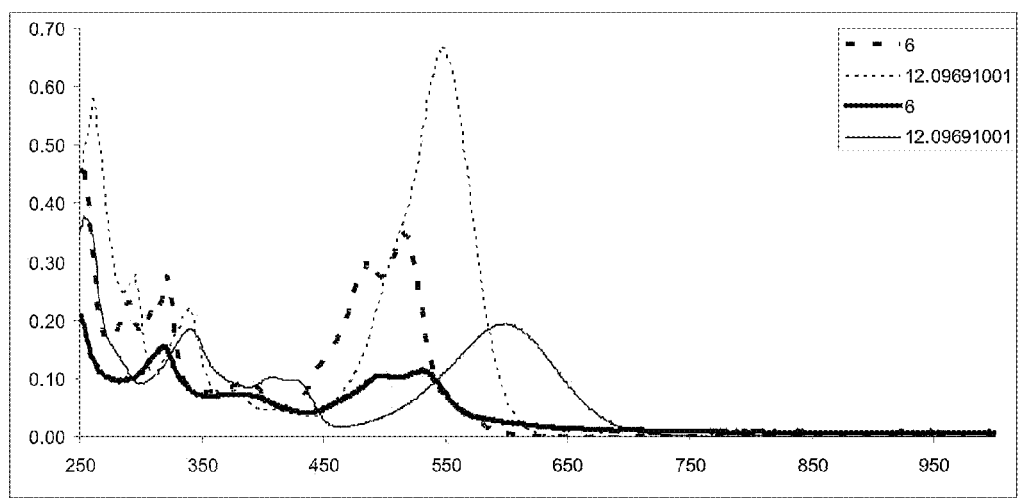
FIG. 17 is a series of absorbance spectra of two embodiments of the disclosed dyes, compounds 15a and 20a, in their neutral and anionic forms.

Compounds 20a and 15a were characterized by UV-visible spectroscopy (FIG. 17). Absorbance was measured using 15 µM solutions of each compound in a solution that was 90% aqueous, 10% DMSO. The peaks at 545 nm (light dashed line) and 595 nm (light solid line) represent the respective anions, compounds 20c and 15h, in NaOH (pH 12). The peaks at 515 nm (heavy dashed line) and 525 nm (heavy solid line) represent the predominantly neutral forms of compounds 20a and 15a at pH 6, respectively. Thus, the 3-1 transposition resulted in red-shifted absorption spectra of about 10-55 nm, depending on the ionization state.

Compounds 20 and 15a also were characterized by their fluorescence emission spectra. Fluorescence was measured using 15 µM solutions of each compound in a solution that was 90% aqueous, 10% DMSO. For compound 20a, the longest wavelength emission observed from its corresponding anion, compound 20c, occurred near 640 nm in NaOH (pH 12). For compound 15a (transposed), the longest wavelength emission observed from the corresponding anion, compound 15h, occurred near 760 nm in NaOH. The 3-1 transposition resulted in red-shifted emission by about 120 nm for the longest wavelength-emitting species.

The Stokes shift of each compound was measured and determined to be about 95 nm for the compound 20c anion, and about 165 nm for the compound 15h (transposed) anion. Thus, the 3-1 transposition enhanced the Stokes shift by about 70 nm.

Absorbance and fluorescence of compounds 20a and 15a also were measured in methanol. Compound 20a exhibited absorption maxima at 487 nm and 521 nm. Compound 15a exhibited absorption maxima at 501 nm and 536 nm. Compound 20a exhibited an emission maximum at 550 nm. Compound 15a exhibited an emission maximum at 582 nm. Thus, placement of the hydroxyl group proximal to the xanthene internal oxygen in compound 15a produced a bathochromic shift of 15 nm in the absorbance spectrum. The transposition also imparted a corresponding shift in the excitation spectrum, and a large bathochromic shift of 32 nm in the fluorescence emission.

Although the red shift of compound 15a in methanol was modest, its corresponding anion (compound15h) in DMSO: aqueous base 1:9 was shifted more substantially by 50 nm to 599 nm as compared to anion 20c under the same conditions. Its fluorescence emission was shifted by an even larger 130 nm, emitting at 760 nm. The comparatively large shift of the anion 15h supports a polar effect as playing a key role in modulating the HOMO-LUMO gap in the compound. The oxoanion of asymmetric 15h is expected to have a more significant field effect on the polarity of the proximal ether oxygen as compared to the corresponding oxoanion 20c. Like many other NIR-emitting compounds, compound 15h displays a relatively low quantum yield (less than 1%) in aqueous solution. The brightness of compound 15h is comparable to other NIR probes.

Compounds 15b and 15d (type [c] annulated seminaphthorhodafluor methyl esters (free amino and dimethyl, respectively) with 3-1 transposed regiochemistries)

The methyl ester analogue of known seminaphthofluorescein behaves similarly to previously reported compounds. Only a slight red shift, on the order of approximately 10 nm as compared to the carboxylate containing compound (Whitaker et al. *Analytical Biochemistry,* 1991, 194, 330-344), was observed. Thus the methyl ester analogues of known seminaphthorhodafluors (alternatively known as seminaphthorhodols) were not prepared for direct comparison. Literature values for similar compounds with the known regiochemistry were used for comparison with compounds 15b and 15d.

Figure 18:
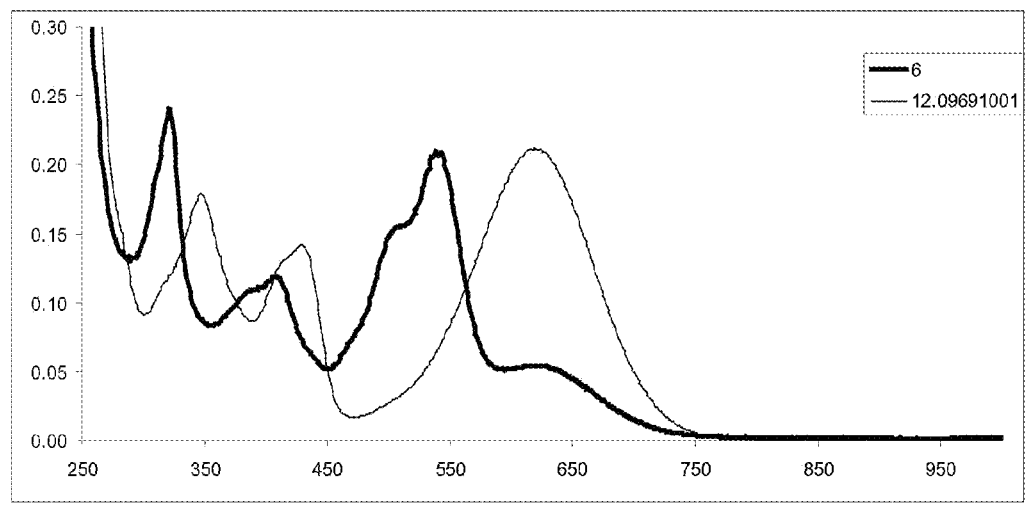
FIG. 18 is a series of absorbance spectra of one embodiment of the disclosed dyes, compound 15b, in its phenolic and phenoxide forms.

Compound 15b (free amino) was characterized by UV-visible spectroscopy (FIG. 18), and compared to C.SNARF-5 (literature, SNARF=seminaphthorhodafluor). Absorbance was measured using a 15 µM solution of compound 15b in a solution that was 90% aqueous, 10% DMSO. The peak at 535 nm (heavy line) represents the predominantly phenolic form of 15b at pH 6. The peak at 615 nm (light line) represents the phenoxide of compound 15b at in NaOH (pH12). In comparison, C.SNARF-5 produces a peak at 550 nm (anionic form) and a peak at 485 nm (neutral form) (Whitaker et al., *Anal. Biochem.* 1991, 194, 330-344). Thus, the 3-1 transposition resulted in red-shifted absorption spectra of about 50-65 nm, depending on the ionization state.

Compound 15b also was characterized by its fluorescence emission spectrum and compared to C.SNARF-5. Fluorescence was measured using a 15 µM solution of compound 15b in a solution that was 90% aqueous, 10% DMSO. For C.SNARF-5, the longest wavelength emission observed from the anion occurred near 632 nm (Whitaker et al., *Anal. Biochem.* 1991, 194, 330-344). For compound 15b (transposed), the longest wavelength emission observed from the phenoxide occurred near 770 nm. The 3-1 transposition resulted in red-shifted emission by about 138 nm for the longest wavelength-emitting species.

The Stokes shift of each compound was measured and determined to be about 82 nm for the C.SNARF-5 anion, and about 155 nm for the compound 15b (transposed) phenoxide. Thus, the 3-1 transposition enhanced the Stokes shift by about 73 nm.

Figure 19:
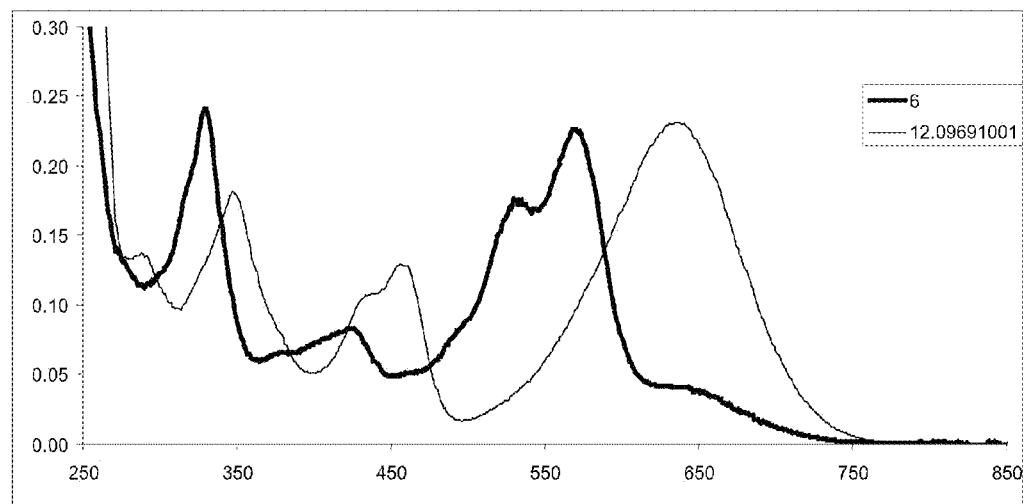
FIG. 19 is a series of absorbance spectra of one embodiment of the disclosed dyes, compound 15d, in its phenolic and phenoxide forms.

Compound 15d (dimethyl) was characterized by UV-visible spectroscopy (FIG. 19), and compared to SNARF-1 (literature). Absorbance was measured using 15 µM solutions of compound 15d in a solution that was 90% aqueous, 10% DMSO. The peak at 570 nm (heavy line) represents the predominantly neutral form of 15d at pH 6. The peak at 630 nm (light line) represents the phenoxide of compound 15d in NaOH (pH 12). In comparison, SNARF-1 produces a peak at 573 nm (anionic form) and a peak at 515 nm (neutral form) (Whitaker et al., *Anal. Biochem.* 1991, 194, 330-344). Thus, the 3-1 transposition resulted in red-shifted absorption spectra of about 55-57 nm, depending on the ionization state.

Compound 15d also was characterized by its fluorescence emission spectrum and compared to SNARF-1. Fluorescence was measured using a 15 µM solution of compound 15d in a solution that was 90% aqueous, 10% DMSO. For SNARF-1, the longest wavelength emission observed from the anion occurred near 631 nm (Whitaker et al., *Anal. Biochem.* 1991, 194, 330-344). For compound 15d (transposed), the longest wavelength emission observed from the phenoxide occurred near 780 nm (NaOH, pH 12). The 3-1 transposition resulted in red-shifted emission by about 149 nm for the longest wavelength-emitting species.

The Stokes shift of each compound was measured and determined to be about 58 nm for the SNARF-1 anion, and about 150 nm for the compound 15d (transposed) phenoxide. Thus, the 3-1 transposition enhanced the Stokes shift by about 92 nm.

Compounds 20b and 15g (type [c] annulated seminaphthorhodamine methyl esters (free amino) with known and 3-1 transposed regiochemistries, respectively)

To the best of the inventors' knowledge, the full seminaphthorhodamine analog with type [c] annulation and the known regiochemistry has not been reported. We prepared this compound (20b) for direct comparison with a new seminaphthorhodamine with the 3-1 transposition (15g).

Figure 20:
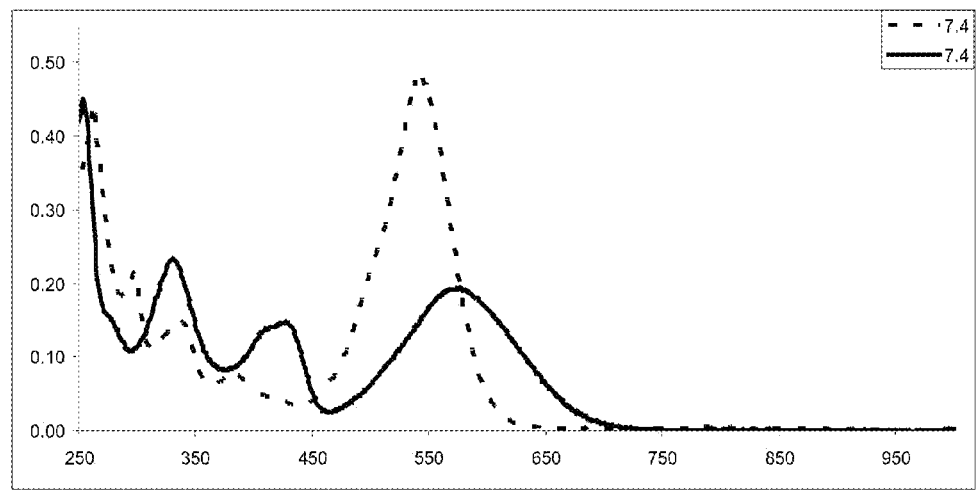
FIG. 20 is a series of absorbance spectra of two embodiments of the disclosed dyes, compounds 15g and 20b, in their cationic forms.

Compounds 20b and 15g were characterized by UV-visible spectroscopy (FIG. 20). Absorbance was measured using 15 µM solutions of each compound in a solution that was 90% aqueous, 10% DMSO. The peaks at 540 nm (dashed line) and 570 nm (solid line) represent the cations of compounds 20b and 15g, respectively, at pH 7.4. Thus, the 3-1 transposition resulted in a red-shifted absorption spectrum of about 30 nm.

Compounds 20b and 15g also were characterized by their fluorescence emission spectra. Fluorescence was measured using 15 µM solutions of each compound in a solution that was 90% aqueous, 10% DMSO. For compound 20b, the longest wavelength emission observed from the cation occurred near 640 nm at pH 7.4. For compound 15g (transposed), the longest wavelength emission observed from the cation occurred near 770 nm at pH 7.4. The 3-1 transposition resulted in red-shifted emission by about 130 nm.

The Stokes shift of each compound was measured and determined to be about 100 nm for the compound 20b cation, and about 200 nm for the compound 15g (transposed) cation. Thus, the 3-1 transposition enhanced the Stokes shift by about 100 nm.

Compounds 15e and 15f (Type [c] annulated Seminaphthorhodafluor methyl esters (free amino and dimethyl) with 3-1 transposed regiochemistries and the ionizable moieties transposed)

In addition to the previous examples, a second series of seminaphthorhodafluors (15e-15f) with the 3-1 transposition was prepared in which the ionizable hydroxyl and amine (free amino and dimethyl) functionalities also were transposed. To the best of the inventors' knowledge, no directly comparable structure has been reported in the literature. The nearest compound for comparison, a type [c] annulated seminaphthorhodafluor with the known regiochemistry, was reported to "display longer wavelength fluorescence, emitting at 600 nm in MeOH when excited at 525 nm." (Clark et al., *Tetrahedron Lett.,* 2004, 45, 7129-7131.)

Figure 21:
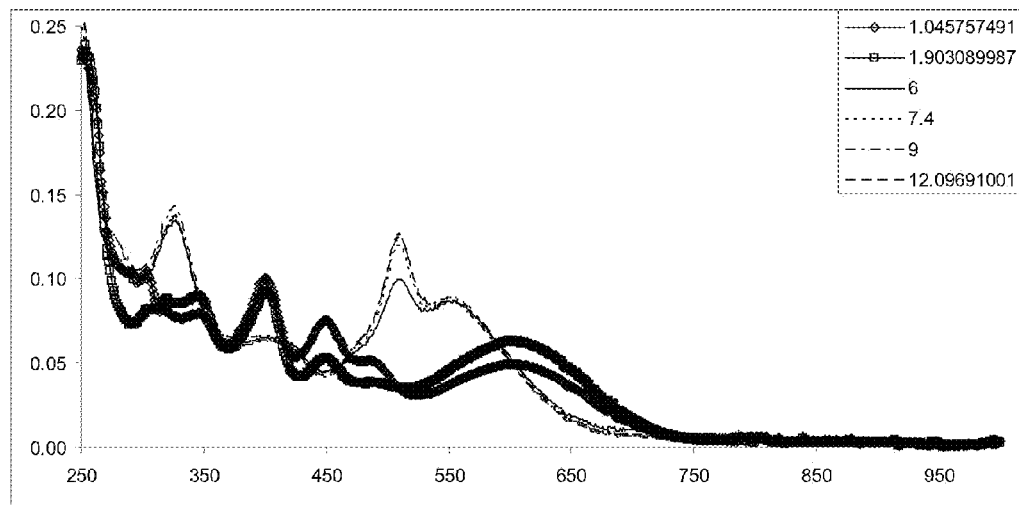
FIG. 21 is a series of pH titration curves of one embodiment of the disclosed dyes, compound 15e.

The new series of compounds based on transposition of the ionizable hydroxyl and amine functionalities combined with the 3-1 transposed regiochemistry disclosed herein displays unanticipated acid-base properties. Known seminaphthorhodafluors display long wavelength absorption at high pH; however, the free amino compound in this series respond to low pH with increased long wavelength absorption. FIG. 21 shows a series of pH titration curves of compound 15e, demonstrating increased long wavelength absorption and decreased short wavelength absorption at low pH.

Preliminary data also indicate that this series (free amino and dimethyl) exhibit red-shifted spectra comparable to others compounds with the 3-1 transposition disclosed herein. Emission maxima of the longest wavelength emitting species are in the range of ~740-780 nm. It is apparent the red-shifted compounds based on the combination of transpositions are considerably more red shifted as compared to the previously reported compounds.

Compound 10-7-(2,5-dimethylphenyl)-13-hydroxy-1H-dibenzo[c,h]xanthen-1-one

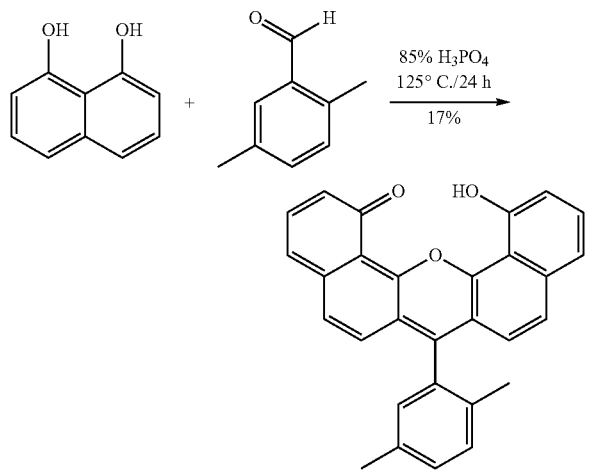

1,8-dihydroxynaphthalene (0.298 mg, 1.86 mmol) and 2,5-dimethyl-benzaldehyde were suspended in 2 mL of 85% $H_3PO_4$, the mixture was vigorously stirred and heated at 125° C. for 24 hours. The mixture was allowed to cool down to room temperature and then poured into 50 mL of water. The precipitate formed was filtered and washed with water (2×50 mL). The target compound is isolated by flash column chromatography on silica gel using $CH_2Cl_{2:MeOH}$ 9:1 for elution. Yield 67 mg, 17%. $^1H$ NMR (400 MHz, $CDCl_3$) δ 7.59-7.45 (m, 4H), 7.35 (s, 2H), 7.16 (s, 2H), 7.10 (s, 2H), 7.04 (d, J=6.8 Hz, 2H), 6.94 (d, J=8.9 Hz, 2H), 2.45 (s, 3H), 2.00 (s, 3H). $^{13}C$ NMR (101 MHz, $CDCl_3$) δ 155.96, 138.17, 136.37, 135.49, 133.06, 132.79, 130.87, 130.65, 129.51, 121.04, 120.73, 120.52, 117.21, 113.46, 21.18, 19.43. HR ESI [M+H$_+$] m/z 417.1476, calc for $C_{29}H_{21}O_3$; 417.1496.

Compound 16a-methyl 2-(1-methoxy-10-oxo-10H-benzo[c]xanthen-7-yl)benzoate

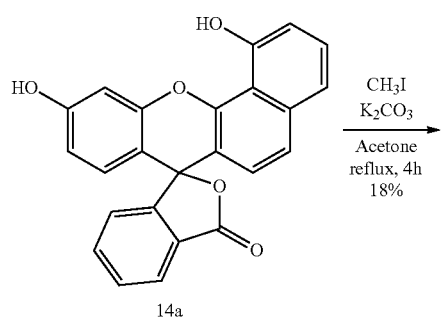

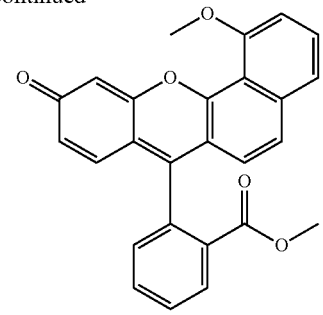

Under argon atmosphere, compound 14a (0.050 g, 0.131 mmol) and $K_2CO_3$ (0.072 g, 0.523 mmol) were suspended in 600 μL of anhydrous DMF. $CH_3I$ (0.111 g, 0.785 mmol) was added in one portion and the mixture heated at 60° C. for 24 hours. The mixture was allowed to cool down to room temperature and then 5 mL of saturated $NH_4Cl$ aqueous solution was added. Compound 16a was isolated by flash column chromatography on silica gel using $CH_2Cl_2$:MeOH 9:1 for elution. Yield 9.8 mg, 18%. $^1H$ NMR (400 MHz, $CDCl_3$) δ 8.29 (dd, J=7.8, 1.1 Hz, 1H), 7.80-7.73 (m, 1H), 7.74-7.67 (m, 1H), 7.60 (t, J=8.0 Hz, 1H), 7.47 (d, J=8.9 Hz, 1H), 7.42 (d, J=7.6 Hz, 1H), 7.35 (dd, J=7.5, 1.0 Hz, 1H), 7.07 (d, J=7.5 Hz, 1H), 6.93 (dd, J=9.1, 5.3 Hz, 2H), 6.68 (q, J=1.8 Hz, 2H), 4.13 (s, 3H), 3.59 (s, 3H). $^{13}C$ NMR (101 MHz, $CDCl_3$) δ 185.38, 165.66, 158.82, 158.40, 151.35, 150.61, 137.97, 135.12, 132.78, 131.21, 130.67, 130.38, 130.32, 129.67, 129.27, 124.52, 123.41, 120.49, 118.58, 116.77, 114.92, 107.91, 105.48, 56.26, 52.39. HR ESI [M+H$_+$] m/z 411.1231; calc for $C_{26}H_{19}O_5$; 411.1237.

Methylation at $R^{18}$ to produce methyl ether 16a dramatically improved the quantum yield. The quantum yield of yellow-orange emitting 16a was 0.4649, 40 times greater than the corresponding neutral compound 15a. It was slightly higher than the yellow-green emitting neutral compound 20a, and >2 times higher than orange-red emitting anion 20c. The compounds (7.5 μM) were analyzed in 10:90 DMSO:aqueous solutions. Fluorescence emission was readily visible in a darkened room when the solutions were excited from below with 3-watt megaMAX 505 nm ALS system. The emission-enhancing properties afforded through the combination of the 3-1 transposition and methylation is in contrast to previously reported methyl ethers of seminaphthofluorescein compounds.

The interested reader is referred to online resources at pubs.acs.org/doi/suppl/10.1021/ja302445w/suppl_file/ja302445w_si_001.pdf for additional NMR, ESI, and absorption spectra, as well as HOMO-LUMO surfaces of some embodiments of the disclosed compounds.

Example 2

Emission in Blood

Figure 22:
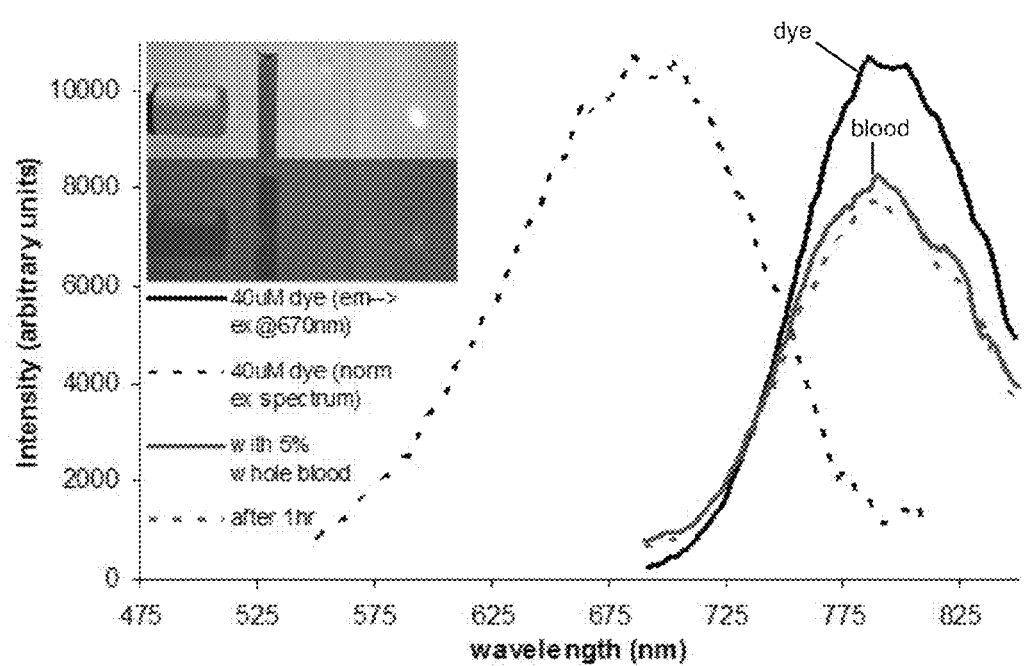
FIG. 22 is a series of spectra of one embodiment of the disclosed dyes, compound 15e, in buffer and in 5% whole blood in buffer.

Compound 15d (Table 1) was diluted to 40 μM in 50% DMSO:50% 25 mM pH 9 phosphate buffer. As shown in FIG. 22, the diluted compound fluoresced with $\lambda_{max\ ex}$=~690 nm and $\lambda_{max\ em}$=~790 nm (Stokes shift=~100 nm, 1834 cm$^{-1}$). Inclusion of whole blood (porcine blood in Na-EDTA, Lampire Biological Laboratories) in the aqueous portion of this solvent to produce a final blood concentration of 5% by volume resulted in only minimal loss of fluorescence attributed to hemoglobin absorption and scattering from blood components. Emission remained stable for at least 1 hr. The absorption profile matches the output of a laser pointer (635-670 nm; max output <5 mW). NIR emission (80 μM) was clearly visible with a digital camera (Kodak EasyShare Z740 in a NIR photograph taken with sec. exposure collected through a Hoya R72 camera filter (%T<1% at <690 nm, %T>90% at >750 nm). Similar results were observed with 5% whole blood, but with increased scattered excitation light clearly visible in the both visible and NIR images, an issue that was easily overcome with a second filter.

The close match between compound 15d's absorption and the output of a common laser pointer allowed its excitation with a simple inexpensive light source.

Furthermore, its NIR emission was detected with a commercial-grade digital camera in normal room light combined with an inexpensive Hoya R72 infrared filter (FIG. 22 inset).

The absorption of compound 4a (Table 1) was clearly visible and remained stable over extended periods of time in the blood solution. Compound 5a (Table 2) was also found to function in 5% blood. Its absorbance and fluorescence spectra faded over time, but remained visible after about an hour (although with only 10-20% of its original emission intensity). Molecular modeling has shown favorable structural interactions of compounds 5f and 24 with glutathione (FIG. 12—compound 24).

Figure 23A:
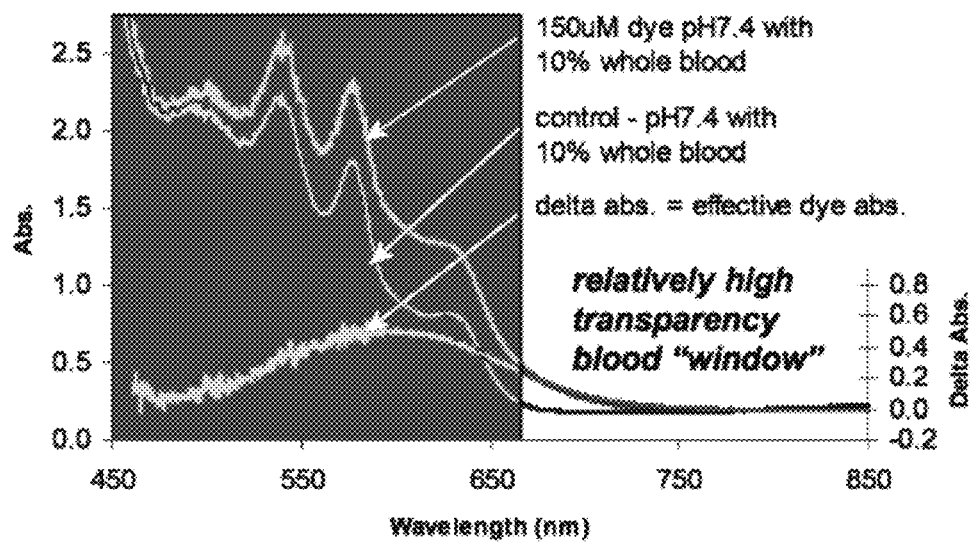
FIG. 23A is an absorption spectrum of one embodiment of the disclosed dyes, compound 15g, in 10% whole blood.
Figure 23B:
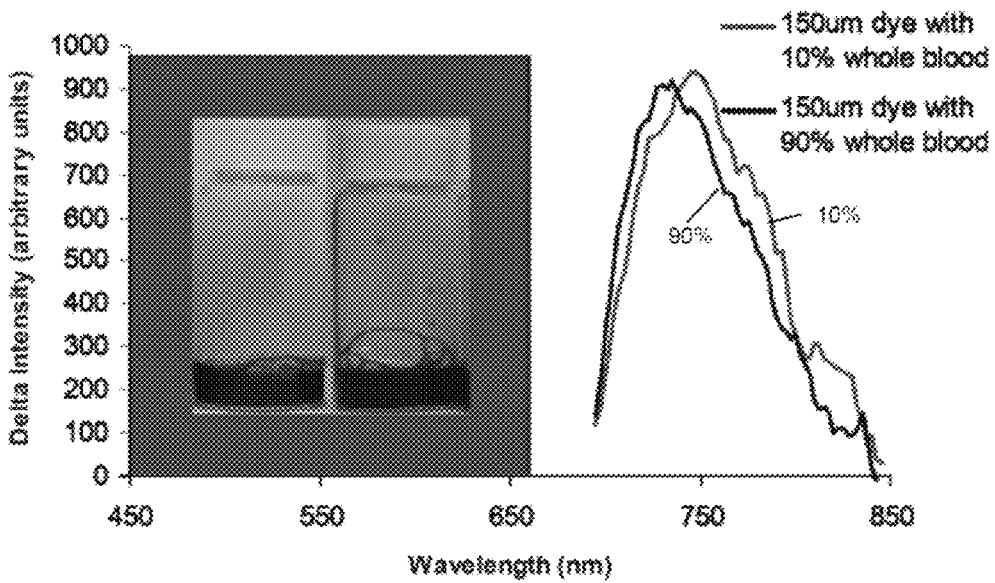
FIG. 23B is a series of emission spectra of one embodiment of the disclosed dyes compound 15g, in 10% and 90% whole blood.

Spectral behavior of compound 15g (type [c] annulated seminaphtho-rhodamine methyl ester (free amine) with the 3-1 transposition) was investigated to determine its potential for sensing use in whole blood. Solutions of compound 15g in 10% or 90% by volume whole blood (porcine blood in Na-EDTA, Lampire Biological Laboratories) were investigated in a 3×3 mm cell. The fluorophore was first dissolved in 50 mM, pH 7.4 phosphate buffer to ensure complete dissolution, and in the case of 90% whole blood, this stock solution was mixed with whole blood in a 1:9 ratio. In the case of 10% whole blood, 1 part whole blood was added to 9 parts of an appropriately diluted (with deionized water) solution of compound 15g stock. In both cases, the final concentration of compound 15g was 150 μM with a final phosphate buffer concentration of 5 mM. FIG. 23A shows the absorbance spectra of compound 15g in 10% whole blood compared to 10% whole blood without the compound. Throughout much of the spectrum, the dye produces a greater absorbance than the blood alone. The change in absorbance between the two spectra provides the effective absorbance of the dye. As shown in FIG. 23A, there is a relatively high transparency blood "window" extending from about 650 nm to 850 nm. The broad absorption and large Stokes shift of this dye allows significant excitation with greater than 50% efficiency at wavelengths beyond that of the major hemoglobin peaks in blood. FIG. 23B shows the emission spectra of compound 15g in 10% and 90% whole blood samples upon excitation at 670 nm. As shown in FIG. 23B, dye emission is clearly seen in both blood samples with an emission spectrum maximum of about 750 nm. The photograph inset in FIG. 23B demonstrates that 10 and 90% whole blood samples (left and right, respectively) are nearly indistinguishable by the naked eye.

Compound 8 (type [c] fully annulated naphthofluorescein methyl ester with 3-1 transposition) displays a maximum absorption at greater than 800 nm, well past that of hemoglobin absorption in blood. As a result, compound 8 also may perform well in blood.

Example 3

Synthesis and Characterization of Rhodamine Bis-Boronic Acids

Compound 51—seminaphthorhodamine bis-boronic acid: With reference to Scheme 9 (FIG. 10), the starting material, 2-(4-amino-2-hydroxybenzoyl)benzoic acid was obtained via the basic hydrolysis of rhodamine 110 at 160° C. over 3 hours in 92% yield. Acid condensation with 1,6-aminohydroxynaphthalene using a 1:1 mixture of $CH_3SO_3H$:TFA afforded the corresponding seminaphthorhodamine 50 in 63% yield after isolation by flash column chromatography with $CH_2Cl_2$:MeOH, 9:1. Reductive amination to produce the corresponding bis-boronic acid 51 was carried out in dichloroethane (DCE) in two steps. Other solvents including MeCN and THF were also used, but gave low yields (less than 1%) of the desired target. The first step involved the reaction of 50 with 2-formylboronic acid and triacetoxy sodium borohydride under microwave irradiation at 130° C. for 40 minutes. The microwave vial was opened, acetic acid was added in one portion, and the mixture was heated for an additional 40 min at 130° C. The mixture was neutralized with saturated $NaHCO_3$, and the target compound was isolated by preparative TLC using $CH_2Cl_2$:MeOH 9:1. The target compound was characterized by $^1H$ NMR, HR ESI MS, and its purity (96%) was determined by reversed phase HPLC.

Compound 53—naphthorhodamine bis-boronic acid: With reference to Scheme 10 (FIG. 11), naphthorhodamine 52 was synthesized in 74% yield by the acid promoted condensation of phthalic anhydride and 1,6-aminohydroxynaphthalene via heating in the presence of trifluoromethane sulfonic acid at 100° C. for 2 hours, then at 140° C. for an additional 2 h under argon. Reductive amination to produce the corresponding bis-boronic acid 53 was carried out in DCE in two steps as described above. Optimal reaction conditions were obtained by monitoring the reaction by reversed phase HPLC. The target compound was isolated in 38% yield by preparative TLC using $CH_2Cl_2$:MeOH 95:5 for elution. Naphthorhodamine 52 and the target compound were characterized by $^1H$ NMR, HR ESI MS, and their purity (99% and 95% respectively) was determined by reversed phase HPLC on a $C_{18}$ reversed phase column and a gradient solvent system composed of $H_2O$:1% TFA in MeCN for elution.

Figure 27A:
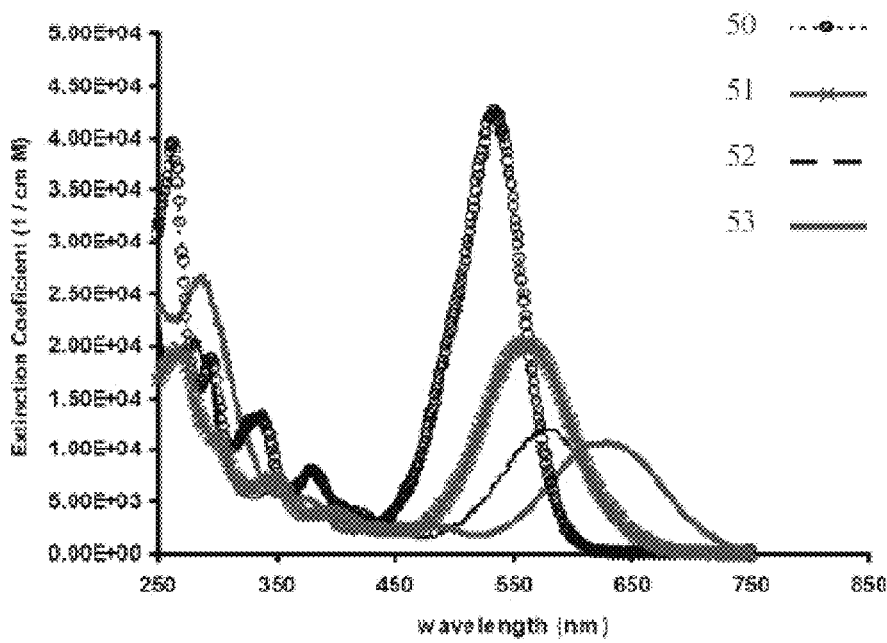
FIGS. 27A-F are absorption and fluorescence spectra of two embodiments of rhodamine bis-boronic acids, compounds 51 and 53, and their respective precursors, compounds 50 and 52. Spectra were obtained in DMSO:buffer 1:9 (FIGS. 27A-C) and DMSO:buffer 1:1 (FIGS. 27D-F).
Figure 27B:
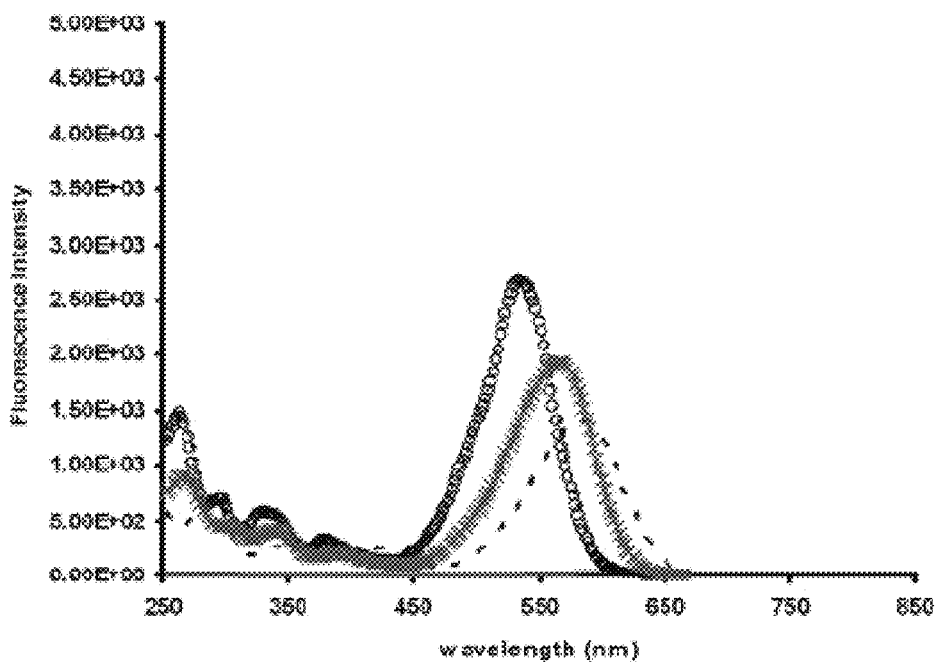
Figure 27C:
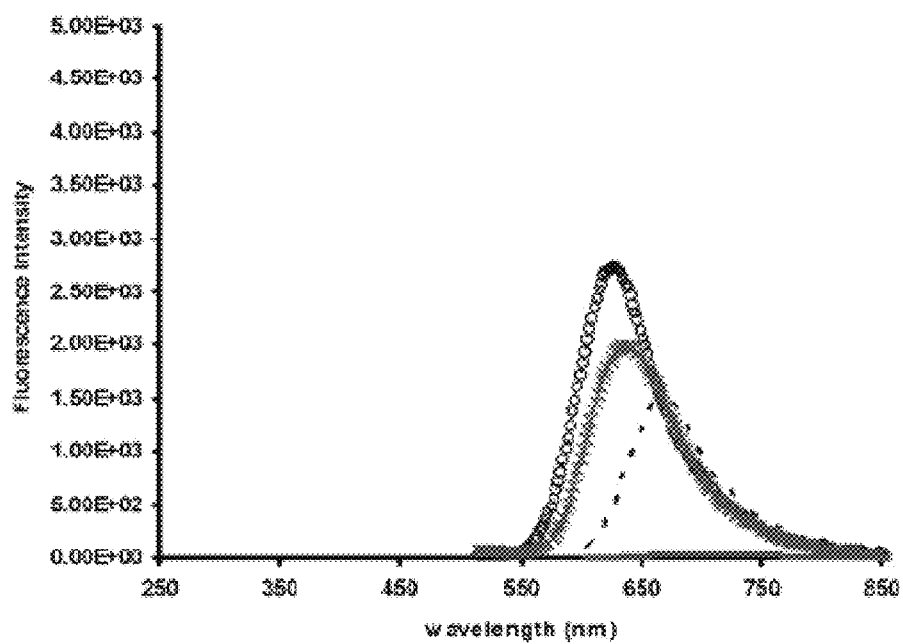
Figure 27D:
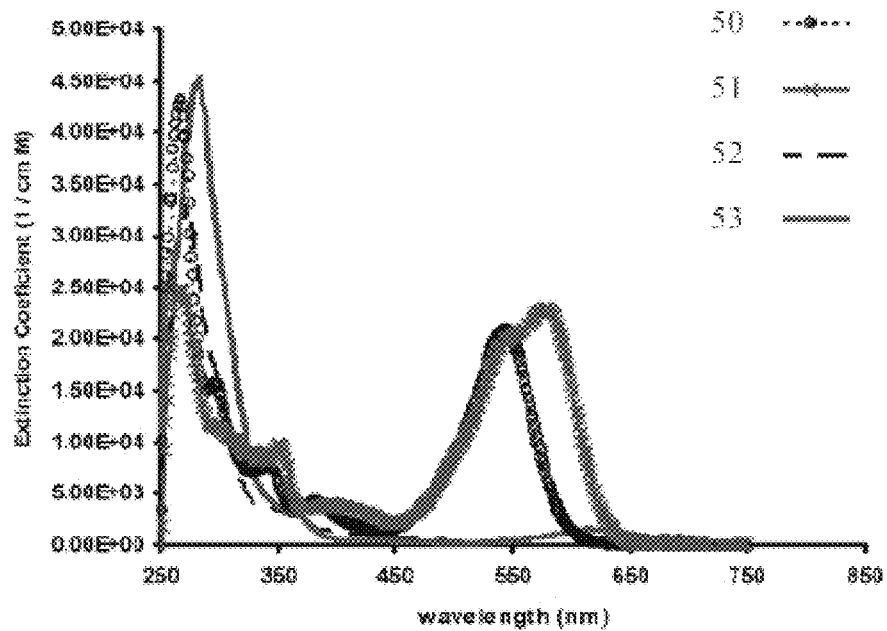
Figure 27E:
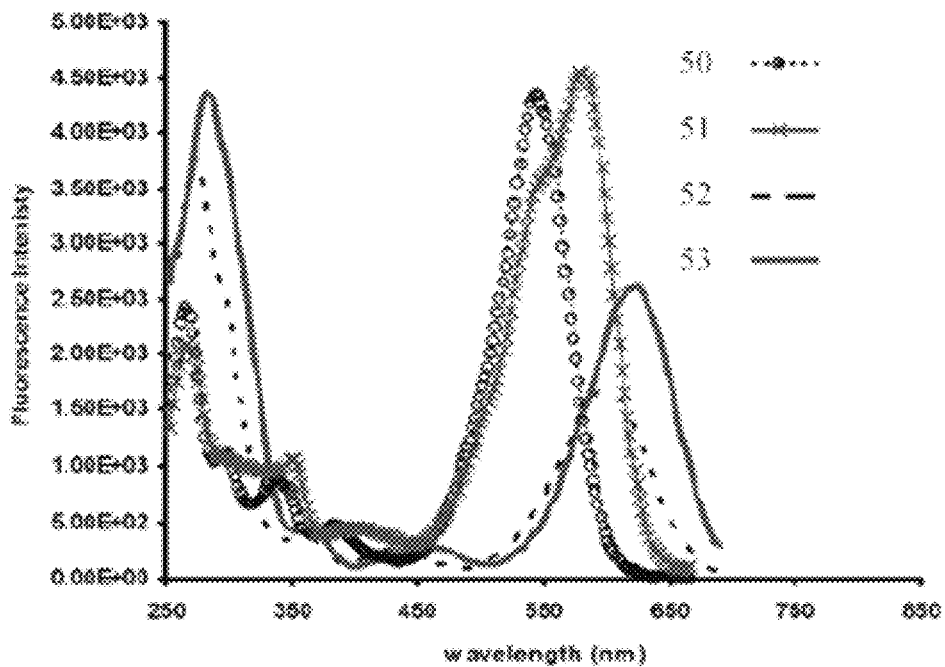
Figure 27F:
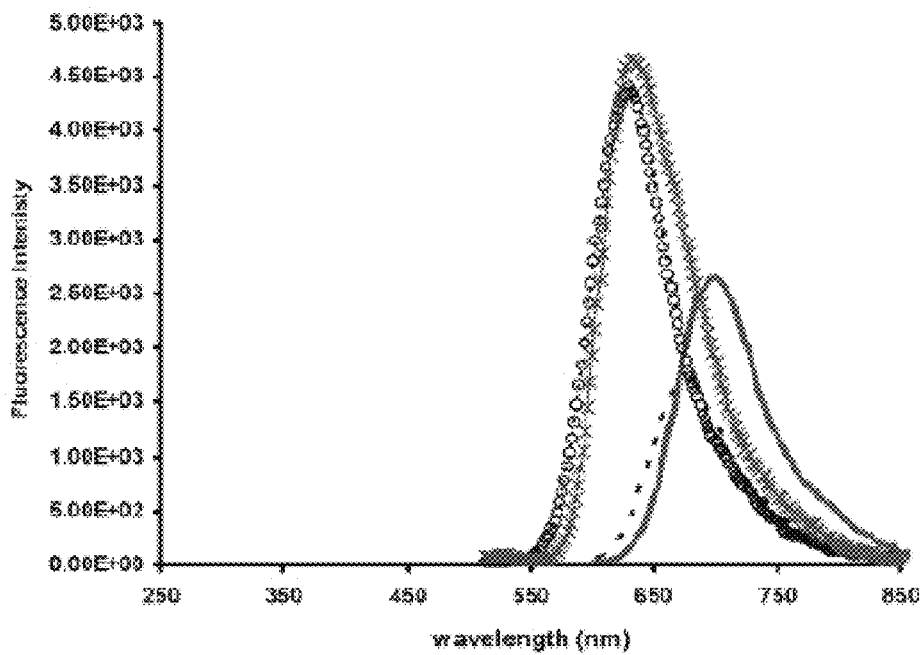

Characterization: The spectral properties of compounds 50-53 were determined. Absorption and fluorescence spectra of solutions of the rhodamine bis-boronic acids 51 and 53, and their respective precursors 50 and 52, are shown in FIGS. 27A-C (in DMSO:buffer 1:9) and 27D-F (DMSO: buffer 1:1). Precursor 50 (2.25 μM) and bis-boronic acid compound 51 (3.75 μM) were excited and monitored at 500 nm and 675 nm. Precursor 52 (12.5 μM) and bis-boronic acid compound 53 (7.5 μM) were excited and monitored at 590 nm and 700 nm. Excitation and emission spectra were normalized to their absorbance at the excitation wavelength, and are proportional to quantum yield.

The results are summarized below in Table 5. The seminapthorhodamine 50 maximum absorption in DMSO buffer 1:9 was at 535 nm (40 nm to the red of rhodamine 110). Its maximum emission at 628 nm displayed a reasonable quantum yield of 19% and was red shifted nearly 100 nm as compared to rhodamine 110. The corresponding bis-boronic acid 51 was further red shifted with maximum absorption and emission at 560 and 638 nm, respectively. Emission was slightly quenched through photoinduced electron transfer (PET) in the boron-nitrogen system as evidenced by the lower quantum yield. It is interesting to note that the quenching for the original "RhoBo" and the fully annulated bis-boronic acid 53 discussed below is much greater than the asymmetric bis-boronic acid 51.

The maximum absorption of napthorhodamine 52 was further shifted to 578 nm with emission wavelength and quantum yield (668 nm, 10%) comparable to commercially available naphthofluorescein. The corresponding bis-boronic acid 53 was further red shifted with maximum absorption and emission at 628 and 692 nm, respectively. Although it displayed a reasonably strong blue/green color, its fluorescence was nearly completely quenched, allowing for a potential turn-on type sensor. Like the other compounds, its emission was slightly redder and its quantum yield was slightly higher in DMSO buffer 1:1. However, like its corresponding rhodamine precursor 52, it exists primarily in the closed and colorless lactone form in this solvent.

TABLE 5

| Compound | Abs (ε, M$^{-1}$cm$^{-1}$) | Ex/Em (Q.Y.) | Brightness | DMSO:buffer ratio[a] |
|---|---|---|---|---|
| Rhodamine 110[b] | 495 (66800 @ 492) | NA/523 (0.91) | 60788 @ 492 | NA |
| RhoBo | 501 (22149) | 502/528 (0.30)[c,f] | 6645 | 1:9 |
| 50 | 535 (42701) | 534/628 (0.19) | 8083 | 1:9 |
| Bis-boronic acid 51 | 560 (20326) | 568/638 (0.15)[e] | 3032[e] | 1:9 |
| 52 | 578 (11994)[d] | 584/668 (0.10) | 1144[d] | 1:9 |
| Bis-boronic acid 53 | 628 (10759)[d] | 612/692 (0.004)[f] | 43[d,f] | 1:9 |
| Rhodamine 110 | 503 (67905) | 502/526 (NA) | NA | 1:1 |
| RhoBo | 504 (21003) | 504/528 (NA) | NA | 1:1 |
| 50 | 542 (21064) | 542/630 (0.30) | 6298 | 1:1 |
| Bis-boronic acid 51 | 579 (23096) | 580/643 (0.35) | 8037 | 1:1 |
| 52 | 602 (1081)[g] | 596/676 (0.11) | 121[g] | 1:1 |
| Bis-boronic acid 53 | 616 (1616)[g] | 624/700 (0.18) | 292[g] | 1:1 |

[a]Final pH 7.4 phosphate buffer concentration was 12.5 mM.
[b]Solvent was 10 mM HEPES, pH 7.5, 15% (v/v) EtOH; Values from Leytus et al., *Biochem. J.* 209, 299 (*1983).
[c]Value taken from Halo et al., *J. Am. Chem. Soc.* 131, 438 (2008).
[d]Partial lactone formation.
[e]Weak PET quenching.
[f]Strong PET quenching.
[g]Near complete lactone formation.

Example 4

Saccharide Sensing and Selectivity

Responses of the boronic acid probes, compounds 51 and 53, were monitored over a wide range of glucose, ribose, and fructose concentrations in various solvents. Solvents including MeCN, MeOH, EtOH, DMSO and buffer were initially screened for sugar sensing. Probes were partially soluble in MeCN and buffer, and soluble in MeOH, EtOH and DMSO. DMSO mixtures were chosen for further studies.

Figure 28:
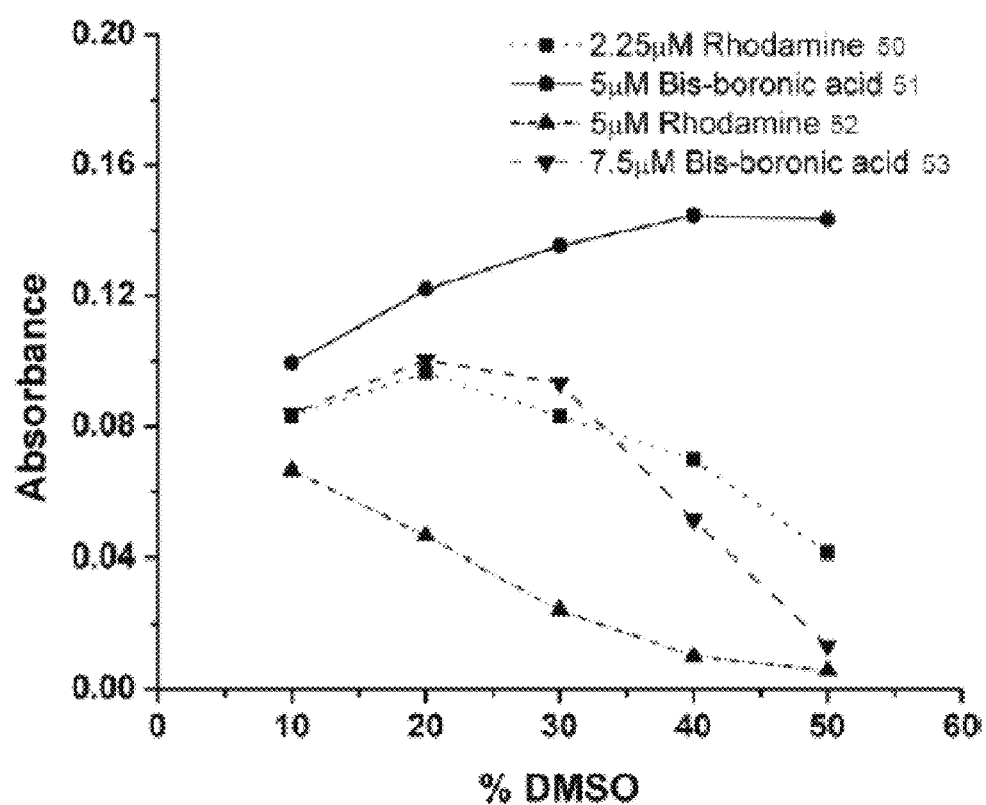
FIG. 28 is a series of DMSO titration curves for two embodiments of rhodamine bis-boronic acids compounds 51 and 53, and their respective precursors, compounds 50 and 52; final pH 7.4 phosphate buffer concentration was 12.5 mM.

Due to the solvent-dependent lactone ring opening-closing equilibrium (Scheme 11) that these type of probes exhibit, a DMSO titration was carried out, in order to determine the range of possible conditions for sugar sensing. Samples were titrated from 0-60% DMSO. The final pH 7.4 phosphate buffer concentration was 12.5 mM. Absorbance values were measured as follows: seminaphthorhodamine 50—532 nm, bis-boronic acid 51—578 nm, naphthorhodamine 52—578 nm, bis-boronic acid 53—627 nm. As shown in FIG. 28, at lower DMSO concentration, rhodamine precursors 50 and 52 as well as the bis-boronic acids 51 and 53 exist at least to some extent as the colored carboxylate species. As the DMSO concentration increased, the lactone form predominated (low absorbance values) for all but bis-boronic acid 51. For this case, the carboxylate form predominated over this DMSO concentration range. At DMSO concentrations of 60-90%, precipitation occurred for all cases; however, at 90% DMSO, all compounds were soluble and predominantly in their colorless closed lactone forms.

It is interesting to note that the boronic acid derivatives are less prone to lactone formation than their corresponding rhodamine precursors.

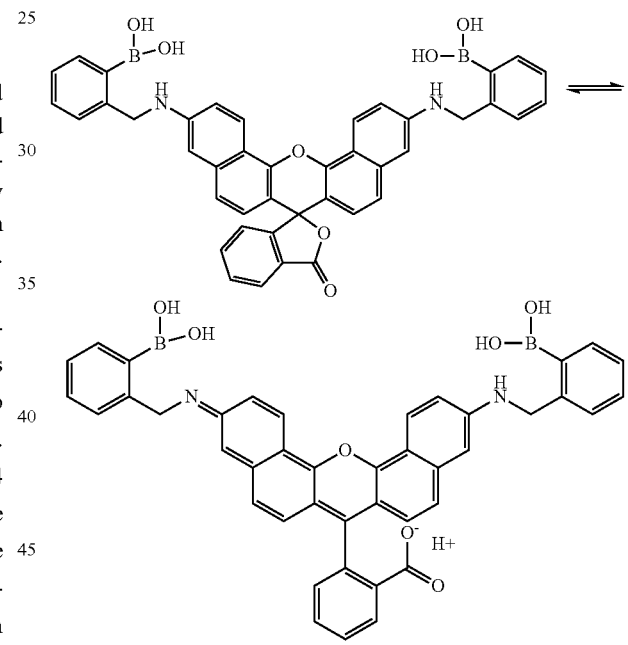

Scheme 11

Initial screening for sensing of glucose, fructose and ribose using these probes in mixtures DMSO:buffer 9:1 (final pH 7.4 phosphate buffer concentration of 12.5 mM) used in our previous work, showed that no changes in either absorbance or fluorescence were observable. Incubation either at room temperature or 37° C. for up to 24 h, gave similar results. It appears that sugar binding did not sufficiently alter the lactone equilibria in this solvent.

The spectral behavior of both compounds 51 and 53 in the presence of saccharides was further investigated in both 1:1 and 1:9 DMSO-buffer (final pH 7.4 phosphate buffer concentration of 12.5 mM) solutions. Both bis-boronic acids responded to binding of sugars through a red shift in their emission and the expected increase in fluorescence intensity.

Figure 29A:
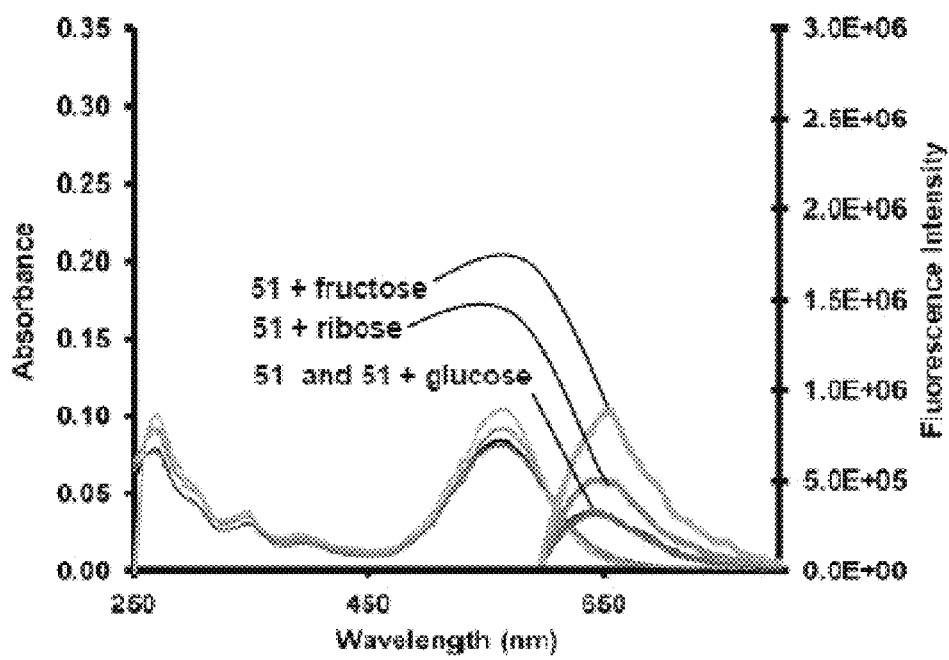
FIGS. 29A-D are absorbance and fluorescence spectra of one embodiment of a rhodamine bis-boronic acid, compound 51, in response to various saccharides.
Figure 29B:
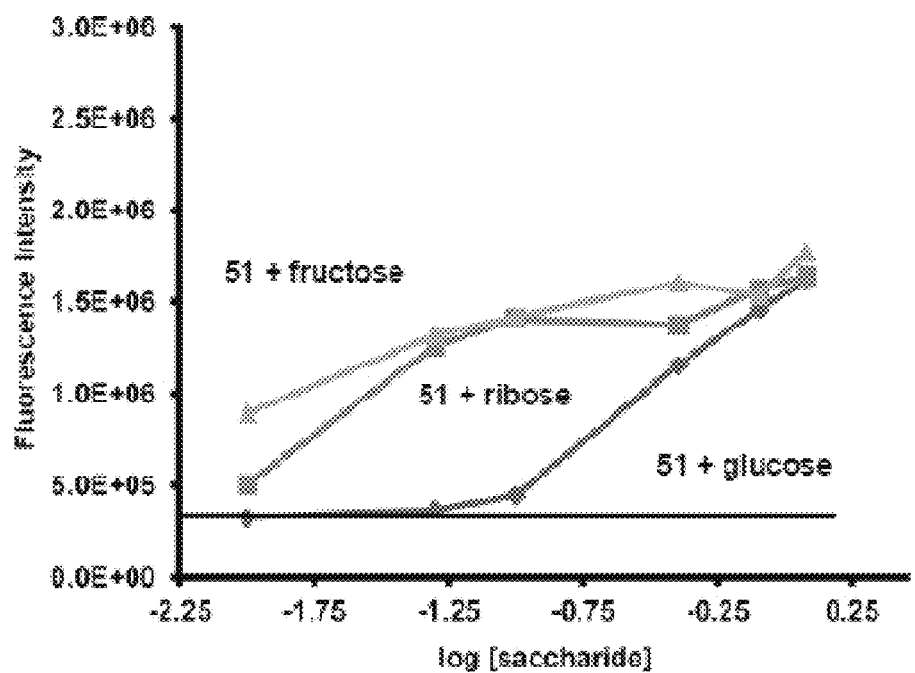
Figure 29C:
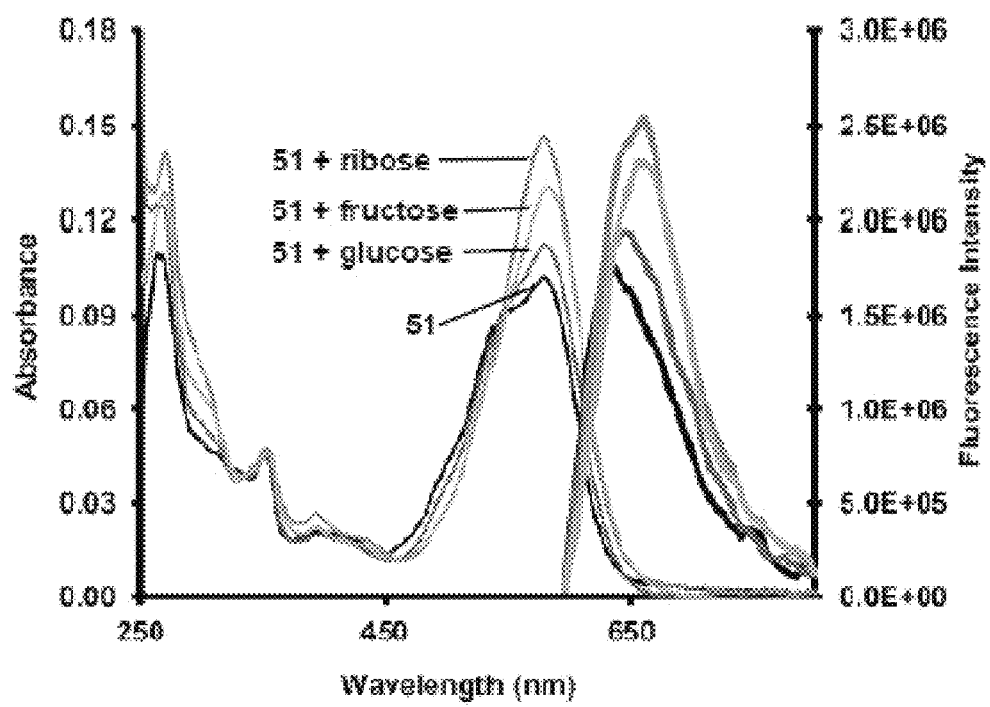
Figure 29D:
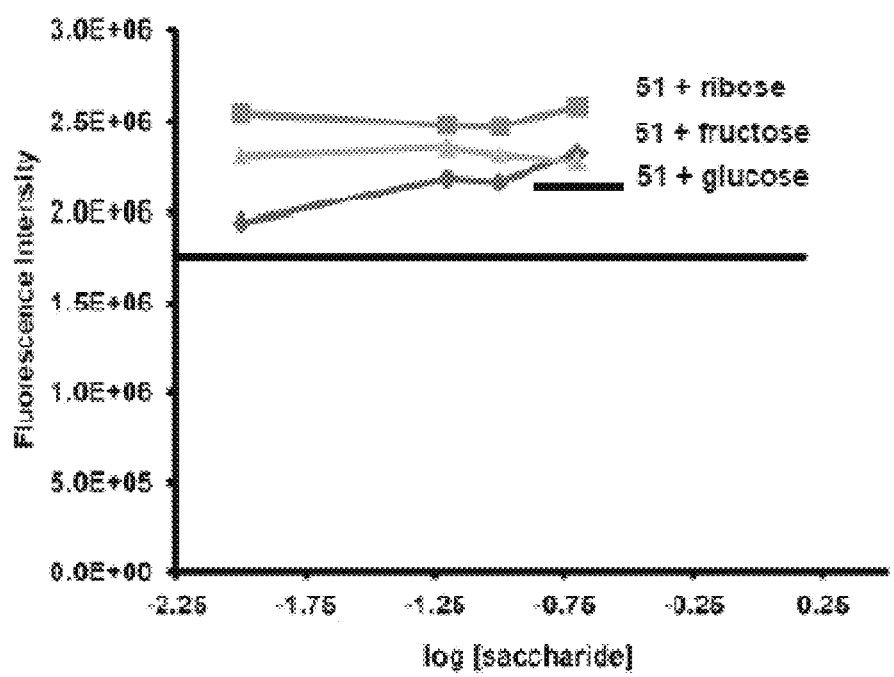

FIGS. 29A-D show the response of bis-boronic acid 51 to fructose, ribose and glucose under the two solvent conditions mentioned above. FIG. 29A is absorption and emission spectra of compound 51 (3.75 µM) in response to 10 mM sugars in DMSO:buffer 1:9; FIG. 29B is fluorescence emission (ex. 580 nm/em. 660 nm) as a function of sugar concentration in DMSO:buffer 1:9; FIG. 29C is absorption and emission spectra of compound 51 (3.75 µM) in response to 10 mM sugars in DMSO:buffer 1:1; FIG. 29D is fluorescence emission (ex. 580 nm/em. 640 nm) as a function of sugar concentration in DMSO:buffer 1:1. The final pH 7.4 phosphate buffer concentration was 12.5 mM. The horizontal lines in FIGS. 29B, 29D represent fluorescence of compound 51 in the absence of analyte. In the 1:9 DMSO: buffer system, this asymmetric rhodamine bis-boronic acid responded more strongly to fructose (FIGS. 29A and 29B). An increase in fluorescence intensity was observed for fructose and ribose at the lowest concentration investigated. At high sugar concentrations, the response for all three sugars converged. A near 2-fold increase in absorbance resulted in a greater than 5-fold increase in fluorescence for all sugars. The solvent system was found to have a large effect on the response. Bis-boronic acid 51 responded most strongly to ribose in the 1:1 DMSO buffer system (FIGS. 29C and 29D). An approximately 1.5-fold increase in both absorbance and fluorescence was observed over the entire concentration range investigated. Binding of all three sugars occurred at lower concentrations as compared to the 1:9 DMSO:buffer system, with the response of both ribose and fructose having already plateaued at 10 mM, the lowest concentration investigated. Unlike the 1:9 solvent system, there were significant spectral differences in the responses toward different sugars (FIG. 29C compared to FIG. 29A).

Figure 30A:
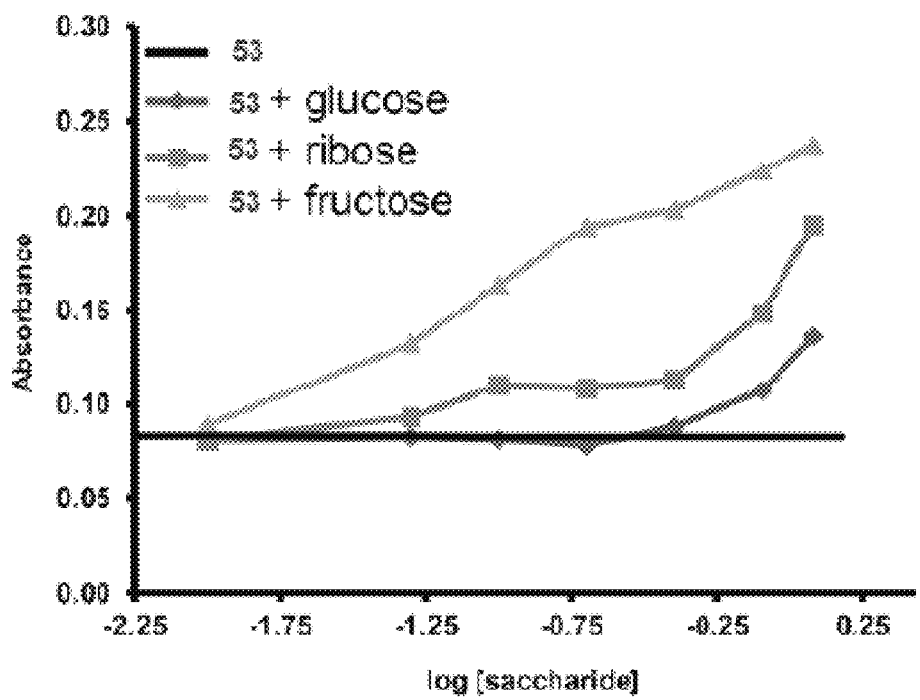
FIGS. 30A-D are absorbance and fluorescence spectra of one embodiment of a rhodamine bis-boronic acid, compound 53, in response to various saccharides.
Figure 30B:
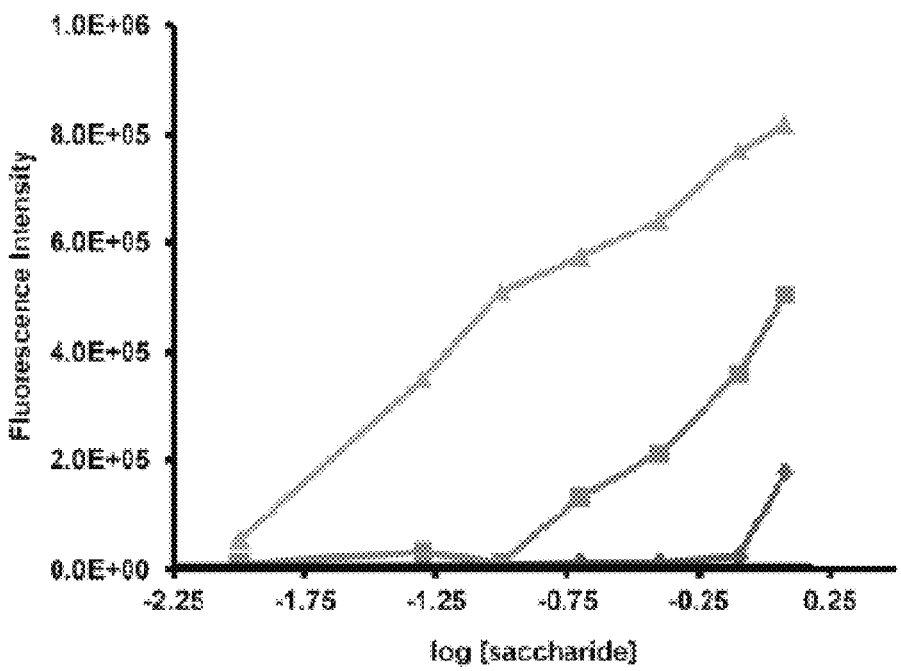
Figure 30C:
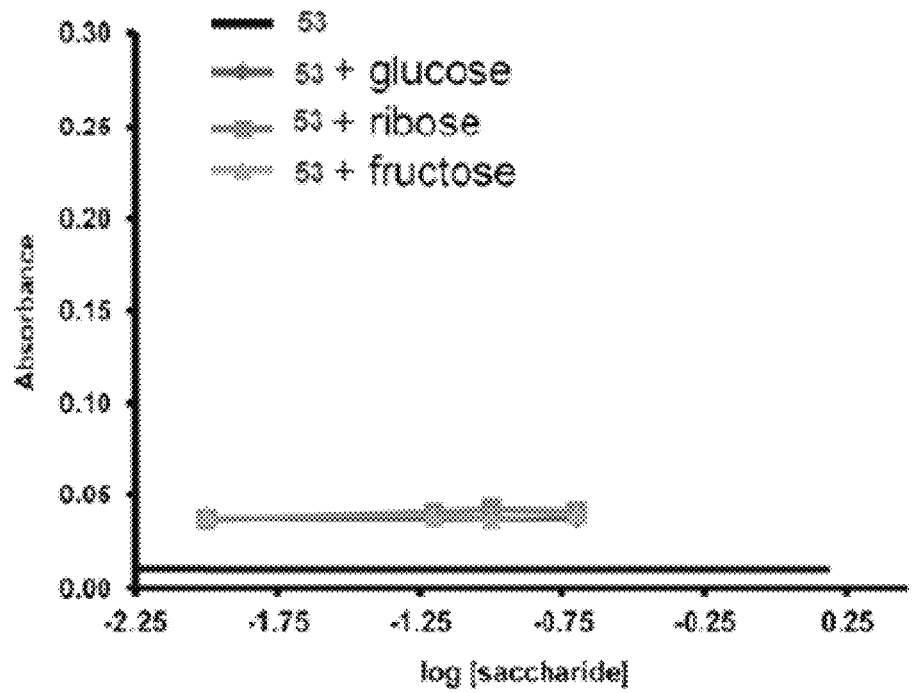
Figure 30D:
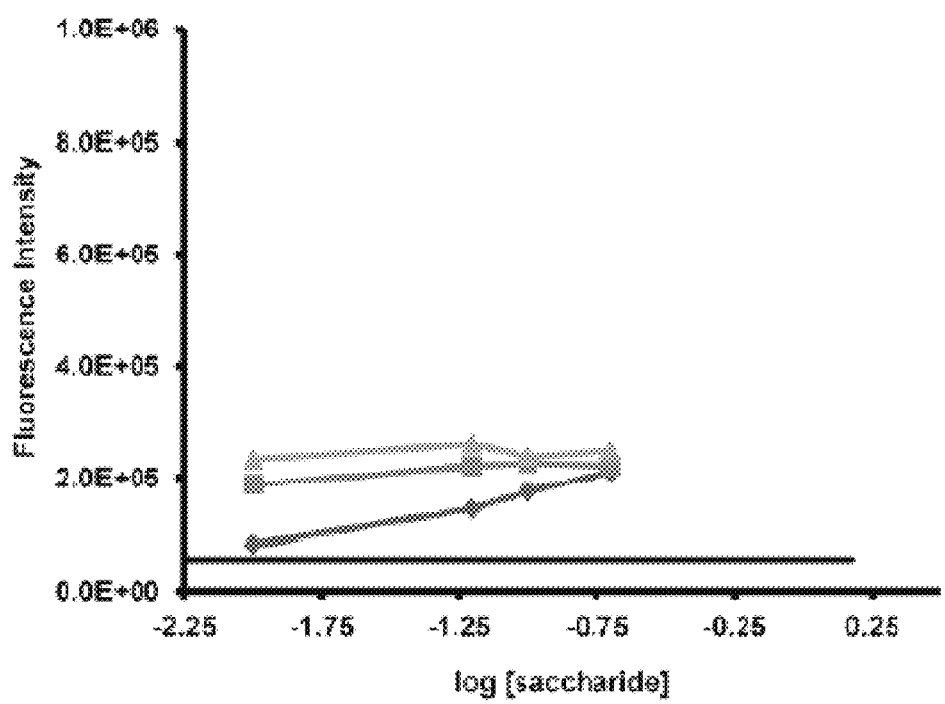

There were significant differences between the responses of asymmetric bis-boronic acid 51 and symmetric bis-boronic acid 53. FIGS. 30A-D show the response of compound 53 to fructose, ribose and glucose in both 1:9 and 1:1 DMSO:buffer systems. FIG. 30A is absorption (630 nm) spectra of compound 53 (7.5 µM) as a function of sugar concentration in DMSO:buffer 1:9; FIG. 30B is fluorescence (ex. 630/em. 690 nm) spectra of compound 53 (7.5 µM) as a function of sugar concentration in DMSO:buffer 1:9; FIG. 30C is absorption (640 nm) spectra of compound 53 (7.5 µM) as a function of sugar concentration in DMSO:buffer 1:1; FIG. 30D is fluorescence (ex. 640/em. 700 nm) spectra of compound 53 (7.5 µM) as a function of sugar concentration in DMSO:buffer 1:1; The final pH 7.4 phosphate buffer concentration was 12.5 mM. Horizontal lines represent absorbance and fluorescence of compound 53 in the absence of analyte. Of the three sugars screened, compound 53 responded almost exclusively to fructose at concentrations below 100 mM in the 1:9 DMSO-buffer system (FIGS. 30A, 30B). At the highest concentration of fructose investigated, a less than 3-fold increase in absorbance at 630 nm resulted in a greater than 140-fold turn-on response of fluorescence emission at 710 nm upon excitation at 630 nm. No spectral shifts were observed in response to any of the sugars. The increase in absorbance may be at least partially the result of lactone opening upon sugar binding. The increase in fluorescence is largely the result of near complete disruption of the PET quenching in the boron-nitrogen system of the free rhodamine bis-boronic acid. It was estimated that the quantum yield of compound 53 after binding approaches 20% or more (140-fold fluorescence increase divided by 3-fold absorbance increase multiplied by the quantum yield of the free compound 53=0.186) which is greater than the quantum yield of precursor 52. Secondary interactions and additional rigidification of the chromophore upon binding could be responsible for this further enhancement of emission. Again, the solvent system was found to have a major effect. Affinity for ribose was greatly increased, approaching the response observed for fructose at the lowest concentration investigated (10 mM) upon changing the solvent system to 1:1 DMSO-buffer. Binding of all three sugars at lower concentrations (FIGS. 30C and 30D) was found to increase, and the response of all three sugars converged to nearly a 5-fold increase in emission at 720 nm upon excitation at 640 nm. Free bis-boronic acid 53 in 1:1 DMSO-buffer was colorless but binding of sugars promoted opening of the lactone leading to a green-blue color.

Figure 31:
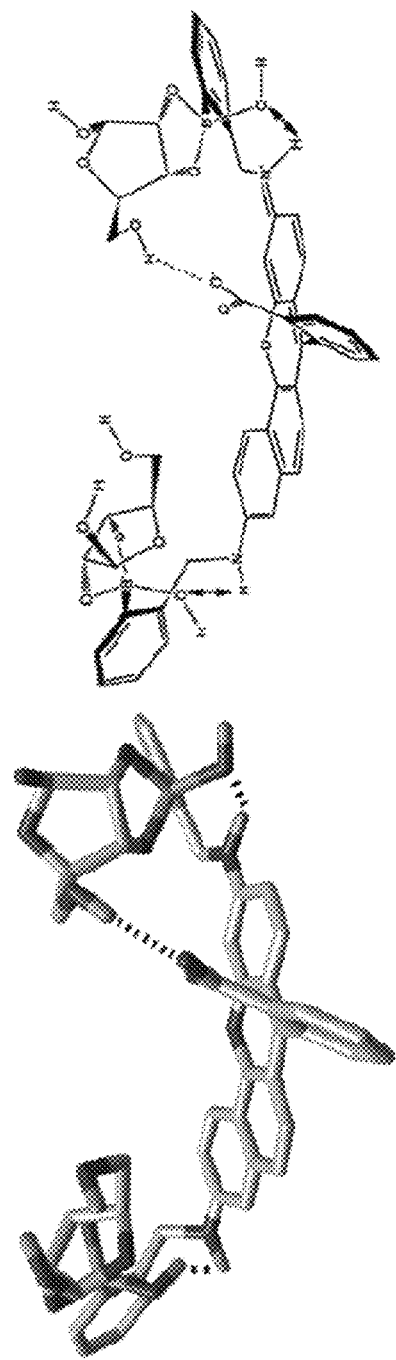
FIG. 31 shows the energy-minimized structure of one embodiment of a complex formed between a ribose and one embodiment of a rhodamine bis-boronic acid compound, compound 51.

When the solvent system is mostly aqueous (1:9 DMSO: buffer), solvation by water inhibits intramolecular interactions by salt bridges, allowing the sugar boronate complexes in compound 51 to adopt practically any possible conformation reaching the carboxyl group without problem, especially for the side where the rhodamine system ring is not extended. For the relatively less aqueous system (1:1 DMSO:buffer), the selectivity turns slightly towards ribose due to the enhancement of intramolecular binding interactions between the bound sugar and dye. FIG. 31 shows a model of ribose bis-boronate of compound 51 describing the electrostatic interactions within the N—H—O—B atoms in a 1:1 DMSO:buffer solution. Electrostatic attraction between N—H—O—B atoms restricts rotation of the C—B bond resulting in selectivity for the ribose complex. Only one of the boronates can reach the carboxylate.

Figure 32:
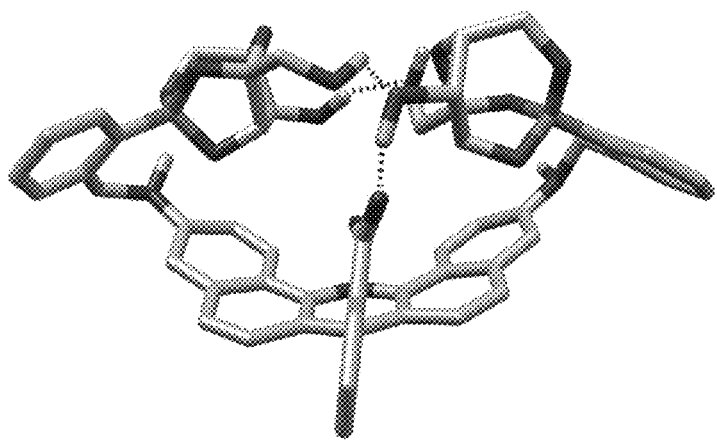
FIG. 32 shows the energy-minimized structure of one embodiment of a complex formed between two molecules of fructose and one embodiment of a rhodamine bis-boronic acid compound, compound 53.

Compound 53 has both boronic acid groups far from each other and from the carboxylate compared to compound 51. In the 1:9 DMSO:buffer solvent system the selectivity followed the normal behavior (fructose>ribose>glucose). When the ratio DMSO:buffer is 1:9, the intramolecular electrostatic interactions are practically nonexistent, allowing more freedom to adopt many possible conformations. If saccharide bis-boronates are formed, the interactions between them can bend the planar chromophore slightly to allow interactions with the carboxylate. Upon changing the solvent system to 1:1 DMSO-buffer, the affinity of symmetric compound 53 for ribose was greatly increased, approaching the response observed for fructose at relatively low concentrations. In this more organic solvent system, the asymmetric boronic acid compound 51 reversed its selectivity and responded most strongly to ribose. For the system with DMSO:buffer 1:1 ratio, the electrostatic interactions are very weak, but strong enough to restrict the molecule from adopting many possible conformations. FIG. 32 shows a model of a bis-boronate complex of compound 53 with two molecules of fructose.

Both compounds 51 and 53 exhibited selectivity trends (fructose >ribose >glucose) in the 1:9 DMSO:buffer system. Compound 53 is particularly attractive as a candidate for selective sugar determination as it responded exclusively to fructose through a clear to blue-green color change with corresponding turn-on NIR fluorescence enhancement of up to 140-fold and no interference from other sugars at concentrations below 100 mM.

Example 5

Screening Dyes

Embodiments of the disclosed NIR dyes can be screened by determining properties of each fluorophore, including : 1) wavelength of maximum absorption of each form (i.e., neutral and ionized); 2) molar absorptivity of each form; 3) wavelength of maximum excitation of each form; 4) wavelength of maximum emission of each form (corrected for pmt (photomultiplier) response); 5) Stokes shift in units of both nm and energy of each form; 6) complete Excitation-Emission Matrix, EEM (corrected for pmt response) covering a wavelength region that includes solvent adduct, neutral and ionized forms (excitation 335-800 nm; emission 360-850 nm); 7) relative quantum yields of each form; and/or 8) $pK_a$ (or apparent $pK_a$ dependent on the solvent).

A standardized procedure including absorption spectra, excitation emission matrices (EEMs), emission spectra upon common "laser-line" excitations, and excitation spectra of the observed emission peaks, and/or serial dilutions of a pH titration series will provide the data required to characterize the dyes and their various forms.

The screening can be divided into two steps. The first step would be an initial screen of compounds comprised of:

Step 1-A: A single absorption spectra and EEM of ~7.5 M each compound (concentration will be lowered if the absorption is greater than about 0.25, or increased if the absorption is less than about 0.05) in pH 8.25 buffer with 5% DMSO (pH 8.25 is near or slightly greater than the likely $pK_a$ of most of the dyes (with the exception of the proposed fluorinated derivatives), so both anionic and neutral forms will be present in significant (nearly equal) amounts). The DMSO will help with any potential solubility issues of the neutral form (the DMSO amount can be reduced if the dye is sufficiently soluble).

Step 1-B: The same procedure as 1-A, but with 5% buffer, 95% DMSO.

Step 2: Multiple concentrations of the dyes (for molar absorptivity and quantum yield measurements) and multiple pHs (for $pK_a$ measurements) will be investigated for the most promising candidates. When available, appropriate quantum yield standards will allow estimation of absolute quantum yields.

Step 3: Computer-aided molecular modeling can be employed to investigate potential interactions with analytes of interest provided by the various geometries of the analytes and the dye molecules.

Interpretation of results. Steps 1A and 1B will provide a wealth of preliminary data (absorption and emission maxima of each species in both solvents, and an estimate of the relative quantum yield of the long wavelength species in both solvents). This initial first screen will not give any information about molar absorptivity, $pK_a$, or absolute quantum yields. Selected compounds can be investigated further in Steps 2 and/or 3.

Example 6

Detecting and Quantitating Analytes in Biological Fluids

Promising dyes can be investigated to determine their binding with analytes of interest (e.g., GSH, cysteine, homocysteine, SAICAr, S-Ado) and to determine any potential interferences from blood and/or urine. A known procedure used to quantify binding of albumin dyes to blood components can be utilized (Omoefe et al., *J. of Biomed. Optics* July 2001, 6(3), 359-365).

Measurements can be made in artificial blood or urine solutions containing the major fluid components and spiked with an analyte of interest. The major blood components and their mean concentration (mg/L) in blood are: HSA—41,000, HDL—850, LDL—810, globulin—32,000, red blood cells (43.5% hematocrit) 489,375 (Abugo et al., *J. Biomed. Opt.*, 2001, 6, 359-365; Abugo et al., *Anal. Biochem.*, 2000, 279, 142-150). The chemical composition of human urine has been thoroughly investigated and reported by NASA (NASA Contractor Report CR-1802). The composition of simulated urine and urine solutions will be based on their findings. Five major components (urea, creatinine, oxalate, uric acid and citrate) have previously been used to simulate urine content (Ow et al. *IFMBE Proceedings,* 2008, Vol. 21, Part 3, Part 11, 742-745; Osman et al., *Biomed* 2008 *Proceedings* 2008, 21, 742-745).

Apparent binding constants can be estimated directly from raw titration data without any model assumptions; however, the analytical representation of data may be used to simulate dye behavior in a complex mixture with multiple potential interferences. A phenomenological approach involving fits of experimental titration curves may be used model the experimental data and allow rough estimates of the binding of various dyes in mixtures containing components of biological fluids. It may not be possible to test all blood (or urine) components; however, inclusion of the major components should be sufficient to screen embodiments of the disclosed dyes for selectivity toward analytes of interest. Matrix effects may be evaluated by comparing standard calibration curves in the biological fluids with standard calibration curves in an optimal buffer system.

Selectivity may be fine-tuned based on the experimental results combined with further computer aided molecular simulations. Analysis of GSH and SAICAr and S-Ado may be carried out in authentic biological fluids (GSH in blood and SAICAr and S-Ado in urine) using samples spiked with calibration (reference) standards and using quality control (QC) samples. The developed methodology may be evaluated according to standard procedures for method development including (a) accuracy, (b) precision, (c) selectivity, (d) sensitivity, (e) reproducibility, and (f) stability. Recovery of analyte can be determined using standard addition protocols. All biological fluids to be used may be purchased from commercial sources.

Results from optimal conditions for quantification of the analytes of interest in solution along with a similar methodology as described by Orfanos (*Anal. Biochem.,* 1980, 104, 70-74) may be adapted for the detection and quantitation of the analytes of interest in biological fluids deposited in filter paper. Dried blood (or urine) specimens on filter paper are obtainable. For blood spots, disks may be punched from the paper and the blood contents typically eluted/extracted into a small volume of solvent. In conventional analyses, the absorption from hemoglobin remains a major interference. This is typically overcome by further dilution in order to ensure the hemoglobin content is less than 30 μg/ml. Such dilution complicates measurements of analytes present at high concentration and may even prevent analysis of trace analytes. Based on preliminary results (see Example 2), embodiments of the disclosed NIR dyes will function in the presence of at least 5% whole blood. Thus, extraction of the contents of a typical 4.8-mm disk into a small volume (0.6 mL or less, containing one of our dyes) may be used directly without dilution.

In some instances, the dyes may be conjugated to a polymer, e.g., a polyethylene glycol, to provide enhanced selectivity and minimization of interferences. Fluorination of certain embodiments of the disclosed dyes may facilitate solubility in aqueous solutions. In certain instances, dithiothreitol (DTT) may be added to the analysis solution to prevent and/or minimize disulfide formation. At least some embodiments of the disclosed dyes function in the presence of DTT; furthermore, monitoring total GSH-GSSG (via adding DTT to the solution) is feasible since about 90% of blood GSH is in the reduced form and glutathione disulfide (GSSG) levels are similar in both patients and controls (Atkuri et al., *PNAS U.S.A.*, 2009, 106, 3941-3945).

These studies may enable identification of NIR dyes that bind strongly and selectively to analytes of interest. Fluorescence enhancement upon binding may be evaluated and utilized to determine what dye geometries and functional groups favor target analytes or specific interfering components.

Example 7

Glutathione Selectivity Evaluation

Mechanistic studies may be conducted in control experiments (buffered media at physiological conditions or in the presence of a co-solvent if needed) to determine the origin of the selectivity observed for the analytes of interest by embodiments of the disclosed NIR dyes. Conjugates, adducts or reaction products may be isolated and characterized by HPLC and LC-MS ESI. Crystal structures of isolated complexes, adducts or reaction products may be determined by X-Ray crystallography. Binding constants for complex formation between the analytes of interest and NIR fluorescent probes may be obtained using spectrometric methods including: 1H NMR, 2D 1H NMR (ROESY, NOESY), UV-vis or fluorescence.

Selectivity and crossreactivity may be evaluated in the presence of possible interferences (e.g., Cys, Cys-Gly, and/or Cys-Glu for GSH). Influence of factors involved in selectivity/specificity including pH, ionic strength, type of buffering system, and molar ratios of analyte:NIR fluorophore-viologen conjugate may be evaluated using spectrometric methodologies.

Example 8

Selective Detection of SAICAr and S-Ado in Urine

Embodiments of the disclosed NIR dyes functionalized with at least one boronic acid functional group (i.e., —NHR$^c$ where R$^c$ is as defined above) may serve as indicators for ADLS deficiency. Mechanistic investigations and characterization studies similar to those performed in Example 5 may be used to determine selectivity for SAICAr and/or S-Ado detection. Promising candidates may be evaluated in urine and/or synthetic urine samples.

Additional patent documents describing subject matter or background information which may be pertinent to the present disclosure include U.S. Publication No. 2008/0261315, U.S. Publication No. 2010/0051826, and WO 2008/011508, each of which is incorporated in its entirety herein by reference.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a chemical structure selected from

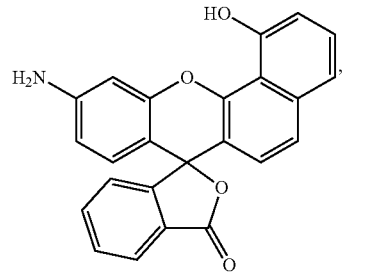

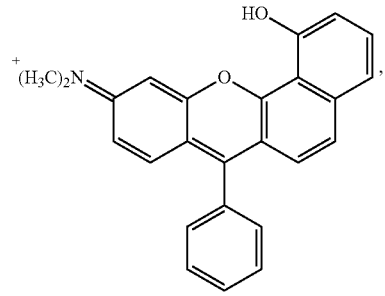

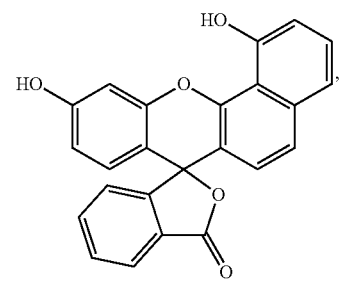

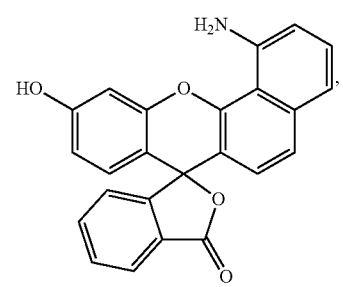

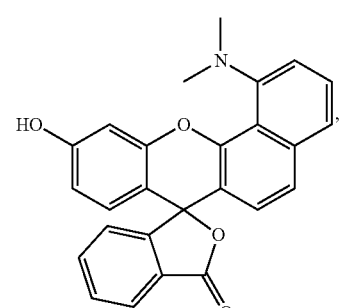

-continued

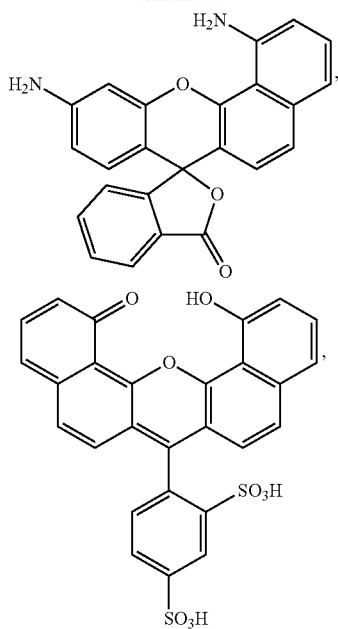

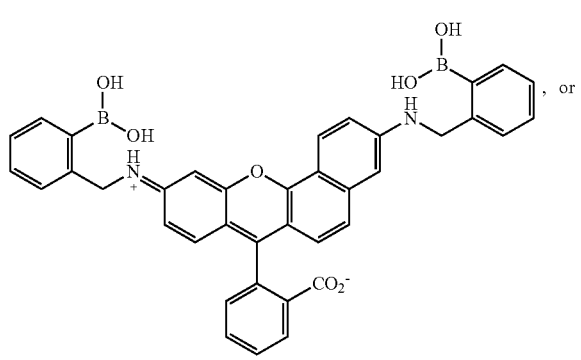

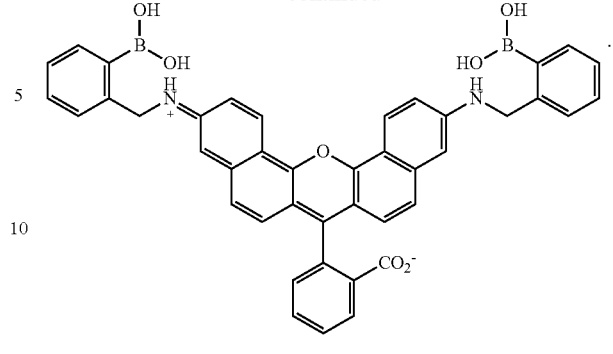

2. A kit for detecting an analyte, comprising at least one compound according to claim 1, wherein the compound when combined with a sample comprising the analyte will undergo a change in its absorbance spectrum, emission spectrum, or both compared to the compound in a sample that does not comprise the analyte.

3. The kit of claim 2, further comprising at least one buffer solution in which the compound when combined with a sample comprising the analyte will undergo a change in its absorbance spectrum, emission spectrum, or both compared to the compound combined with the buffer solution and a sample that does not comprise the analyte.

4. The kit of claim 2, where the analyte comprises glutathione, cysteine, homocysteine, succinyl-5-amino-4-imidazolecarboxamide riboside, succinyladenosine, or a combination of succinyl-5-amino-4-imidazolecarboxamide riboside and succinyladenosine.

5. The kit of claim 2, further comprising a plurality of disposable containers in which a reaction between the compound and the analyte can be performed.

6. The kit of claim 5, where an amount of the compound effective to undergo a detectable change in the absorbance spectrum, the emission spectrum, or both when reacted with the analyte is premeasured into the plurality of disposable containers.

7. A method for selectively detecting an analyte in a biological fluid, comprising:
(a) combining a compound according to general formula (III) or (IV) with a biological fluid to form a solution

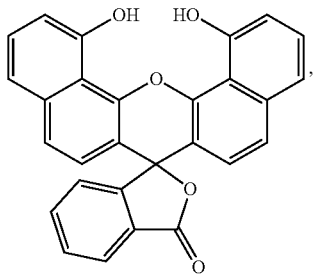

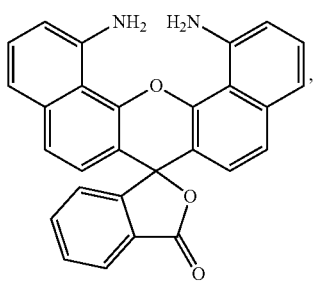

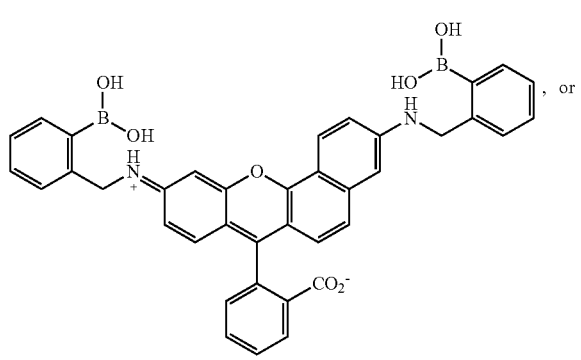

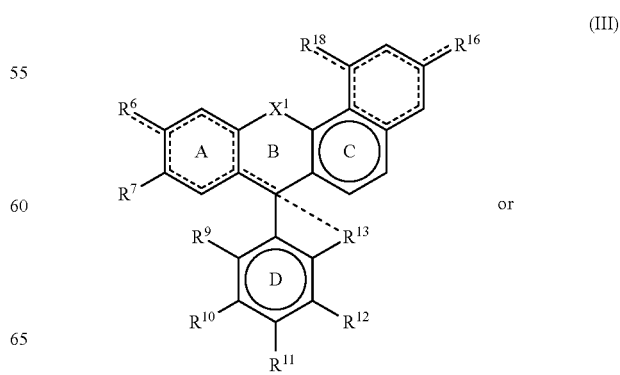

-continued

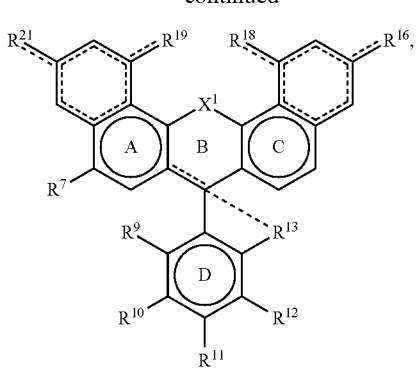

(IV)

where each bond depicted as "-----" is a single or double bond as needed to satisfy valence requirements;
$X^1$ is O, S, or N(H);
$R^6$ is hydroxyl, amino, alkyl amino, or —$NHR^c$ when the bond between $R^6$ and ring A is a single bond, or $R^6$ is oxygen, imino, iminium, alkyl imino, or alkyl iminium when the bond between $R^6$ and ring A is a double bond, where $R^C$ is

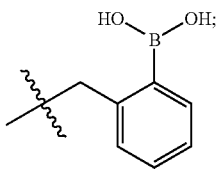 [SMILES: *Cc1ccccc1B(O)O]

$R^7$ is hydrogen or halogen;
$R^9$-$R^{12}$ independently are hydrogen, lower alkyl, carboxyl, amino, or —$SO_3H$;
$R^{13}$ is hydrogen, lower alkyl, lower alkoxy, —$SO_3H$ or —$COOR^{14}$ where $R^{14}$ is hydrogen or lower alkyl and the bond depicted as "-----" in ring B is a double bond, or $R^{13}$ is one or more atoms forming a ring system with rings B and D and the bond depicted as "-----" in ring B is a single bond;
$R^{16}$ and $R^{18}$ independently are hydrogen, hydroxyl, thiol, oxygen, lower alkoxy, amino, alkyl amino, or —$NHR^c$, and at least one of $R^{16}$ and $R^{18}$ is other than hydrogen;
$R^{19}$ and $R^{21}$ independently are hydrogen, hydroxyl, thiol, oxygen, amino, alkyl amino, imino, iminium, alkyl imino, alkyl iminium, or —$NHR^c$ where $R^c$ is as defined above, and at least one of $R^{19}$ and $R^{21}$ is other than hydrogen; and
wherein if $X^1$ is oxygen in general formula (III), then $R^6$ is other than oxygen or alkyl amino, or $R^{13}$ is other than one or more atoms forming a ring system with rings B and D, or $R^{16}$ is other than hydroxyl or hydrogen, or $R^{18}$ is other than hydroxyl or hydrogen, or at least one of $R^7$, $R^9$, $R^{10}$, $R^{11}$, $R^{12}$, $R^{13}$ is other than hydrogen, or
if the compound has a chemical structure according to general formula (IV), then at least one of $R^9$-$R^{13}$, $R^{16}$, $R^{18}$, $R^{19}$, or $R^{21}$ is other than hydrogen, hydroxyl, halogen, oxygen, lower alkyl, amino, or thiol, or $R^{13}$ is one or more atoms forming a ring system with rings B and D and the bond depicted as "-----" in ring B is a single bond;
(b) exposing the solution to a light source; and
(c) detecting the analyte by detecting fluorescence from the compound, wherein the analyte comprises cysteine, homocysteine, glutathione, succinyl-5-amino-4-imidazolecarboxamide riboside, succinyladenosine, or a combination thereof.

8. The method of claim 7 where detecting fluorescence from the compound comprises detecting fluorescence at a wavelength corresponding to an emission spectrum maximum of the compound.

9. The method of claim 8, further comprising quantitating the analyte by measuring an amount of fluorescence from the compound at a wavelength corresponding to an emission spectrum maximum of the compound.

10. The method of claim 7 where the biological fluid comprises blood or urine.

\* \* \* \* \*